United States Patent
Brass et al.

(10) Patent No.: US 8,993,318 B2
(45) Date of Patent: Mar. 31, 2015

(54) PATHOGEN RESTRICTION FACTORS

(75) Inventors: Abraham Brass, Newton, MA (US); Stephen Elledge, Brookline, MA (US)

(73) Assignees: The Brigham and Women's Hospital, Inc., Boston, MA (US); The General Hospital Corporation, Boston, MA (US)

(*) Notice: Subject to any disclaimer, the term of this patent is extended or adjusted under 35 U.S.C. 154(b) by 78 days.

(21) Appl. No.: 13/511,980

(22) PCT Filed: Dec. 10, 2010

(86) PCT No.: PCT/US2010/059934
§ 371 (c)(1),
(2), (4) Date: Sep. 6, 2012

(87) PCT Pub. No.: WO2011/072247
PCT Pub. Date: Jun. 16, 2011

(65) Prior Publication Data
US 2012/0331576 A1 Dec. 27, 2012

Related U.S. Application Data

(60) Provisional application No. 61/285,817, filed on Dec. 11, 2009.

(51) Int. Cl.
| | |
|---|---|
| C12N 5/10 | (2006.01) |
| C12N 5/22 | (2006.01) |
| C12Q 1/68 | (2006.01) |
| C12Q 1/70 | (2006.01) |
| C12N 7/00 | (2006.01) |
| A61K 38/17 | (2006.01) |
| A61K 39/155 | (2006.01) |
| C07K 14/705 | (2006.01) |
| C12Q 1/18 | (2006.01) |

(52) U.S. Cl.
CPC . *C12N 7/00* (2013.01); *A61K 38/17* (2013.01); *A61K 39/155* (2013.01); *C07K 14/705* (2013.01); *C12Q 1/18* (2013.01); *A01K 2217/052* (2013.01); *A01K 2217/075* (2013.01); *A01K 2267/02* (2013.01); *A01K 2267/0337* (2013.01); *C12N 2740/13051* (2013.01); *C12N 2760/10051* (2013.01); *C12N 2760/16151* (2013.01); *C12N 2760/20251* (2013.01); *C12N 2770/24051* (2013.01); *C12N 2770/24151* (2013.01)
USPC .......... 435/325; 435/366; 435/363; 435/455; 424/93.1

(58) Field of Classification Search
CPC .. C12Q 2600/158; C12Q 1/6883; C12Q 1/68; C12Q 2600/118; C12Q 1/18; C12N 15/1131; C12N 15/85; C12N 2720/12352; C12N 2750/10052; G01N 2800/52; G01N 33/56983; A61K 39/39

USPC .......... 435/5, 366, 325, 363, 455; 424/93.21; 514/44 A
See application file for complete search history.

(56) References Cited

U.S. PATENT DOCUMENTS

2009/0221679 A1 9/2009 Espeseth et al.

OTHER PUBLICATIONS

Lange et al, Mol Cell Biol, 2008, 28:4688-4696.*
Smith et al, J Virol, 2013, 87:12957-12966.*
Everitt et al., "IFITM3 restricts the morbidity and mortality associated with influenza," Nature, 484:519-525 (2012).
Huang et al., "Distinct Patterns of IFITM-Mediated Restriction of Filoviruses, SARS Coronavirus, and Influenza A Virus," PLoS Pathogens, 7(1):e1001258 (2011).
Zhang et al., "Interferon-induced transmembrane protein-3 genetic variant rs12252-C is associated with severe influenza in Chinese individuals," Nature Communications, 4:1418 (2013).
Alber et al., "Partial Inhibition of Vesicular Stomatitis Virus by the Interferon-Induced Human 9-27 Protein," Journal of Interferon and cytokine Research, 16:375-380 (1996).
Andreu et al., "Identification of the IFITM family as a new molecular marker in human colorectal tumors," Cancer Research, 66:1949-1955 (2006).
Boulo et al., "Nuclear traffic of influenza virus proteins and ribonucleoprotein complexes," Virus Res., 124:12-21 (2007).
Bouloy et al., "Globin mRNAs are primers for the transcription of influenza viral RNA in vitro," Proc. Natl. Acad. Sci. USA, 75:4886-4890 (1978).
Bradbury et al., "The CD19/CD21 signal transducing complex of human B lymphocytes includes the target of antiproliferative antibody-1 and Leu-13 molecules," J. Immunol., 149:2841-2850 (1992).
Brass et al., "The IFITM proteins mediate cellular resistance to influenza A H1N1 virus, West Nile virus, and dengue virus," Cell, 139(7):1243-1254 (2009).
Buss and Stewart, "Macromolecular interactions in the nucleoporin p62 complex of rat nuclear pores: binding of nucleoporin p54 to the rod domain of p62," J. Cell Biol., 128:251-261 (1995).
Chen et al., "RAB-10 is required for endocytic recycling in the *Caenorhabditis elegans* intestine," Mol. Biol. Cell, 17:1286-1297 (2006).

(Continued)

*Primary Examiner* — Valarie Bertoglio
*Assistant Examiner* — Chi-Feng Hsu
(74) *Attorney, Agent, or Firm* — Fish & Richardson P.C.

(57) ABSTRACT

The use of interferon induced transmembrane protein 1, 2, or 3 (IFITM1, 2, or 3) as a viral restriction factor, and methods of using the same to produce virus, transgenic animals expressing exogenous IFITM1, 2, or 3, and methods of treating or inhibiting viral infections by targeting a gene identified herein.

6 Claims, 37 Drawing Sheets

(56) References Cited

OTHER PUBLICATIONS

Chu and Whittaker, "Influenza virus entry and infection require host cell N-linked glycoprotein," Proc. Natl. Aca. Sci. USA, 101:18153-18158 (2004).

Clarkson et al., "Separate binding sites on nuclear transport factor 2 (NTF2) for GDP-Ran and the phenylalanine-rich repeat regions of nucleoporins p62 and Nsp1p," J. Mol. Biol., 263:517-524 (1996).

Engelhardt and Fodor, "Functional association between viral and cellular transcription during influenza virus infection," Rev. Med. Virol., 16:329-345 (2006).

Evans et al., "IFN-alpha induces homotypic adhesion and Leu-13 expression in human B lymphoid cells," J. Immunol., 150(3):736-747 (1993).

Friedman et al., "Transcriptional and posttranscriptional regulation of interferon-induced gene expression in human cells," Cell, 38:745-755 (1984).

Ge et al., "RNA interference of influenza virus production by directly targeting mRNA for degradation and indirectly inhibiting all viral RNA transcription," Proc. Natl. Acad. Sci. USA, 100:2718-2723 (2003).

Glodowski et al., "RAB-10 regulates glutamate receptor recycling in a cholesterol-dependent endocytosis pathway," Mol. Biol. Cell, 18:4387-4396 (2007).

Grandvaux et al., "The interferon antiviral response: from viral invasion to evasion," Curr Opin Infect Dis., 15:259-267 (2002).

Hale et al., "The multifunctional NS1 protein of influenza A viruses," J. Gen. Virol., 89:2359-2376 (2008).

Haller et al., "Protective role of interferon-induced Mx GTPases against influenza viruses,"Rev. Sci. Tech., 28:219-231 (2009).

Hao et al., "*Drosophila* RNAi screen identifies host genes important for influenza virus replication," Nature, 454:890-893 (2008).

Haye et al., "The NS1 Protein of a Human Influenza Virus Inhibits Type * Interferon Production and the Induction of Antiviral Responses in Primary Human Dendritic and Respiratory Epithelial Cells," Journal of Virology, 83, 13; 6849-6862, 2009.

Huang et al., "SARS coronavirus, but not human coronavirus NL63, utilizes cathepsin L to infect ACE2-expressing cells," J. Biol. Chem., 281:3198-3203 (2006).

Huang et al., "Influenza A virus neuraminidase limits viral superinfection," J. Virol., 82:4834-4843 (2008).

International Search Report and Written Opinion issued in PCT/US2010/059934 on Nov. 8, 2011.

Kochs et al., "Multiple Anti-Interferon Actions of the Influenza A Virus NS1 Protein," Journal of Virology, 81, 13, 7011-7021, 2007.

Lamb and Krug, Orthomyxoviridae: The viruses and their replication, 4th edn. Philadelphia, Lippincott Williams and Wilkins (2001).

Lange et al., "The Fragilis interferon-inducible gene family of transmembrane proteins is associated with germ cell specification in mice," BMC Dev Biol., 3:1, 1-11 (2003).

Lange et al., "Normal Germ Line Establishment in Mice Carrying a Deletion of the *Ifitm/Fragilis* Gene Family Cluster," Mol. Cell Biol., 28(15):4688-4696 (2008).

Lewin et al., "Molecular analysis of a human interferon-inducible gene family," Eur. J. Biochem., 199:417-423 (1991).

Li et al., "A genome-wide genetic screen for host factors required for hepatitis C virus propagation," PNAS, 106(38):16410-16415 (2009).

Maines et al., "Pathogenesis of emerging avian influenza viruses in mammals and the host innate immune response," Immunol Rev 225:68-84 (2008).

Makarova et al., "The 65 and 110 kDa SR-related proteins of the U4/U6.U5 tri-snRNP are essential for the assembly of mature spliceosomes," EMBO J., 20:2553-2563 (2001).

Marshansky and Futai, "The V-type H+-ATPase in vesicular trafficking: targeting, regulation and function," Curr. Opin. Cell Biol., 20:415-426 (2008).

Moffatt et al., "Bril: a novel bone-specific modulator of mineralization," J. Bone Miner Res., 23(9):1497-1508 (2008).

Monto, "The risk of seasonal and pandemic influenza: prospects for control," Clin. Infect. Dis., 48 Suppl 1, S20-25 (2009).

Nakhaei et al., "RIG-I-like receptors: sensing and responding to RNA virus infection," Semin Immunol., 21:215-222 (2009).

Rodman and Wandinger-Ness, "Rab GTPases coordinate endocytosis," J. Cell. Sci., 113(Pt2):183-192 (2000).

Ropolo et al., "Cloning of IP15, a pancreatitis-induced gene whose expression inhibits cell growth," Biochem Biophys Res Commun, 319(3):1001-1009 (2004).

Schoggins et al., "Identification of Interferon effectors that inhibit RNA virus replication," p. 31 Northeast Biodefense Center, NIAID Region II center of Excellence for Biodefense and Emerging Infectious Diseases 2009 Annual Meeting Program Book, p. 31 (Nov. 2, 2009).

Sieczkarski and Whittaker, "Differential requirements of Rab5 and Rab7 for endocytosis of influenza and other enveloped viruses," Traffic 4, 333-343 (2003).

Skehel and Wiley, "Influenza viruses and cell membranes," Am J Respir Crit Care Med, 152:S13-15 (1995).

Smith et al., "Expression of the mouse fragilis gene products in immune cells and association with receptor signaling complexes," Genes Immun., 7(2):113-121 (2006).

Stevens et al., "Biochemical and genetic analyses of the U5, U6, and U4/U6 x U5 small nuclear ribonucleoproteins from *Saccharomyces cerevisiae*," RNA 7:1543-1553 (2001).

Tanaka et al., "Regulation of Expression of Mouse Interferon-Induced Transmembrane Protein Like Gene-3, *Ifitm3* (*mil-1, fragilis*), in Germ Cells," *Developmental Cell*, 9:745-756 (2005).

Tanaka et al., "Developmentally regulated expression of *mil-1* and *mil-2*, mouse interferon-induced transmembrane protein like genes, during formation and differentiation of primordial germ cells," Developmental Dynamics, 230:651-659 (2004).

Tanaka et al., "IFITM/Mil/Fragilis Family Proteins IFITM1 and IFITM3 Play Distinct Roles in Mouse Primordial Germ Cell Homing and Repulsion," Mechanisms of Development, 119S:S261-267 (2002).

Tobiume et al., "Nef does not affect the efficiency of human immunodeficiency virus type 1 fusion with target cells," J. Virol., 77(19):10645-10650 (2003).

Tscherne et al., "An enzymatic virus-like particle assay for sensitive detection of virus entry," J. Virol. Methods, 163(2):336-343 (2010).

Yoshi et al., "Sub-genomic replicon and virus-like particles of Omsk hemorrhagic fever virus," Arch. Virol., 154(4):573

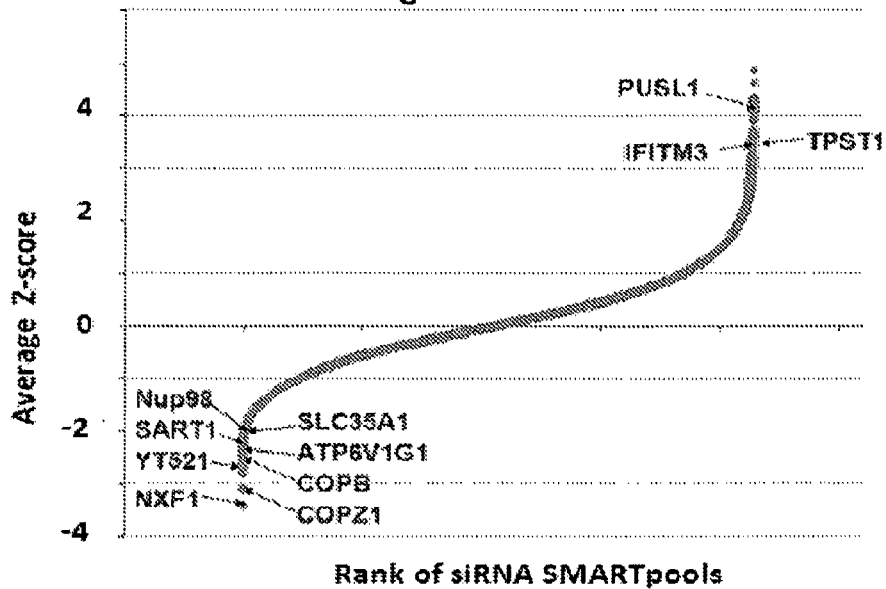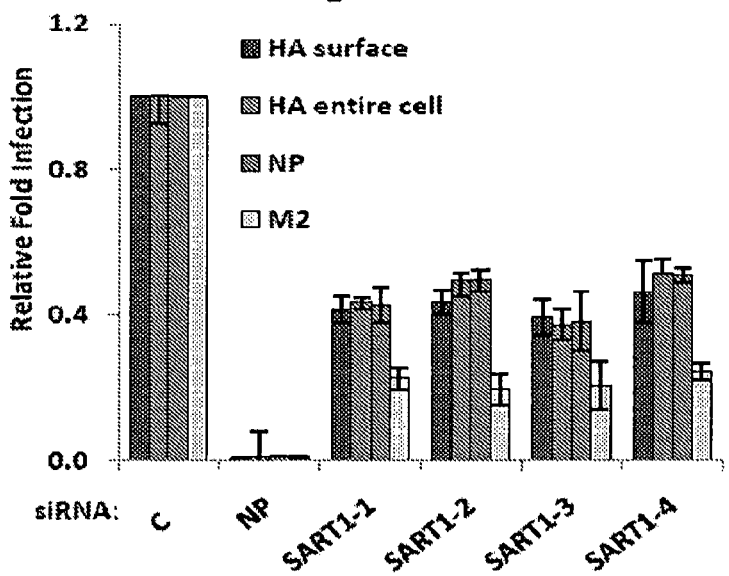

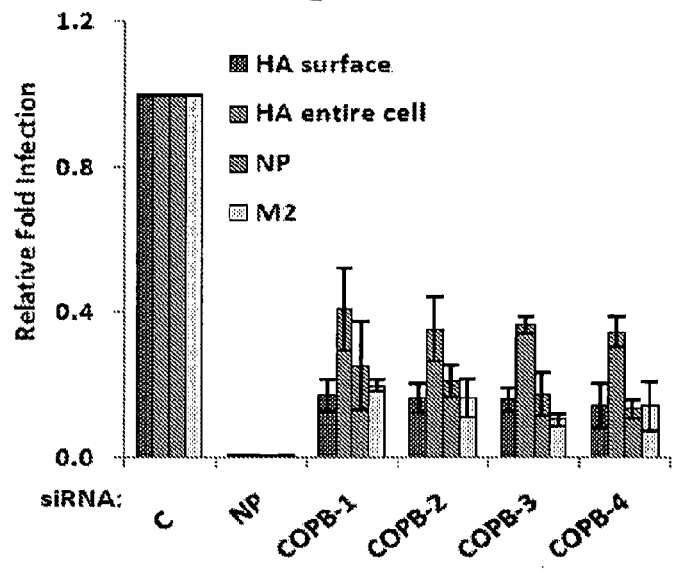
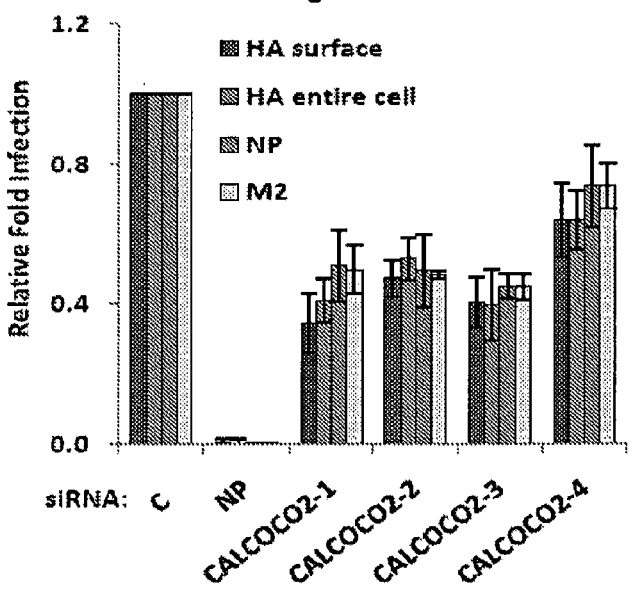

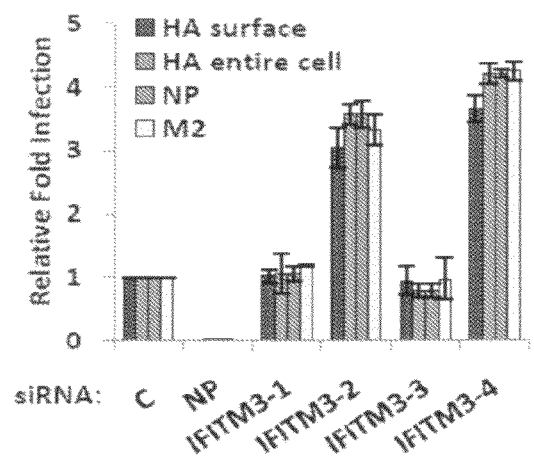
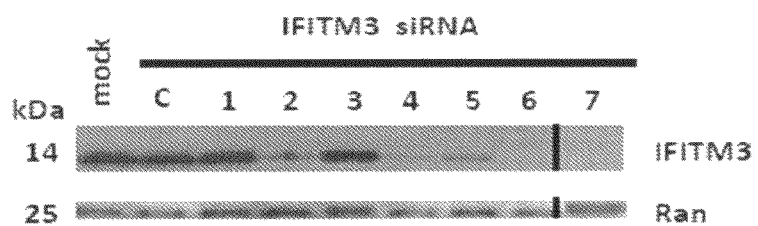

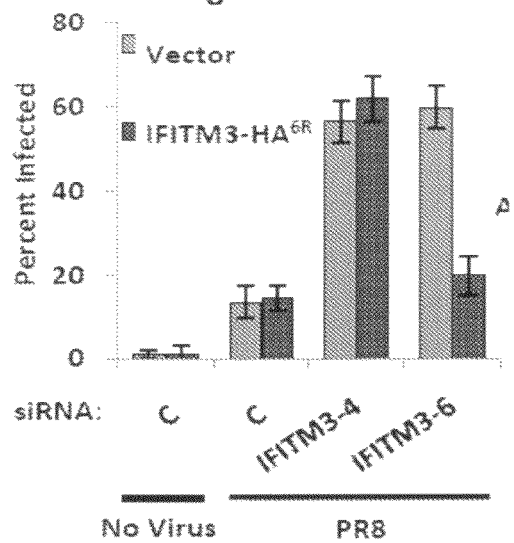
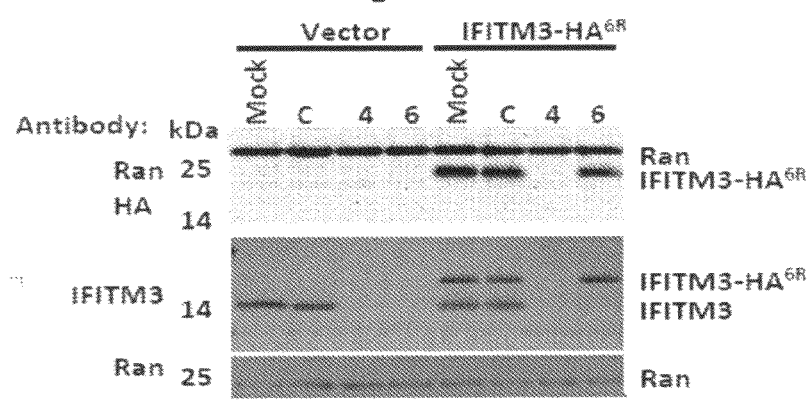
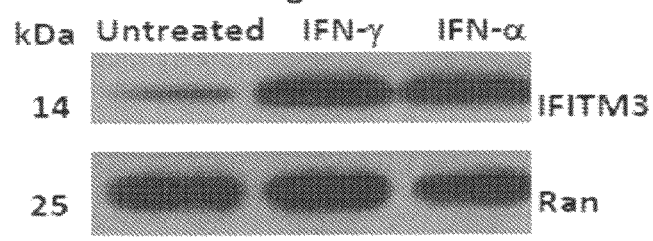

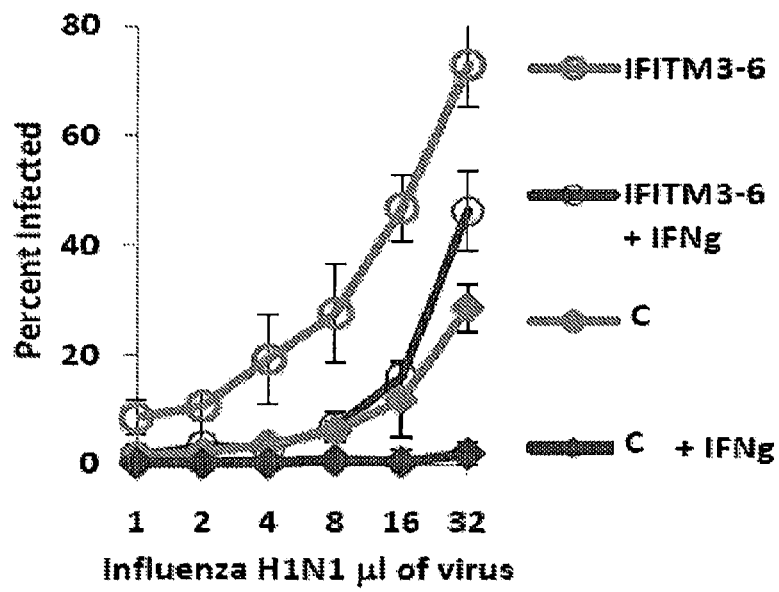
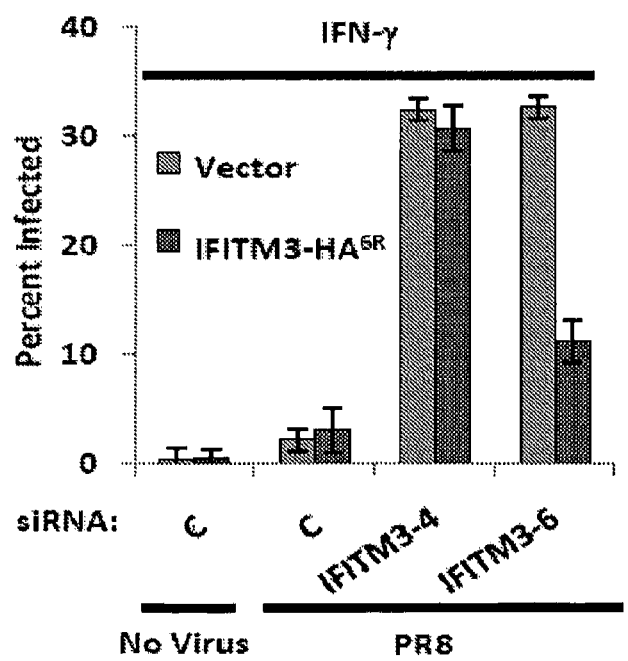

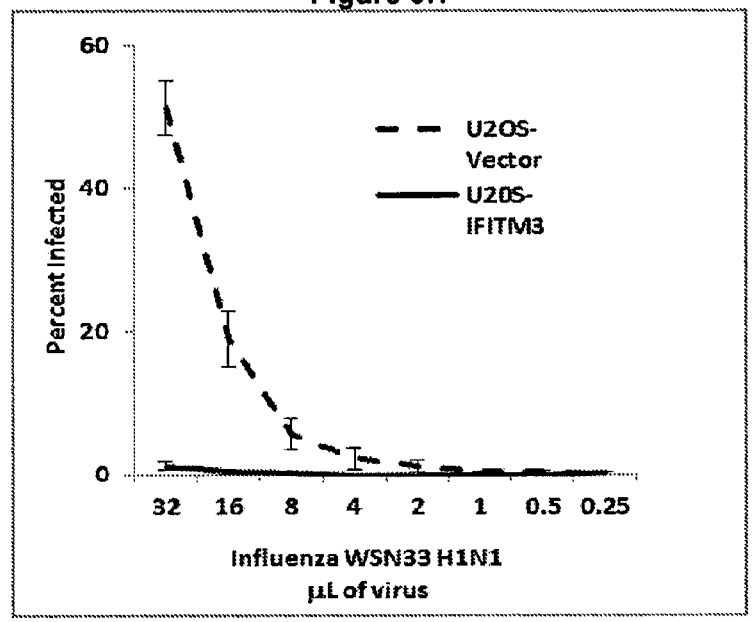
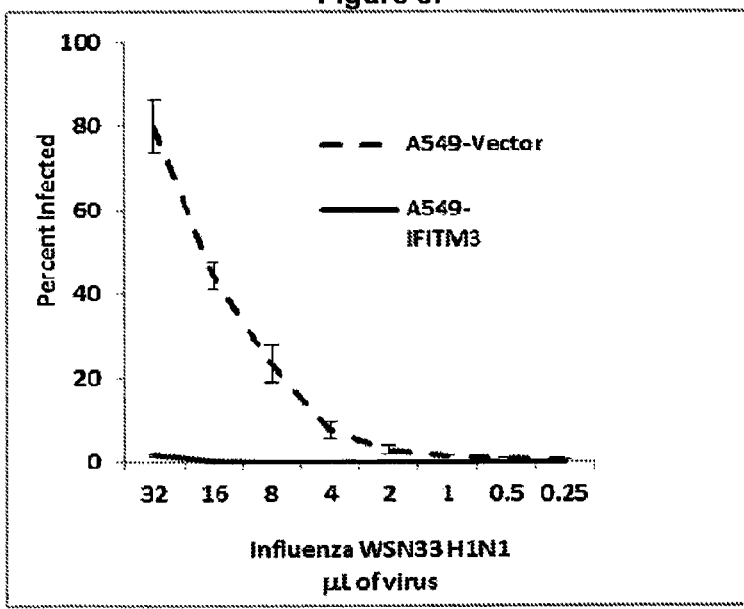

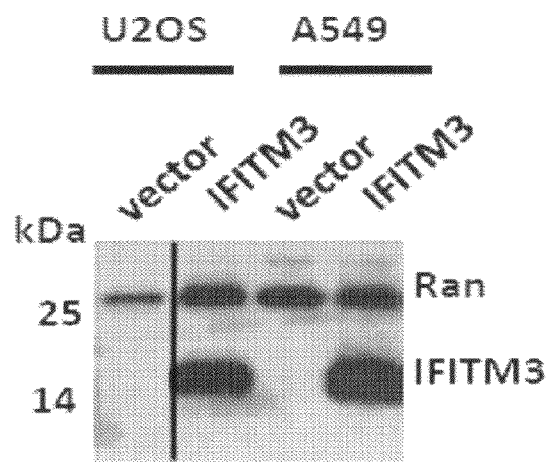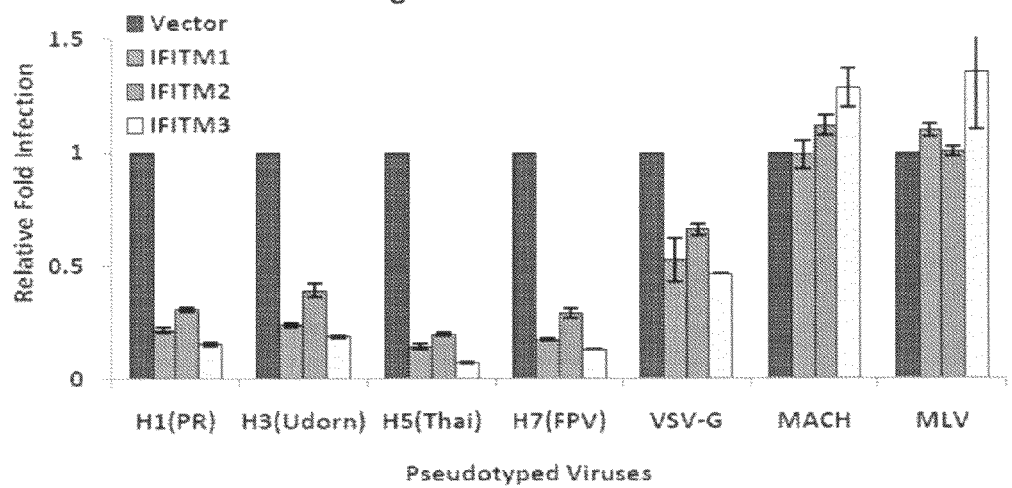

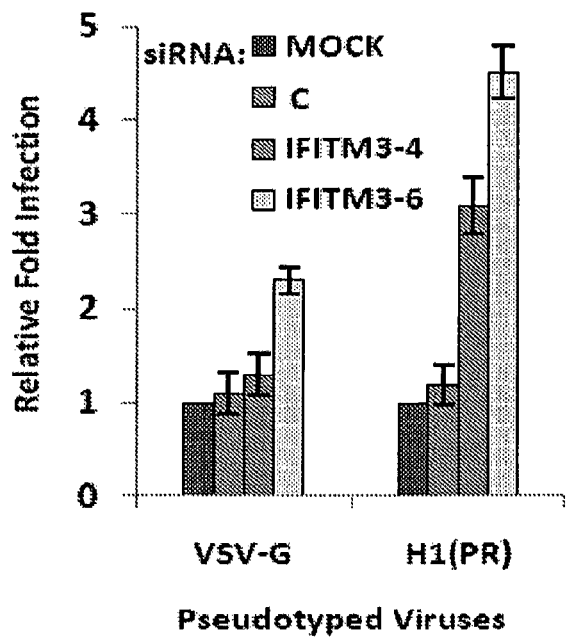
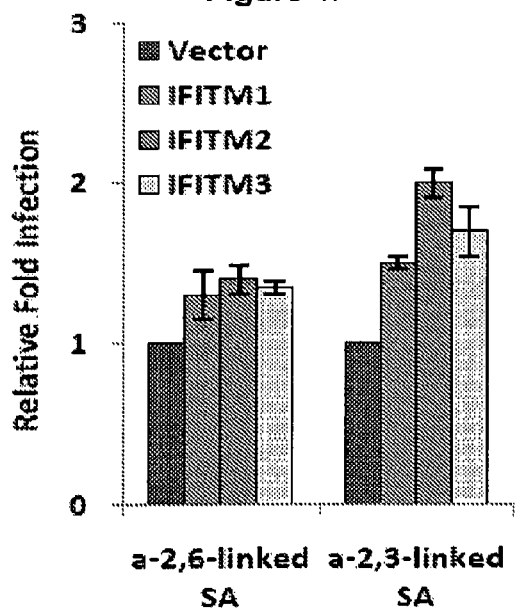

```
Human_IFITM3   MNHTVQTFFSPVNSGQPPNYEMLKEEHEVAVLGAPHNPAPPMSAVIHIRSETSVPDHVVW   60
Human_IFITM2   MNHIVQT-FSPVNSGQPPNYEMLKEEQEVAMLGGPHNPAPPMSTVTHIRSETSVPDHVVW   59
Human_IFITM1   ------------MHKEEHEVAVLGPPHNPAPPMSTILPPSTVINIRSETSVPDHVVW     39
                          * **** ;**; ****   *;*****;************* ********

Human_IFITM3   SLFNTLFMNPCCLGFIAFAYSVKSRDRKMVGDVTGAQAYASTAKCLNIWALILGILMTIL  120
Human_IFITM2   SLFNTLFMNTCCLGFIAFAYSVKSRDRKMVGDVTGAQAYASTAKCLNIWALILGIFMTIL  119
Human_IFITM1   SLFNTLFLNWCCLGFIAFAYSVKSRDRKMVGDVTGAQAYASTAKCLNIWALILGILMTIG   99
               *******;* ************************************ ************  ;***

Human_IFITM3   LIVIPVL-------IFQAYG--  133
Human_IFITM2   LVIIPVL-------VVQRQR--  132
Human_IFITM1   FILLIVFGSVTYHIMLQIIQEKRGY  125
                ;;;;                ;*
```

Figure 4H

WNV

Dengue Virus

Figure 6F

ChEF cells

Figure 9A
*Gallus gallus* IFITM Homologues:

NCBI Reference Sequence: XP_420925.1
PREDICTED: similar to inteferon-induced membrane protein Leu-13/9-27
[Gallus gallus]
>gi|50747606|ref|XP_420925.1| PREDICTED: similar to inteferon-induced
membrane protein Leu-13/9-27 [Gallus gallus]
MQSYPQHTSINMPSYGQDVTTTIPISPQPPPKDFVLWSLFNFVLCNAFCLGL
CALSYSIKSRDRIIAKDFVGASSYGRTAKIFNIFAFCVGLLVTILSIVLVFLYLPL
YTVRP

NCBI Reference Sequence: XP_001233950.1
PREDICTED: hypothetical protein [Gallus gallus]
>gi|118091073|ref|XP_001233950.1| PREDICTED: hypothetical protein
[Gallus gallus]
MFSIVSLDGSGELLPAPGQGWGAPRPSSLLISWPPGASPPPRRAGSGHGR
AANEWSGGGGSGGRGRGAARAERRGRRPIAARRGGVSANRSAAGAEPE
GAPRVATPTGRQPRAGPRGLRGERPRFRPRGVGERGGNAAGGDGAVRVR
EGRRDGGRGTRAARLCAPSPPGTGLSRDRKVLGDYSGALSYGSTAKYLNIT
AHLINVFLIILIIALVASGTIMVANIFNHQQQHPEFIGPT

NCBI Reference Sequence: XP_001234446.1
PREDICTED: similar to 6330512M04Rik protein [Gallus gallus]
>gi|118091315|ref|XP_001234446.1| PREDICTED: similar to 6330512M04Rik
protein [Gallus gallus]
MTTMITKPRRERAGGSGEDAAPCRTEPPPALPGTARPRPPSSPSRDGTDG
TRPGRTDNQRDSRRDGRTEDCGRGQRGERGDAAAAAAATTERTQDPPLG
PPCPFDGAAWAPRPPPGPQQGCFACIAKPPALRHASPVLSPSSAAQLMES
KGCKGDSLRPAGPCKHSVEKKTMTNPTTVIEIYPDTSEVNDYYLWSIFNFVY
LNFCCLGFIALAYSLKVRDKKLLNDLNGAVEDAKTARLFNITSSALATFCIILIFI
FLRYPLTDY

NCBI Reference Sequence: XP_420924.1
PREDICTED: similar to interferon induced transmembrane protein 5 [Gallus
gallus]
>gi|50747604|ref|XP_420924.1| PREDICTED: similar to interferon induced
transmembrane protein 5 [Gallus gallus]
MDTSYPREDYLPMTSHKRDSSPTTATSAPPRDHLIWSIFNTIYMNFCCLGFV
ALAFSVKARDRKVAGDVEAARRFSSKARCYNALATAGSVLLPILLAALVVTG
VLHLSKLAQDSVGFFSSQFSASDDEDK

Figure 9B

CHIMP IFITM Homologs

NCBI Reference Sequence: XP_508190.1
PREDICTED: interferon induced transmembrane protein 2 (1-8D) isoform 9 [Pan troglodytes]
>gi|55635045|ref|XP_508190.1| PREDICTED: interferon induced transmembrane protein 2 (1-8D) isoform 9 [Pan troglodytes]
MNHIVQTFSPVNSGQPPNYEMLKEEQEVAMLGAPHNPAPPMSTVIHIRSET
SVPDHVVWSLFNTLFMNPCCLGFIAFAYSVKSRDRKMVGDVTGAQAYASTA
KCLNIWALILGILMTIGFILLLVFGSVTVYHIMLQIIQEKRGY

NCBI Reference Sequence: XP_001145216.1
PREDICTED: interferon-induced transmembrane protein 3 (1-8U) [Pan troglodytes]
>gi|114635342|ref|XP_001145216.1| PREDICTED: interferon-induced transmembrane protein 3 (1-8U) [Pan troglodytes]
MNHTVQTFFSPVNSGQPPNYEMLKEEHEVAVLGAPHNPAPPMSTVIHIRSE
TSVPDHVVWSLFNTLFMNPCCLGFIAFAYSVKSRDRKMVGDVTGAQAYAST
AKCLNIWALILGILMTILLIVIPVLIFQAYG

NCBI Reference Sequence: XP_001144684.1
PREDICTED: interferon induced transmembrane protein 1 (9-27) isoform 2 [Pan troglodytes]
>gi|114635332|ref|XP_001144684.1| PREDICTED: interferon induced transmembrane protein 1 (9-27) isoform 2 [Pan troglodytes]
MHKEEHEVAVLGAPPSTILPRSTVINIHSETSVPDHVVWSLFNTLFLNWCCL
GFIAFAYSVKSRDRKMVGDVTGAQAYASTAKCLNIWALILGILMTIGFILLLVF
GSVTVYHIMLQIIQEKRGY

Figure 9C
Rainbow trout IFITM homologs

NCBI Reference Sequence: NP_001118085.1
interferon inducible protein [Oncorhynchus mykiss]

>gi|185133018|ref|NP_001118085.1| interferon inducible protein
[Oncorhynchus mykiss]
MDQPPPYQPEFVPMKGNKYMRLEDTHGAPKFQHTVVLGQPQPVVPHPRD
HIIWSLCSLVYCNPFCLGMLAVYFSIKSRDRKMVGDLEGARKHGKTACCFNT
VTLTLAILGLLFFFITYGIIIYQVAH GenBank: CAC85160.1
Interferon Inducible Protein 2 [Oncorhynchus mykiss]

>gi|20160300|emb|CAC85160.1| Interferon Inducible Protein 2
[Oncorhynchus mykiss]
MDQSPSYQPEFVPMNGNKYMRLEDPHGAPKFQHTVVLGLPQPVVPQPRD
HIIWSLCSLVYGNPLCLGMLAVYFSIKSRDRKMVGDLEGARKHGKTARCFNV
VTLTLVILGLLFLFIIYGFFIYNISHL

Figure 9D
Mouse IFITM homologs

NCBI Reference Sequence: NP_079654.1
interferon induced transmembrane protein 3 [Mus musculus]
>gi|21539593|ref|NP_079654.1| interferon induced transmembrane protein 3
[Mus musculus]
MNHTSQAFITAASGGQPPNYERIKEEYEVAEMGAPHGSASVRTTVINMPRE
VSVPDHVVWSLFNTLFMNFCCLGFIAYAYSVKSRDRKMVGDVTGAQAYAST
AKCLNISTLVLSILMVVITIVSVIIIVLNAQNLHT NCBI Reference Sequence: NP_444318.1
interferon induced transmembrane protein 5 [Mus musculus]
>gi|33504579|ref|NP_444318.1| interferon induced transmembrane protein 5
[Mus musculus]
MDTSYPREDPRAPSSRKADAAAHTALSMGTPGPTPRDHMLWSVFSTMYLN
LCCLGFLALVHSVKARDQKMAGNLEAARQYGSKAKCYNILAAMWTLVPPLL
LLGLVVTGALHLSKLAKDSAAFFSTKFDEEDYN NCBI Reference Sequence: NP_001028804.1
interferon induced transmembrane protein 6 [Mus musculus]
>gi|75812952|ref|NP_001028804.1| interferon induced transmembrane
protein 6 [Mus musculus]
MVKRDPDSAPVPSTVVCINSDVIQPDHITWSTFNTVFMNGCCLGFIAYIYSVK
SRDRKMVGDMTGAQSHASTAKILNILALVISLIFYIMLIVLYSFNLLGNQR NCBI Reference Sequence: NP_081096.3
interferon induced transmembrane protein 1 [Mus musculus]
>gi|163310729|ref|NP_081096.3| interferon induced transmembrane protein 1
[Mus musculus]
MPKEQQEVVVLGSPHISTSATATTINMPEISTPDHVVWSLFNTLFMNFCCLG
FVAYAYSVKSRDRKMVGDTTGAQAFASTAKCLNISSLFFTILTAIVVIVVCAIR NCBI Reference Sequence: NP_083244.1
interferon induced transmembrane protein 7 [Mus musculus]
>gi|21539643|ref|NP_083244.1| interferon induced transmembrane protein 7
[Mus musculus]
MPKDQHEVVVMGTPHTSTSSTTTIITMPEISKPDYVVWSLFNTLFMNFCCLG
FIAYAYSVKSRDRKMVGDMTGAQAFASTARCLNISCLILSVVMVILFITFFATR
R

Figure 9E
Macaque IFITM Homologs

NCBI Reference Sequence: XP_001085444.1
PREDICTED: interferon induced transmembrane protein 1 (9-27) [Macaca mulatta]
>gi|109104827|ref|XP_001085444.1| PREDICTED: interferon induced transmembrane protein 1 (9-27) [Macaca mulatta]
MHKEEHEVSVLGAPHSTILPRSTMINIQSETSVPDHIVWSLFNTIFLNWCCLG
FIAFAYSVKSRDRKMVGDVTGAQAYASTAKCLNISALIVGILMTIGFILLLVYG
SVAIYHVMLQIVQEKQRY NCBI Reference Sequence: XP_001085567.1
PREDICTED: interferon induced transmembrane protein 3 (1-8U) [Macaca mulatta]
>gi|109104829|ref|XP_001085567.1| PREDICTED: interferon induced transmembrane protein 3 (1-8U) [Macaca mulatta]
MNHTVQTFFSPVNSGQPPNYEMLKEEHDVAMMGAPHNPAPPTSTVIHIRSE
TSVPDHVVWSLFNTLFMNPCCLGFIAFAYSVKSRDRKMVGDLTGAQAYAST
AKCLNIWALILGILMTILLIVVPVLIFQAHQ

Horse IFITM homologs

NCBI Reference Sequence: XP_001488723.1
PREDICTED: similar to inteferon-induced membrane protein Leu-13/9-27 [Equus caballus]
>gi|149759281|ref|XP_001488723.1| PREDICTED: similar to inteferon-induced membrane protein Leu-13/9-27 [Equus caballus]
MIKEEHEVSVLGAPQSSAPMTTTVINIHSDTSVPDHIVWSLFNTLFMNWCCL
GFVAFAYSVKSRDRKMVGDVTGAQSYASTAKCLNIWALVLGLFLSTGFIVLM
GFTCLTLYQIIVKAMQDGRGYF NCBI Reference Sequence: XP_001488742.1
PREDICTED: similar to interferon-induced transmembrane protein 3 (1-8U) [Equus caballus]
>gi|149759254|ref|XP_001488742.1| PREDICTED: similar to interferon-induced transmembrane protein 3 (1-8U) [Equus caballus]
MNRSFQTFVSGAHTGVPPTYEMLKEEHEVSVLGALRSSAPVTTTVINIHSDT
SVPDHIVWSLFNTLFTYWCCCLGFVAFAYSVKSRDRKMEGDVTGAQSYAST
AKCLNIAALVMGLLVIITFFIISCLWLTDLFPHILAIIMSSRDY

Figure 9F
Rat IFITM homologs

NCBI Reference Sequence: NP_001129596.1
interferon induced transmembrane protein 3 [Rattus norvegicus]
>gi|209915621|ref|NP_001129596.1| interferon induced transmembrane protein 3 [Rattus norvegicus]
MNHTSQAFVNAATGGQPPNYERIKEEYEVSELGAPHGSASVRTTVINMPRE
VSVPDHVVWSLFNTLFMNFCCLGFIAYAYSVKSRDRKMVGDMTGAQAYAS
TAKCLNISSLVLSILMVIITIVTVVIIALNAPRLQT

NCBI Reference Sequence: NP_110460.1
interferon induced transmembrane protein 2 [Rattus norvegicus]
>gi|13540634|ref|NP_110460.1| interferon induced transmembrane protein 2 [Rattus norvegicus]
MSHNSQAFLPANAGLPPSYETIKEEYGVTELGEPNNSAVVRTTVINMPREVS
VPDHVVWSLFNTLFFNACCLGFIAYAYSVKSRDRKMVGDVIGAQAYASTAK
CLNISSLIFSVLMVIICIIIFSTTSAVVFQSLSQRTP
HSGF

NCBI Reference Sequence: NP_001099784.1
interferon induced transmembrane protein 1 [Rattus norvegicus]
>gi|157821317|ref|NP_001099784.1| interferon induced transmembrane protein 1 [Rattus norvegicus]
MPKEQQEVVILGGPHTSNSATTTTINMPAEISTPDHVVWSLFNTLFMNFCCL
GFIAYSYSVKSRDRKMVG
DVTGAKTYASTAKCLNISSVIFTILMAILTIILYATKRT

Figure 9G
Cow IFITM homologs

NCBI Reference Sequence: XP_001253014.1
PREDICTED: similar to interferon-induced protein 1-8U [Bos taurus]
>gi|119919513|ref|XP_001253014.1| PREDICTED: similar to interferon-induced protein 1-8U [Bos taurus]
MNRTSQLLLTGAHGAVPPAYEVLKEEHEVAVLGAPQSQAPLTTTVINIRSDT
AVPDHIVWSLFNTIFMNWCCLGFVAFAYSVKSRDRKMVGDITGAQSYASTA
KCLNICSLVLGILLTVVLIVLVSTGSLMIVQAVSELMQNYGGH

NCBI Reference Sequence: NP_001071610.1
interferon-induced transmembrane protein 1 (9-27) isoform 1 [Bos taurus]
>gi|118151350|ref|NP_001071610.1| interferon-induced transmembrane protein 1 (9-27) isoform 1 [Bos taurus]
MIKEEHEVAVLGAPQSQAPLTTTVINIRSDTAVPDHIVWSLFNTIFLNWCCLG
FVAFAYSVKSRDRKMVGDITGAQSYASTAKCLNIWALVLGIFLTIGSIVLLIFVY
MAAYETALRISRHGGH

NCBI Reference Sequence: NP_001071522.1
interferon induced transmembrane protein 2 (1-8D) [Bos taurus]
>gi|118151192|ref|NP_001071522.1| interferon induced transmembrane protein 2 (1-8D) [Bos taurus]
MLKEENEVAVLGAPQSQAPVTTTVINIPRENSVPDHIVWSLFNTVFLNWCCL
GFVAFAYSVKSRDRKMVGDITGAQSYASTAKCLNIWALVLGIFLTIGSIVLLIF
VYMAAYETALRISRHGGH

Figure 9H

Human IFITM1, 2 and 3

NCBI Reference Sequence: NP_066362.2
interferon-induced transmembrane protein 3 (1-8U) [Homo sapiens]

>gi|148612842|ref|NP_066362.2| interferon-induced transmembrane protein 3 (1-8U) [Homo sapiens]
MNHTVQTFFSPVNSGQPPNYEMLKEEHEVAVLGAPHNPAPPTSTVIHIRSET
SVPDHVVWSLFNTLFMNPCCLGFIAFAYSVKSRDRKMVGDVTGAQAYASTA
KCLNIWALILGILMTILLIVIPVLIFQAYG

NCBI Reference Sequence: NP_006426.2 interferon induced transmembrane protein 2 (1-8D) [Homo sapiens]
>gi|151101191| | interferon induced transmembrane protein 2 (1-8D)
MNHIVQTFSPVNSGQPPNYEMLKEEQEVAMLGVPHNPAPPMSTVIHIRSET
SVPDHVVWSLFNTLFMNTCCLGFIAFAYSVKSRDRKMVGDVTGAQAYASTA
KCLNIWALILGIFMTILLIIIPVLVVQAQR

NCBI Reference Sequence: NP_003632.3 interferon induced transmembrane protein 1 (9-27) [Homo sapiens]
>gi|150010589|ref|NP_003632.3| interferon induced transmembrane protein 1 (9-27) [Homo sapiens]
MHKEEHEVAVLGAPPSTILPRSTVINIHSETSVPDHVVWSLFNTLFLNWCCL
GFIAFAYSVKSRDRKMVGDVTGAQAYASTAKCLNIWALILGILMTIGFILLLVF
GSVTVYHIMLQIIQEKRGY

NCBI Reference Sequence: NP_001020466.1  interferon induced transmembrane protein 5 [Homo sapiens]

>gi|70608168|ref|NP_001020466.1| interferon induced transmembrane protein 5 [Homo sapiens]
MDTAYPREDTRAPTPSKAGAHTALTLGAPHPPPRDHLIWSVFSTLYLNLCCL
GFLALAYSIKARDQKVVG
DLEAARRFGSKAKCYNILAAMWTLVPPLLLLGLVVTGALHLARLAKDSAAFF
STKFDDADYD

Figure 10

Influenza A Virus H1N1 NS1 Alignment

```
A/WSN/1933          MDPNTVSSFQVDCFLWHVRKRVADQELGDAPFLDRLRRDQKSLRGRGSTL  50
A/WS/1933           MDPNTVSSFQVDCFLWHVRKRVADQELGDAPFLDRLRRDQKSLRGRGSTL  50
A/Puerto/1936       MDPNTVSSFQVTCFLWHVRKRVADQELGDAPFLDRLRRDQKSLRGRGSTL  50
A/Brevig_Mission/1/18  MDSNTVSSFQVDCYLWHVRKRFADQELGDAPFLDRLRRDQKSLRGRGSTL  50
A/Udorn/72          MDSNTVSSFQVDCYLWHVRKQVVDQELQDAPFLDRLRRDQKSLRGRGSTL  50
                    **.:********.*:******: ::**:*:********************

A/WSN/1933          GLDIETATRAGKQIVERILKEESDEALKMTMASVPASRYLTDMTLEEMSR 100
A/WS/1933           GLDIETATRAGKQIVERILKEESDEALKMTMASVPASRYLTDMTLEEMSR 100
A/Puerto/1936       GLDIRATATRAGKQIVERILKEESDEALKMTMASVPASRYLTDMTLEEMSR 100
A/Brevig_Mission/1/18  GLDIKTATHVGKQIVERILEEESDEALKMTIASVESASRYLTMAESPASRYITDMTLEELSR 100
A/Udorn/72          GLNIEMATHVGKQIVERILKEESDEALKMTMASTPASRYITDMTEELSR 100
                    **:*  **: :***:*****:*************:****:  :**::**

A/WSN/1933          HWFMLMPKQKVAGPLCIRMDQAIMDKNIILKANFSVIFDRLETLILLRAF 150
A/WS/1933           HWFMLMPKQKVAGPLCIRMDQAIMDKNIILKANFSVIFDRLETLILLRAF 150
A/Puerto/1936       DWSLIIPKQKVAGPLCIRMDQAIMDKNIILKANFSVIFDRLETLILLRAF 150
A/Brevig_Mission/1/18  DWFMLMPKQKVAGSLCIRIDQAIMDKNIILKANFSVIFDRLETLILLRAF 150
A/Udorn/72          DWFNLMPKQKVEGPLCIRIDQAIMDKNIMLKANFSVIFDRLETLILLRAF 150
                    .* ::: ***** ::****:*************** ************

A/WSN/1933          TEEGAIVGEISPLPSLPGHTDEDVKNAVGVLIGGLEWNDNTVRVSETLQR 200
A/WS/1933           TEEGAIVGEISPLPSLPGHTDEDVKNAVGVLIGGLEWNDNTVRVSETLQR 200
A/Puerto/1936       TEEGAIVGEISPLPSLPGHTAEDVKNAVGVLIGGLEWNDNSVRVSETLQR 200
A/Brevig_Mission/1/18  TEEGAIVGEISPLPSLPSHTEDSGHTIEDVKMATGVLIGGLEWNDNTVKSKLQR 200
A/Udorn/72          TEEGAIVGEISPLPSLPGHTNEDVKNAVGVLIGGLEWNKNFVKVSETLQR 200
                    *******:********.** :*  .**:*****:***.  .:...:**

A/WSN/1933          RAWRSSNENGRPLTPKQKREMAGTIRSEV------ 230
A/WS/1933           RAWRSSNENGRPLTPKQKREMAGTIRSEV------ 230
A/Puerto/1936       RAWRSSNENGRPLTPKQKREMAGTIRSEV------ 230
A/Brevig_Mission/1/18  PAWRSSMENGRPLFPNQKEKMARCTKSEV------ 230
A/Udorn/72          PAWRSSNENGRPLFPSQKRRMARTARSKVERSRKAD 237
                    ***:***:*****:*.:*::**  : :..
```

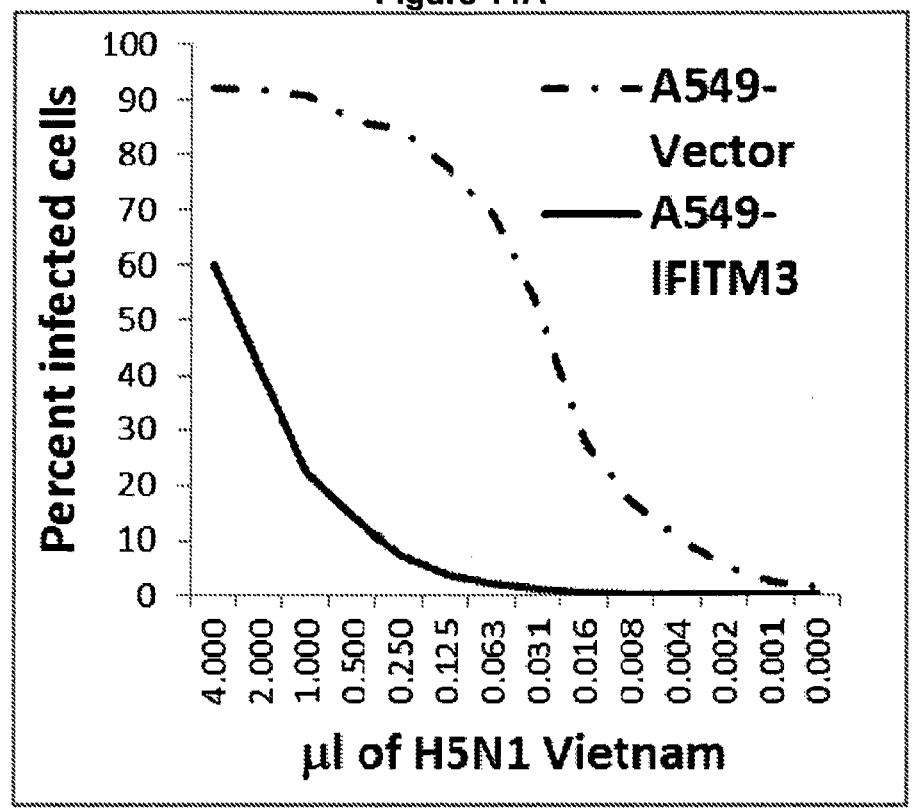

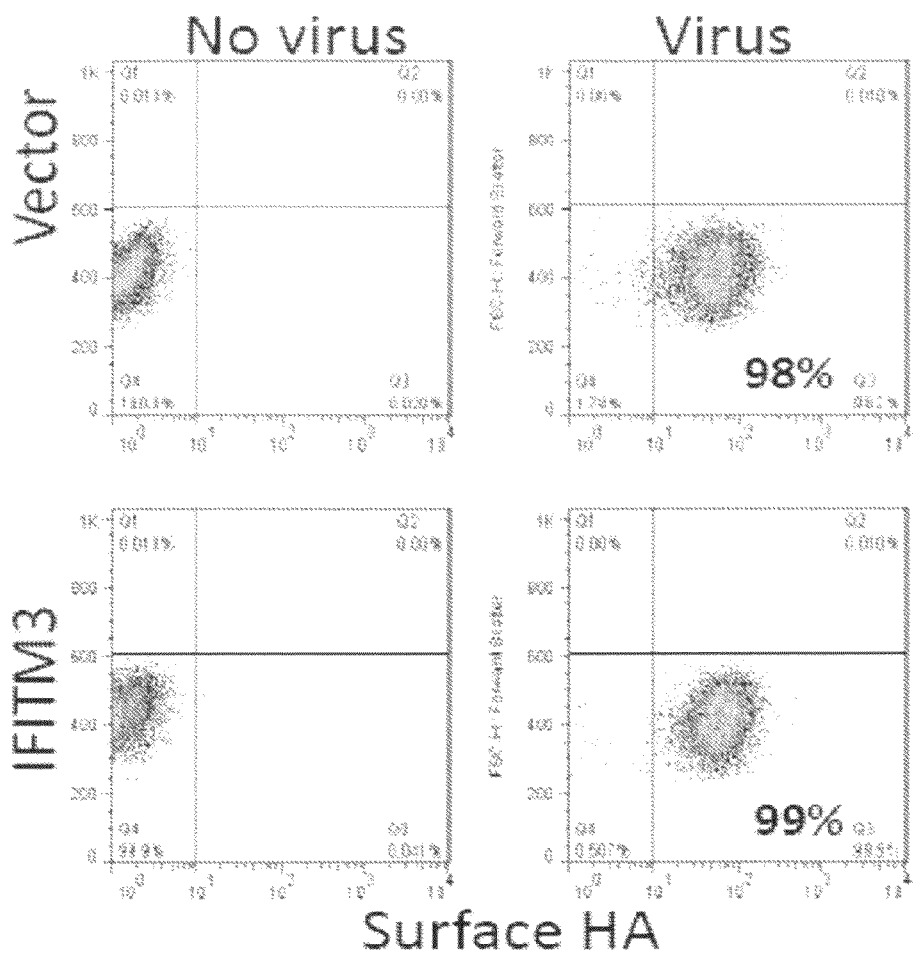

Figure 15 mnhtvqtffs pvnsgqppny emlkeeheva vlgaphnpap
ptstvihirs etsvpdhvvw slfntlfmnp cclgfiafay
svksrdrkmv gdvtgaqaya stakclniwa lilgilmtil
livipvlifq ayg  (SEQ ID NO:611)

Figure 16 mnhivqtfsp vnsgqppnye mlkeeqevam lgvphnpapp
mstvihirse tsvpdhvvws lfntlfmntc clgfiafays
vksrdrkmvg dvtgaqayas takclniwal ilgifmtill
iiipvlvvqa qr  (SEQ ID NO:612)

Figure 17 mhkeehevav lgappstilp rstvinihse tsvpdhvvws
lfntlflnwc clgfiafays vksrdrkmvg dvtgaqayas
takclniwal ilgilmtigf illlvfgsvt vyhimlqiiq
ekrgy  (SEQ ID NO:613)

PATHOGEN RESTRICTION FACTORS

CLAIM OF PRIORITY

The present application is a 371 of international application no. PCT/US2010/059934, filed Dec. 10, 2010, which claims the benefit of the filing date of U.S. Patent Application Ser. No. 61/285,817, filed on Dec. 11, 2009, the entire contents of which are incorporated by reference herein.

TECHNICAL FIELD

This invention relates to the use of Interferon Induced Trans-membrane Proteins (IFITM proteins) as pathogen restriction factors for numerous viruses and other intracellular pathogens, e.g., to inhibit infection by those pathogens, methods of using the same to produce the pathogens, and transgenic animals expressing exogenous IFITMs, e.g., IFITM1, 2, and 3.

BACKGROUND

Influenza epidemics exact a formidable toll on world health. Moreover, viral super-infections can produce antigenic shifting, resulting in more virulent pathogens (Monto, Clin Infect Dis 48 Suppl 1, S20-25, 2009). At present, the emergence of a novel influenza A H1N1 viral strain has created a pandemic, producing illness in over 70 countries. Additionally, the related avian influenza A viral strain, H5N1, represents a potentially catastrophic global health risk (Maines et al., Clin Infect Dis 48 Suppl 1, 520-25, 2008).

The influenza A viral genome encodes for 11 proteins and consists of eight segments of negative single-stranded RNA (Lamb and Krug, Orthomyxoviridae: The viruses and their replication., 4th edn, Philadelphia, Lippincott Williams and Wilkins, 2001). Each sub-genomic segment is coated by viral nucleoprotein (NP) and bound to a single viral RNA-dependent RNA-polymerase holoenzyme (RdRp), composed of PA, PB1 and PB2 subunits. Infection begins with the binding of the viral hemagglutinin (HA) protein to sialyated host cell surface glycoproteins (Chu and Whittaker, Proc Natl Acad Sci USA 101, 18153-18158, 2004; Skehel and Wiley, Am J Respir Crit. Care Med 152, S13-15, 1995). Following endocytosis, viral particles are trafficked through both early and late endosomes, with the intense acidification of the latter compartment altering the conformation of HA, leading to host-viral membrane fusion, and entry of the vRNPs into the cytosol (Sieczkarski and Whittaker, Traffic 4, 333-343, 2003). Nuclear localization signal sequences contained in NP, PB1 and/or PB2 are then bound by host cell karyopherins, and the vRNPs are transported though the nuclear pore complex (NPC, (Boulo et al., Virus Res 124, 12-21, 2007)).

Once in the nucleus, the RdRp commandeers 5' caps from host mRNAs to prime transcription of viral mRNA (vmRNA, (Bouloy et al., Proc Natl Acad Sci USA 75, 4886-4890, 1978) (Engelhardt and Fodor, Rev Med Virol 16, 329-345, 2006)). After producing sufficient vmRNAs, the RdRp creates a positive sense template (cDNA), from which it synthesizes new viral genomes (vRNAs). The vRNAs are coated by NP and exported though the NPC by the viral factors M1 and NEP/NS2 (nuclear export protein) working in concert with the host nuclear export machinery. The viral envelope proteins HA, M2 and neuraminidase (NA) are translated on the rough endoplasmic reticulum (ER) and trafficked to the cell surface where they, along with the soluble factors M1, RdRp and eight distinct vRNPs, are packaged into budding virions.

To defend against this exploitation, the host mobilizes factors to confront the virus. IFNs orchestrate a large component of this anti-viral response, at both a cellular and organismal level (Grandvaux et al., Curr Opin Infect Dis 15, 259-267, 2002). To this end, over 2000 gene products are differentially regulated after IFN stimulation, including the important downstream anti-viral effectors MxA, PKR, RIG-I, and 2'S'-OAS (Grandvaux et al., Curr Opin Infect Dis 15, 259-267, 2002; Haller et al., Rev Sci Tech 28, 219-231., 2009; Nakhaei et al., Semin Immunol 21, 215-222, 2009). However, many viruses deploy anti-IFN countermeasures, which for influenza A virus are primarily enacted by the viral protein, NS1 (Hale et al., J Gen Virol 89, 2359-2376, 2008).

SUMMARY

The present invention is based, at least in part, on the discovery that IFITM1, 2 and 3 are viral restriction factors, i.e., host cell proteins that inhibit viral replication.

Thus in one aspect the invention provides isolated cells that have been engineered to specifically disrupt or reduce expression of an interferon induced transmembrane protein 1, 2, or 3 (IFITM1, 2, or 3) protein. The cells are more susceptible to infection with a virus, parasite, or bacterium, or to a bacterial toxin, that is endocytosed, than a wild-type cell of the same type having normal expression of the IFITM1, 2, or 3. In some embodiments, the cell is infected with a virus, parasite or bacterium.

In some embodiments, the virus is selected from the group consisting of orthomyxoviruses, flaviviruses, Hepadnaviruses, Hepeviruses, Picornaviridae, and retroviruses. In some embodiments, the virus is selected from the group consisting of RNA viruses, and DNA viruses. In some embodiments, the bacterium, parasite, or toxin is selected from the group consisting of Gram-negative bacteria; Gram-positive bacteria; fungi; protozoa; and bacterial toxins.

In some embodiments, the cell is a human cell, such as PER.C6, or HEK293 cell, a non-human mammalian cell (such as African green monkey kidney (Vero or COS cells), Chinese hamster ovary cells (CHO), or Madin-Darby canine kidney (MDCK) cells), a transformed or primary chicken cell, or an avian embryonated egg cell (such as from a chicken). The cells can also be stem cells.

In some embodiments, the cell is a mammalian cell, e.g., a human cell, and the cell has been engineered to specifically disrupt or reduce expression of one or both of IFITM2 and IFITM3. In some embodiments, the cell is a bird cell or a pig cell, and the cell has been engineered to specifically disrupt or reduce expression of IFITM1.

In some embodiments, the IFITM protein is at least 95% identical to NCBI Reference Sequence: NP_066362.2 interferon-induced transmembrane protein 3 (1-8U) [*Homo sapiens*] (SEQ ID NO:598), NCBI Reference Sequence: NP_006426.2 interferon induced transmembrane protein 2 (1-8D) [*Homo sapiens*] (SEQ ID NO:599), or NCBI Reference Sequence: NP_003632.3 interferon induced transmembrane protein 1 (9-27) [*Homo sapiens*] (SEQ ID NO:600).

In another aspect, the invention provides methods for producing a virus, parasite, bacterium, or toxin. The methods include obtaining a host cell that has been engineered to specifically disrupt or reduce expression of a pathogen restriction factor, e.g., a viral restriction factor, e.g., an interferon induced transmembrane protein 1, 2, or 3 (IFITM1, 2, or 3), PULS1, TPST1, or WDR33, e.g., a host cell as described herein; infecting the host cell with the virus, parasite, or bacterium; maintaining the host cell under conditions sufficient for the virus or bacterium to be produced, and isolating the virus or bacterium produced by the cell.

In some embodiments, the host cell is an isolated host cell, and the host cell is maintained in media, and the virus, parasite, bacterium, or toxin is isolated from the host cell or the media.

In some embodiments, the pathogen is a virus.

In a further aspect, the invention provides transgenic animals, the nucleated cells of which comprise a transgene encoding IFITM1, 2, or 3, wherein the animals exhibit a decreased susceptibility to viral infection as compared to a wildtype animal. In some embodiments, the animal is a pig, chicken, duck, or turkey.

In yet an additional aspect, the invention provides methods for treating or reducing risk of a viral or bacterial infection in a subject. The methods include administering to the subject a therapeutically effective amount of a composition comprising an IFITM1, 2, or 3 protein, in a physiologically acceptable carrier that promotes incorporation of the IFITM1, 2, or 3 protein into the membrane of cells of the subject. In some embodiments, the composition includes the IFITM1, 2, or 3 protein incorporated into a liposomal preparation. In some embodiments, the IFITM protein is at least 95% identical to NCBI Reference Sequence: NP_066362.2 interferon-induced transmembrane protein 3 (1-8U) [*Homo sapiens*] (SEQ ID NO:598), NCBI Reference Sequence: NP_006426.2 interferon induced transmembrane protein 2 (1-8D) [*Homo sapiens*] (SEQ ID NO:599), or NCBI Reference Sequence: NP_003632.3 interferon induced transmembrane protein 1 (9-27) [*Homo sapiens*] (SEQ ID NO:600).

In another aspect, the invention features methods for identifying a candidate compound that modulates viral infection. The methods include selecting a target gene from Table 1 or Table 2; providing a sample comprising the target gene, e.g., a cell expressing the target gene; contacting the sample with a test compound; and evaluating expression or activity of the target gene in the presence of the test compound. A test compound that modulates, e.g., increases or decreases, expression or activity of the target gene in the presence of the test compound as compared to expression or activity of the target gene in the absence of the test compound is a candidate compound that modulates viral infection.

In some embodiments, a test compound that decreases expression of a gene listed in Table 1, or increases expression of a gene listed in Table 2, is a candidate compound for decreasing or inhibiting viral infection, whereas a test compound that increases expression of a gene listed in Table 1, or decreases expression of a gene listed in Table 2, is a candidate compound for increasing or promoting viral infection.

In some embodiments, the methods further include selecting a candidate compound that decreases expression of a gene listed in Table 1, or increases expression of a gene listed in Table 2: providing a cell or animal model of an infection, e.g., a viral infection, e.g., infection with influenza A; and detecting an effect of the candidate compound on infection in the cell or animal model. A candidate compound that decreases or inhibits infection in the cell or animal model is a candidate therapeutic compound for the treatment of the infection.

In another aspect, the invention features methods for treating or inhibiting a viral infection in a subject or a cell. The methods include administering to the subject or cell a composition comprising an inhibitor of a gene or protein listed in Table 1. In some embodiments, the inhibitor is an siRNA that specifically decreases expression of a gene listed in Table 1, e.g., an siRNA listed in Table 1.

In another aspect, the invention provides animals, e.g., a population of non-human animals, possessing a functionally deleted form of a gene set forth in Table 2, wherein the population is more susceptible to infection by a pathogen.

In another aspect, the invention provides animals, e.g., a population of non-human animals possessing a functionally deleted form of a gene set forth in Table 1, wherein the population is less susceptible to infection by a pathogen.

In another aspect, the invention features methods for identifying a compound that binds to a gene product set forth in Table 1 or Table 2 and can decrease infection of a cell by a pathogen. The methods include contacting a compound with a gene product set forth in Table 1 or 2; detecting binding of the compound to the gene product; and associating binding with a decrease in infection by the pathogen.

In some embodiments, the methods also include optimizing a compound that binds the gene product in an assay that determines the functional ability to decrease infection, e.g., a cell based assay or an in vivo assay.

In yet an additional aspect, the invention provides methods for identifying an agent that decreases infection of a cell by a pathogen. The methods include administering the agent to a cell containing a cellular gene encoding a gene product set forth in Table 1; detecting the level and/or activity of the gene product produced by the cellular gene, a decrease or elimination of the gene product and/or gene product activity indicating an agent with antipathogenic activity.

In some embodiments, the activity is binding between a gene product set forth in Table 1 and another cellular protein or binding between a gene product set forth in Table 1 and a pathogenic (i.e., non-host) protein.

In another aspect, the invention features methods for identifying an agent that decreases infection in a cell by a pathogen. The methods include administering the agent to a cell containing a cellular gene encoding a gene product set forth in Table 1; contacting the cell with a pathogen; and determining the level of infection, a decrease or elimination of infection indicating that the agent is an agent that decreases infection.

In some embodiments, the methods include measuring the level of expression and/or activity of the gene product. In some embodiments, the level of infection is determined by determining the level of replication of the pathogen. In some embodiments, the pathogen is a virus.

In a further aspect, the invention features methods for inhibiting infection in a cell by a pathogen comprising decreasing expression or activity of a gene or gene product set forth in Table 1. In some embodiments, the infection is decreased by decreasing the replication of the pathogen.

In some embodiments, the pathogen is a virus.

In some embodiments, expression or activity of the gene or gene product is decreased by contacting the cell with a composition comprising a chemical, a compound, a small molecule, an aptamer, a drug, a protein, a cDNA, an antibody, a morpholino, a triple helix molecule, an siRNA, LNA, an shRNAs, an antisense nucleic acid or a ribozyme. In some embodiments, decreasing expression comprises decreasing translation of an mRNA encoding the gene product set forth in Table 1.

In some embodiments, the composition comprises an antisense nucleic acid that specifically hybridizes and decreases expression or activity of the gene product, e.g., an siRNA that decreases expression or activity of the gene product. In some embodiments, the composition comprises an antibody that specifically binds to a protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3A is a bar graph showing relative fold induction in U2OS cells transfected with the indicated siRNAs for 72 hours, then infected with PR8. Infection was assessed by IF for HA (surface or entire cell), NP or M2, 12 hours after viral addition. Relative fold infection is normalized to non-targeting (C) control.

FIG. 3B shows results of U2OS cells transfected with the indicated siRNAs and assessed for IFITM3 levels by Western blotting.

FIG. 3C is a bar graph showing changes in percent infection when U2OS cells stably expressing either IFITM3 with a C-terminal HA-epitope tag (IFITM3-HA$^{6R}$) lacking the target site for siRNA IFITM3-6, or the vector alone, were transfected with the indicated siRNAs (x-axis). After 72 hours the cells were incubated without (no virus) or with influenza A (PR8) for 12 hours, then stained for HA expression. The anti-hemagglutinin antibody used to detect flu infection does not recognize the HA epitope tag on IFITM3-HA$^{6R}$ (no virus, uninfected control).

FIG. 3D is an image of a Western blot showing U2Os cells stably expressing either IFTIM3-HA$^{6R}$ or the vector alone were transfected with the indicated siRNAs and assessed 72 hours after transfection with the antibodies indicated in the left column.

FIG. 3E is an image of a Western blot showing U2OS cells that were untreated, or incubated with either IFN-γ, or IFN-α. After 24 hours the levels of IFITM3 were assessed.

FIG. 3F is a line graph showing percent infection in U2OS cells transfected with the indicated siRNAs, then left untreated or incubated with IFN-γ 48 hours later. After 24 hours of IFN incubation, the cells were infected with increasing amounts of PR8. Twelve hours after infection the cells were stained for HA expression and assessed by IF.

FIG. 3G is a bar graph showing that IFITM3 is required for the anti-viral effect of IFN-γ. U2OS cells stably expressing either IFITM3$^{6R}$ or the vector, were transfected with the indicated siRNAs (x-axis) and treated with interferon-γ 48 hours later. After 24 hours, the cells were incubated without (no virus) or with influenza A (PR8). Twelve hours after infection the cells were checked for HA surface expression by IF. Values represent the mean±SD, N=3. C, Non-targeting siRNA negative control.

FIGS. 3H and 3I are line graphs showing U2OS (3H) and A549 (3I) cells stably overexpressing IFITM3, or an empty vector control. Cells were challenged with WSN/33 influenza A viral strain for 12 hours, then stained for HA expression. Percent infection+/−SD, N=3.

FIG. 4C is an image showing the results of Western blot analysis of IFITM3 expression in A549 and U2OS cells stably over-expressing IFITM3.

FIG. 4D is a bar graph showing changes in relative fold infection in A549 cells transduced with retroviruses containing the indicated IFITM proteins, or the empty viral vector (vector). Two days later the cells were incubated with MLV-EGFP virus pseudotyped with the indicated envelope proteins. H1 (PR): influenza A virus PR8, H3 (Udorn): H1N1 A/Udorn/72, H5(That): A/Thailand2(SP-33)/2004, H7(FPV): A/FPV/Rostak/34, VSV-G, MLV: MLV amphotropic receptor, or MACV: Machupo virus. Viral entry is expressed as mean EGFP fluorescence relative to vector control cells, as measured by flow cytometry. Values represent the mean±SD, N=3.

FIG. 4E is a bar graph showing changes in relative fold infection in U2OS cells transfected with the indicated siRNAs for 72 hours, and then incubated with MLV-GFP virus pseudotyped with the VSV-G or the HA protein of PR8, H1(PR). Entry, represented as percent green fluorescing cells relative to mock-transfected cells, was determined by IF microscopy two days post-infection. Values represent the mean±SD, N=4. C, Non-targeting siRNA negative control.

FIG. 4F is a bar graph showing changes in relative fold infection in A549 cells transduced with the indicated retroviruses. 48 hours later, the cells were tested for surface sialyated glycoproteins. SA: sialic acid. Values represent the mean±SD, N=3.

FIG. 4H shows human IFITM1 (SEQ ID NO: 602), 2 (SEQ ID NO: 601) and 3 (SEQ ID NO: 598) protein sequence alignment. The two transmembrane domains as predicted by UnitprotKB, are shown in bold and underlined. The alignment was performed with ClustalIW. * identical aa, : conservative aa substitution, . semi-conservative substitution.

FIG. 6F shows an extended IFITM1, 2, 3 and 5 protein sequence alignment (SEQ ID NOS 603-605, 598 and 601-602, respectively, in order of appearance). The two transmembrane domains as predicted by UnitprotKB, are shown in bold and underlined. The alignment was performed with ClustalIW. * identical amino acids (aa), : conservative aa substitution, . semi-conservative substitution.

FIGS. 9A-H are lists of a number of exemplary IFITM3 sequences in chickens (SEQ ID NOS 606-609, respectively, in order of appearance), chimpanzees (SEQ ID NOS 610-612, respectively, in order of appearance), rainbow trout (SEQ ID NOS 613-614, respectively, in order of appearance), mice (SEQ ID NOS 603, 615-616, 605 and 617, respectively, in order of appearance), macaques (SEQ ID NOS 618-619, respectively, in order of appearance), horses (SEQ ID NOS 620-621, respectively, in order of appearance), dogs, rats (SEQ ID NOS 622-624, respectively, in order of appearance), cows (SEQ ID NOS 625-627, respectively, in order of appearance), and humans (SEQ ID NOS 598-600 and 628, respectively, in order of appearance).

FIG. 10 is an alignment showing that the influenza A viral strains WS/33, WSN/33, and H3/Udorn possess Critical Anti-IFN Molecular Determinants within their NS1 Proteins. The NS1 proteins of the three viruses used in this study, PR8 (NCBI Protein database locus link, ACR15353) (SEQ ID NO: 631), WSN/33 (ABF83571) (SEQ ID NO: 629), WS/33 (AAA21582.1) (SEQ ID NO: 630) and H3/Udorn (ABD79037.1) (SEQ ID NO: 633) are shown, along with the NS1 protein from the highly pathogenic 1918 influenza strain A/Brevig_Mission/1/18 for comparison (AAK14368) (SEQ ID NO: 632). The amino acids, F103 and M106, suggested by Kochs et al. 2007 to be critical for CPSF binding and therefore the prevent the establishment of an IFN-induced restriction, are shown in bold and underlined within the box region. The alignment was performed with ClustalW. * identical amino acids (aa), : conservative aa substitution, . semi-conservative substitution.

FIG. 11A is a line graph showing the results of experiments wherein A549 cell lines were infected with increasing amounts of VN/04. Twelve hours after infection the cells were immunostained for NP expression and scored for infection status. Values are representative of two independent experiments.

FIG. 11B shows the results of experiments wherein A549 cell lines were incubated on ice with H1N1 WSN/33 to permit viral-host binding. Cells were washed, fixed and immunostained for surface-bound HA protein, then analyzed by flow cytometry. Values given are percentage of cells staining for surface HA. Values are representative of three independent experiments.

FIG. 15 shows the sequence of NCBI Reference Sequence: NP_066362.2 interferon-induced transmembrane protein 3 (1-8U) [*Homo sapiens*], SEQ ID NO:598.

FIG. 16 shows the sequence of NCBI Reference Sequence: NP_006426.2 interferon induced transmembrane protein 2 (1-8D) [*Homo sapiens*], SEQ ID NO:599.

FIG. 17 shows the sequence of NCBI Reference Sequence: NP_003632.3 interferon induced transmembrane protein 1 (9-27) [*Homo sapiens*], SEQ ID NO:600.

DETAILED DESCRIPTION

Figure 1A:
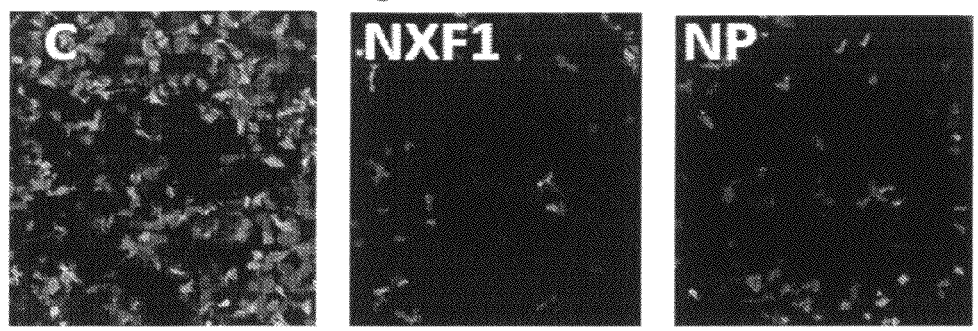
FIG. 1A is a set of three images of U2OS cells transfected with the indicated siRNAs for 72 hours, then infected with influenza A virus (PR8) and immuno-stained 12 hours later for hemaggutinin (green: hemagluttinin, HA). C, Nontargeting siRNA negative control. Magnification, 4×.

Influenza viruses exploit host cell machinery to replicate, resulting in epidemics of respiratory illness. In turn, the host expresses anti-viral restriction factors to defend against infection. To find host-cell modifiers of influenza A H1N1 viral infection, a functional genomic screen was used to identify, in human cells, over 120 influenza A virus-dependency factors (IDFs) with roles in endosomal acidification, vesicular trafficking, mitochondrial metabolism, and RNA splicing. The screen also led to the discovery that the interferon-inducible trans-membrane proteins, IFITM1, 2 and 3, restrict early replication of influenza A virus. The IFITM proteins control basal resistance to Influenza A, but are also inducible by interferons (IFN) type I and II, and are critical for IFN's virustatic actions. Further characterization revealed that the IFITM proteins inhibit the early replication of flaviviruses, including dengue virus (DNV) and West Nile virus (WNV). Collectively this work identifies a new family of anti-viral restriction factors, which mediate the cell-intrinsic innate immune system's response to at least three major human pathogens.

The IFITM Protein Family

The screen identified the IFITM proteins as viral restriction factors. IFITM proteins were originally described 25 years ago by Freidman et al. based on their expression in neuroblastoma cells after interferon treatment (Friedman et al., Cell 38, 745-755, 1984). The IFITM1, 2, 3 and 5 genes lie adjacent to one another on chromosome 11, and all encode for two predicted membrane-spanning domains, separated by a highly conserved intracellular loop (Lewin et al., Eur J Biochem 199, 417-423, 1991, FIG. 6F). IFITM1, 2 and 3 are nearly ubiquitously expressed. In contrast, IFITM5 displays a more restricted pattern, being expressed primarily in bone tissue (Moffatt et al., J Bone Miner Res. 2008 September; 23(9):1497-508). While IFITM1 homologs are found in frog, fish, fowl and swine, IFITM2 and 3 homologues are found in more recently diverged mammalian species (mouse, rat, cow, chimpanzee, and human) (see the world wide web at ncbi.nlm.nih.gov/sites/entrez), suggesting that IFITM1 is the original ancestral gene, with IFITM2 and 3 arising in a later gene duplication event (FIG. 6F).

The IFITM proteins have been ascribed roles in immune cell signaling, cell adhesion, oncogenesis, and germ cell homing and maturation (Smith, R. A., et al., Genes Immun, 2006. 7(2): p. 113-21; Lange, U. C., et al., Mol Cell Biol, 2008. 28(15): p. 4688-96; Lange, U. C., et al., BMC Dev Biol, 2003. 3: p. 1; Ropolo, A., et al., Biochem Biophys Res Commun, 2004. 319(3): p. 1001-9; Evans, S. S., et al., J Immunol, 1993. 150(3): p. 736-47; Moffatt, P., et al., J Bone Miner Res, 2008. 23(9): p. 1497-508). Consistent with our studies demonstrating that both termini of the IFITM proteins are extra-cellular, IFITM1 has been reported to reside in lipid rafts on the cell surface, where it may play a role in both cell adhesion and immune cell signaling (Bradbury et al., J Immunol 149, 2841-2850, 1992). However, as of now we know of no functional studies clearly demonstrating an additional function for an IFITM protein family member. Indeed, in our hands, transformed and primary cells either over-expressing or depleted for IFITM3, display no growth perturbations, and as noted, the IfitmDel mice develop and age normally (Lange et al., Mol Cell Biol 28, 4688-4696, 2008).

Interestingly, the IFITM proteins belong to a protein domain super-family, consisting of over 30 proteins, each possessing two trans-membrane domains and an intervening highly conserved intra-cellular loop (pfam04505, CD225, Interferon-induced transmembrane protein). Members of the CD225 protein family have been reported to be expressed in zebrafish, *Xenopus*, the purple sea-cucumber, and several bacteria.

Reference sequences for the human proteins are known in the art, see, e.g., NCBI Reference Sequence: NP_066362.2 interferon-induced transmembrane protein 3 (1-8U) [*Homo sapiens*] (SEQ ID NO:598), NCBI Reference Sequence: NP_006426.2 interferon induced transmembrane protein 2 (1-8D) [*Homo sapiens*] (SEQ ID NO:599), or NCBI Reference Sequence: NP_003632.3 interferon induced transmembrane protein 1 (9-27) [*Homo sapiens*] (SEQ ID NO:600). In some embodiments of the methods and compositions described herein, the IFITM protein is at least 95% identical to these reference sequences, e.g., at least 96%, 97%, 98%, 99% or 100% identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Methods and Cells for Producing Intracellular Pathogens

The discovery of the role of IFITM1, 2 and 3 in pathogen restriction has allowed the development of cells and cell lines that are useful for the production of pathogens, e.g., for use in research or in the manufacture of vaccines. The cells and cell lines are those in which IFITM1, 2, and/or 3 (referred to herein collectively as "IFITM"), or their ascribed actions, are specifically deleted, depleted or antagonized. In some embodiments, IFITM3 is deleted but at least one other IFITM family member is retained and is functional. In some embodiments, other viral restriction factors and interferon-inducible proteins/factors are also deleted, e.g., MxA and MxB, in order to further compromise the viral-producer cells from inhibiting viral replication (GenBank Ref. Sequence Nos. NM_001144925.1 (MX1 human, var.1), NM_002462.3 (MX1 human, var. 2), NM_204609.1 (*gallus gallus*), NM_214061.1 (swine), and NM_002463.1 (MX2 human). Each of these sequences are incorporated by reference herein Intracellular Pathogens IFITM proteins can act as viral restriction factors by inhibiting endocytosis. Thus, the three IFITM3 proteins can be used to change the entry and/or decrease infection of any agent that is endocytosed, e.g., any intracellular pathogens such as viruses, bacteria or bacterial toxins that are endocytosed. Thus the cells, compositions, and methods described herein can be used to produce or inhibit infection with pathogens or toxins which infect host cells A number of different viruses and pathogens are provided herein. These include but are not limited to orthomyxoviruses: including influenza A virus, influenza B virus, and influenza C virus, all strains of influenza viruses infecting humans, birds, pigs, seals and horses, (e.g., influenza A (H1N1 (both A/WS/33 and A/California/04/2009 strain), H2N2, H3N2, H5N1, H7N7, H1N2, H9N2, H7N2, H7N3 and H10N7), B and C viruses, as well as avian influenza (for example, strains H5N1, H5N2, H7N1, H7N7 and H9N2). Thogoto and Dhori viruses, Quaranfil virus, Lake Chad virus, Johnston Atoll virus, infectious salmon anemia virus (isaviruses), and flaviviruses: including West Nile virus, dengue virus, Omsk virus, yellow fever virus, Mammalian tick-borne virus group including, Gadgets Gully virus (GGYV), Kadam virus (KADV), Kyasanur Forest disease virus (KFDV), Langat virus (LGTV), Omsk hemorrhagic fever virus (OHFV), Powassan virus (POWV), Royal Farm virus (RFV), Tick-borne encephalitis viruses (TBEV): including Louping ill virus (LIV), Seabird tick-borne virus group, Meaban virus (MEAV), Saumarez Reef virus (SREV), Tyuleniy virus (TYUV), and Mosquito-borne viruses including: Aroa virus group, Aroa virus (AROAV), and the Dengue virus group including: Dengue virus (DNV), Kedougou virus (KEDV), and the Japanese encephalitis virus group, including: Cacipacore virus (CPCV), Koutango virus (KOUV), Japanese encephalitis virus (JEV), Murray Valley encephalitis virus (MVEV), St. Louis encephalitis virus (SLEV), Usutu virus (USUV), West Nile virus (WNV), Kunjin virus, Yaounde virus (YAOV), Kokobera virus group, Kokobera virus (KOKV), Ntaya virus group, Bagaza virus (BAGV), Ilheus virus (ILHV), Israel turkey meningoencephalomyelitis virus (ITV), Ntaya virus (NTAV), Tembusu virus (TMUV), Spondweni virus group, Zika virus (ZIKV), Yellow fever virus group, Banzi virus (BANV), Bouboui virus (BOUV), Edge Hill virus (EHV), Jugra virus (JUGV), Saboya virus (SABV), Sepik virus (SEPV), Uganda S virus (UGSV), Wesselsbron virus (WESSV), Yellow fever virus (YFV), and viruses with no known arthropod vector including: the Entebbe virus group: Entebbe bat virus (ENTV), Yokose virus (YOKV), the Modoc virus group as follows: Apoi virus (APOIV), Cowbone Ridge virus (CRV), Jutiapa virus (JUTV), Modoc virus (MODV), Sal Vieja virus (SVV), San Perlita virus (SPV), and the Rio Bravo virus group: as named Bukalasa bat virus (BBV), Carey Island virus (CIV), Dakar bat virus (DBV), Montana myotis leukoencephalitis virus (MMLV), Phnom Penh bat virus (PPBV), Rio Bravo virus (RBV) Tyuleniy virus (TYUV) and the viral hepatitidies: Hepatitis A virus Hepatitis C virus, and Hepatitis B virus, Hepatitis E, Hepatitis G virus, and retroviruses including: human immunodeficiency virus (HIV), simian immunodeficiency virus (SIV), Human T cell leukemia virus, JC virus, Acanthamebiasis, Australian bat lyssavirus, Hendra or equine morbilli virus, coxsackie viruses (including A) Parvovirus B19, poliovirus, rabies virus, Japanese encephalitis virus, La Crosse virus, Hantaan virus, Rabies, Chikungunya virus, Severe acute respiratory syndrome-associated coronavirus (SARS-CoV), Rift Valley Fever virus, Crimean-Congo hemorrhagic fever virus, Mumps virus, Enterovirus 71, Variola major (smallpox) and other related pox viruses, Viral hemorrhagic fevers, Arenaviruses: LCM, Junin virus, Machupo virus, Guanarito virus, Lassa Fever, Bunyaviruses, Hantaviruses, Rift Valley Fever, Filoviruses, Ebola, Marburg, Caliciviruses, Hepatitis A, LaCrosse virus, California encephalitis virus, Venezualan equine encephalitis (VEE) virus, Eastern EE virus, Western EE virus, Japanese Encephalitis virus, Kyasanur Forest virus, and Crimean-Congo Hemorrhagic Fever virus; the Picornaviridae, e.g., viruses in the following genera: Enterovirus, Rhinovirus, Cardiovirus, Aphthovirus, Parechovirus, Erbovirus, Kobuvirus, and Teschovirus, and DNA viruses such as EBV, CMV, HSV, Human herpesvirus 8, Human herpesvirus 6, Human papilloma virus, and adenoviruses.

Bacterial pathogens and their respective toxins that are endocytosed include, but are not limited to: Gram-negative bacteria (e.g., proteobacteria including Enterobacteriaceae (e.g., *Escherichia coli* (e.g., diarrheagenic and hemorrhagic *E. coli*, including EHEC O157), *Salmonella*, and *Shigella*), Pseudomonads, Diplococcus (e.g., *Moraxella*), *Helicobacter*, *Campylobacter* (e.g., *Campylobacter jejuni*), *Stenotrophomonas* (e.g., *S. maltophilia*), *Bdellovibrio*, acetic acid bacteria, *Legionella*; alpha proteobacteria (e.g., *Wolbachia*); cyanobacteria, spirochaetes, green sulfur and green non-sulfur bacteria; *Niesseria* (e.g., *N. gonorrhoeae* and *N. meningitides*), *Rickettsia*, e.g., *Rickettsia prowazekiz*) *Moraxella catarrhalis*, Pasteurellaceae (e.g., *Haemophilus influenzae*); Chlamydophylla (e.g., *Chlamydia psittaci* and *C. abortus*; some additional specific examples of gram-negative bacteria include *Klebsiella pneumoniae*, *Bartonella henselae*, *Legionella pneumophila*, *Pseudomonas aeruginosa*, *Ehrlichiosis Proteus mirabilis*, *Enterobacter cloacae*, *Serratia marcescens*, *Helicobacter pylori*, *Salmonella enteritidis*, *Yersinia pestis* and *Yersinia enterocolitica*, *Salmonella typhi*, *Burkholderia pseudomallei*(glanders), *Coxiella burnetii* (Q fever), *Brucella* species (brucellosis), *Francisella tularensis* (tularemia) and *Acinetobacter baumannii*) and Gram-positive bacteria (e.g., *Bacillus*, *Clostridium*, *Sporohalobacter*, *Anaerobacter*, *Heliobacterium*, *Staphylococcus* (e.g., Group A *Staphylococcus aureus*), *Streptococcus*, *Enterococcus*, *Corynebacterium*, *Nocardia*, *Actinobacteria*, and *Listeria*, and Mollicutes, e.g., *Mycoplasma* and *Mycobacterium* including *Mycobacterium Tuberculosis*, *M. Leprae* and Multidrug-resistant Tuberculosis; fungi, e.g., *Coccidioides*, e.g., *C. posadasii*, and *Coccidioides immitis*; and protozoa, e.g., *Cyclospora cayatanensis*, *Cryptosporidia*, e.g., *C. parvum* *Giardia lamblia*, *Entamoeba histolytica*, *Toxoplasma* (e.g., *T. gondii*), *Babesia*; *Microsporidia*, e.g., *Encephalitozoon hellem* and *Enterocytozoon bieneusi*; and bacterial toxins including *Bacillus anthracis* (anthrax), *Clostridium botulinum* toxin, Ricin toxin (from *Ricinus communis*), Epsilon toxin of *Clostridium perfringens*, and *Staphylococcus* enterotoxin B.

Cells

Also provided herein are isolated cells that have a specific reduction in an IFITM, plus one or more other viral restriction factors. The terms "host cell" and "recombinant host cell" are used interchangeably herein. Such terms refer not only to the particular subject cell that was contacted with a nucleic acid molecule (e.g., an inhibitory nucleic acid that reduces expression of an IFITM protein, or a knockout vector that induces functional deletion of one or more IFITM genes from the genomic DNA of the cell), but to the progeny or potential progeny of such a cell that also contain the nucleic acid molecule. Because certain modifications may occur in succeeding generations due to either mutation or environmental influences, such progeny may not, in fact, be identical to the parent cell, but are still included within the scope of the term as used herein so long as they also contain the nucleic acid molecule. In some embodiments, the cells are also infected with an intracellular pathogen, e.g., a virus, bacterium, or bacterial toxin, e.g., as described herein.

A host cell can be any prokaryotic or eukaryotic cell. For example, the cell can be a bacterial cell such as *E. coli*, insect cells, yeast or mammalian cells (such as African green monkey kidney (Vero), human PER.C6, Madin-Darby canine kidney (MDCK) cells, transformed or primary chicken cells, avian embryonated egg cells, such as chicken, Chinese hamster ovary cells (CHO), HEK 293, or COS cells). Other suitable host cells are known to those skilled in the art. In general, in the methods described herein, the cell will be one that is useful for the production of virus.

Vector DNA or inhibitory nucleic acids can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In some embodiments, naked DNA is simply applied to a cell. Where the vector is a viral vector, known infection protocols can be used.

For example, retroviral vectors can be used, e.g., as described in Robertson et al., Nature 323:445-448 (1986). Retroviruses generally integrate into the host genome with no rearrangements of flanking sequences, which is not always the case when DNA is introduced by microinjection or other methods.

Cells of the present invention also include those cells obtained from the transgenic animals described herein, e.g., cells from the tissues of those animals that overexpress IFITM1, 2, or 3.

Specific deletion of IFITM1, 2, or 3 can be accomplished using any method known in the art, e.g., using homologous recombination or recombinantly engineered zinc-finger nucleases to delete the selected gene from the genomic DNA, or using inhibitory nucleic acids, e.g., transiently or stably expressed inhibitory nucleic acids.

Inhibitory Nucleic Acids

Inhibitory nucleic acids, e.g., siRNA, shRNA, miRNA, LNA, antisense, ribozymes, or aptamers, directed against the selected gene(s), can be used to specifically reduce expression of a gene described herein, e.g., IFITM1, 2, or 3, or a gene listed in Table 1 or Table 2. The deletion can thus be permanent (e.g., in the genomic DNA) or transient (e.g., only in the presence of siRNA or antisense).

RNA Interference

RNA interference (RNAi) is a process that induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev.:12, 225-232 (2002); Sharp, Genes Dev., 15:485-490 (2001); Valencia-Sanchez et al. Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), by microRNA (miRNA), functional small-hairpin RNA (shRNA), or other dsRNAs which are expressed in vivo using DNA templates with RNA polymerase II or III promoters (Zeng et al., Mol. Cell. 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002).)

siRNA Molecules In general, the methods described herein can use dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the invention includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004))

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

siRNA Delivery

Direct delivery of siRNA in saline or other excipients can silence target genes in tissues, such as the eye, lung, and central nervous system (Bitko et al., Nat. Med. 11:50-55 (2005); Shen et al., Gene Ther. 13:225-234 (2006); Thakker, et al., Proc. Natl. Acad. Sci. U.S.A. (2004)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)).

Liposomes and nanoparticles can also be used to deliver siRNA into animals. Delivery methods using liposomes, e.g. stable nucleic acid-lipid particles (SNALPs), dioleoyl phosphatidylcholine (DOPC)-based delivery system, as well as lipoplexes, e.g. Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain. 1:29 (2005); Zimmermann et al., Nature 441:111-114 (2006)). Conjugating siRNA to peptides, RNA aptamers, antibodies, or polymers, e.g. dynamic polyconjugates, cyclodextrin-based nanoparticles, atelocollagen, and chitosan, can improve siRNA stability and/or uptake. (Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007); Rozema et al., Proc. Natl. Acad. Sci. U.S.A. 104:12982-12987 (2007); Song et al., Nat. Biotechnol. 23:709-717 (2005); Soutschek (2004), supra; Wolfrum et al., Nat. Biotechnol. 25:1149-1157 (2007))

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)).

Stable siRNA Expression

Synthetic siRNAs can be delivered into cells, e.g., by direct delivery, cationic liposome transfection, and electroporation. However, these exogenous siRNA typically only show short term persistence of the silencing effect (4-5 days). Several strategies for expressing siRNA duplexes within cells from recombinant DNA constructs allow longer-term target gene suppression in cells, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

In another embodiment, siRNAs can be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, *Cell* 116:281-297 (2004); Valencia-Sanchez et al., Genes & Dev. 20:515-524 (2006)) One common feature of miRNAs is that they are excised from an approximately 70 nucleotide precursor RNA stem loop by Dicer, an RNase III enzyme, or a homolog thereof. By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, the mRNA to be targeted by the siRNA generated from the engineered RNA precursor will be depleted from the cell or organism, leading to a decrease in the concentration of the protein encoded by that mRNA in the cell or organism.

Antisense

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

The antisense nucleic acid molecules of the invention are typically administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription, splicing, and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense nucleic acid molecule of the invention is an ∀-anomeric nucleic acid molecule. An ∀-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-β-methylribonucleotide (Inoue et al. Nucleic Acids Res. 15:6131-6148 (1987)), 2'-β-methoxyethylribonucleotide, locked nucleic acid, ethylene-bridged nucleic acid, oxetane-modified ribose, peptide nucleic acid, or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region, e.g., promoters and/or enhancers) to form triple helical structures that prevent transcription of the target gene in target cells. See generally, Helene, C. *Anticancer Drug Des.* 6:569-84 (1991); Helene, C. *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target-protein encoding nucleic acid can include one or more sequences complementary to the nucleotide sequence of a target cDNA disclosed herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261: 1411-1418 (1993).

Transgenic Knock-in and Knockout Animals

Also provided herein are non-human transgenic knock-in and knockout animals, in which the IFITM1, 2 or 3 gene(s) is overexpressed or functionally deleted, respectively. Transgenic animals are expected to be resistant to viral and bacterial infection and are therefore useful, e.g., for reducing the incidence and spread of viral infections in the animal population, e.g., in feedstock animals. Knockout Animals are expected to be more susceptible to viral and bacterial infection and thus the animals or cells from those animals can be used for production of the virus or bacterium. For example, knockout chickens can be used to generate IFITM-knockout embryonated eggs for vaccine virus or overall virus production.

A "transgenic knock-in animal" is a non-human animal in which one or more of the cells of the animal includes an IFITM1, 2, and/or 3 knock-in transgene as described herein. A "knockout animal" is a non-human animal in which one or more of the cells of the animal includes an IFITM1, 2, and/or 3 knockout transgene that specifically deletes a functional IFITM1, 2, and/or 3 gene, or disrupts expression of the gene, as described herein.

Examples of transgenic knock-in and knock-out animals include mammals such as rodents (e.g., rats or mice), non-human primates, sheep, dogs, cows, pigs, and goats; birds such as turkeys, chickens, or ducks; amphibians, and the like. In some embodiments, the transgenic animals are feedstock animals that are prone to viral infections that can affect humans, e.g., pigs, and poultry, e.g., chickens, turkeys, and ducks. A "transgene" is exogenous DNA that is integrated into the genome of a cell from which a transgenic animal develops and thus remains in the genome of the mature animal, thereby affect the expression of a selected gene product in one or more cell types or tissues of the transgenic animal. Knock-in animals, which include a gene insertion, and knockout animals, which include a deletion of a functional gene or disruption of gene expression, are included in the definition of transgenic animals.

An "IFITM knock-in transgene" as used herein refers to a construct that includes sequences that have the effect of increasing expression of an IFITM in the cell. In some embodiments, the IFITM knock-in transgene includes an IFITM-encoding sequence, and a promoter that drives expression of the IFITM-encoding sequence. In some embodiments, the IFITM knock-in transgene includes only an exogenous promoter and optionally additional regulatory sequences to induce overexpression of an IFITM, and flanking sequences that promote homologous recombination into the genome at the site of the IFITM gene, such that the exogenous promoter replaces the endogenous IFITM promoter, and drives expression of the IFITM in the cells. In some embodiments, the exogenous promoter is a cell-, tissue-, or timing-specific promoter, e.g., a promoter that will turn on expression of the IFITM transgene in a specific cell or tissue, or at a specific time in development. In some embodiments, the exogenous promoter is inducible, and thus can be triggered by the administration of an inducing agent. A number of such inducible promoters that can be used in transgenic animals are known in the art. The transgene is generally integrated into or occurs in the genome of the cells of a transgenic animal.

An "IFITM knockout transgene" as used herein refers to a construct that includes sequences that have the effect of specifically decreasing IFITM1, 2, or 3 expression in the cell. In some embodiments, the IFITM knockout transgene disrupts the endogenous IFITM-coding sequence, or disrupts the promoter or other regulatory sequences that drive expression of the IFITM-coding sequence. In some embodiments, the IFITM knock-out transgene includes sequences that promote homologous recombination into the genome at the site of the IFITM gene, such that the exogenous promoter replaces the endogenous IFITM promoter, and disrupts expression of IFITM in the cells. In some embodiments, the knockout is a cell-, tissue-, or timing-specific knockout, e.g., that disrupts expression of the IFITM transgene in a specific cell or tissue, or at a specific time in development; for example, a cre-lox system can be used that crosses an animal expressing a tissue, cell, or timing-dependent recombinase (e.g., cre) with an animal expressing a floxed IFITM transgene. In some embodiments, the knockout is inducible, and thus can be triggered by the administration of an inducing agent. A number of such inducible promoters that can be used in transgenic animals are known in the art, e.g., inducible cre-lox systems. The knockout transgene is generally integrated into or occurs in the genome of the cells of a transgenic animal.

The IFITM knock-in or knockout transgene can be used to express or delete the IFITM protein in one or more cell types or tissues of the transgenic animal; expression of the IFITM transgene in a cell results in expression of the IFITM protein. Thus, a transgenic animal as described herein is one in which at least one copy of an IFITM transgene has been introduced into a cell of the animal, e.g., an embryonic cell of the animal, prior to development of the animal. A line of transgenic animals (e.g., mice, rats, guinea pigs, hamsters, rabbits, or other mammals) can be produced bearing an IFITM transgene in some or all of their cells. Methods known in the art for generating such transgenic animals would be used, e.g., as described below.

Methods known in the art for producing transgenic animals can be used to generate an animal, e.g., a mouse, chicken, pig, cow, or goat, that bears one IFITM transgene "allele." Two such heterozygous animals can be crossed to produce offspring that are homozygous for the IFITM transgene allele, i.e., have the sequence encoding the IFITM transgene integrated into both copies of a chromosome.

For example, in one embodiment, a suitable vector including a sequence encoding or disrupting IFITM1, 2 or 3 is introduced into a cell, e.g., a fertilized oocyte or an embryonic stem cell. Such cells can then be used to create non-human transgenic animals in which said sequences have been introduced into their genome. These animals can then in turn be bred with other transgenic animals that harbor the IFITM3 transgene, or another viral restriction factor, e.g., MxA or MxB.

Methods for generating transgenic animals, particularly animals such as mice, via embryo manipulation and electroporation or microinjection of pluripotent stem cells or oocytes, are known in the art and are described, for example, in U.S. Pat. Nos. 4,736,866 and 4,870,009, U.S. Pat. No. 4,873,191, U.S. Ser. No. 10/006,611, "Transgenic Mouse Methods and Protocols (Methods in Molecular Biology)," Hofker and van Deursen, Editors (Humana Press, Totowa, N.J., 2002); and in "Manipulating the Mouse Embryo," Nagy et al., Editors (Cold Spring Harbor Laboratory Press, Cold Spring Harbor, N.Y., 2002), which are incorporated herein by reference in their entirety. Methods similar to those used to create transgenic mice can be used for production of other transgenic animals, see, e.g., Love et al., (1994) Biotechnology 12:60-63 (Transgenic birds); McGrew et al., (2004) EMBO Rep 5:728-733 (transgenic chickens); Mozdziak et al., (2003) Dev Dyn 226:439-445 (transgenic chickens); Kamihira et al., (2005) J Virol 79:10864-10874 (transgenic chickens); Lillico et al., (2007) Proc Natl Acad Sci USA 104:1771-1776 (transgenic chickens).

In general, in the present methods, a transgenic animal can be made by injecting a vector made as described herein into the pronucleus of a fertilized oocyte and used for generation of a transgenic animal with the IFITM transgene expressed in all cells, using standard transgenic techniques, e.g., as described in "Transgenic Mouse Methods and Protocols (Methods in Molecular Biology)," Hofker and van Deursen, Editors (Humana Press, Totowa, N.J., 2002); U.S. Pat. Nos. 4,736,866 and 4,870,009, U.S. Pat. Nos. 4,873,191 and 6,791,006, and in Hogan, "Manipulating the Mouse Embryo," Nagy et al., Editors (Cold Spring Harbor Laboratory Press, Cold Spring Harbor, N.Y., 2002).

A transgenic founder animal can be identified based upon the presence of the IFITM transgene in its genome, for example by detecting the presence of the IFITM transgene sequences (e.g., IFITM1, 2, or 3 and/or the exogenous promoter), or by detecting the presence of the IFITM protein, e.g., by detecting overexpression or a tag incorporated into the IFITM transgene. Founder animals can also be identified by detecting the presence or expression of (e.g., the level of expression of) the IFITM mRNA in tissues or cells of the animals. For example, fibroblasts can be used, such as embryonic fibroblasts or fibroblasts derived from the post-natal animal, e.g., the ear of the post-natal animal. A transgenic founder animal can then be used to breed additional animals carrying the transgene. Moreover, transgenic animals carrying a IFITM transgene can further be bred to other transgenic animals carrying other transgenes. For example, as noted above, such IFITM transgenic animals can be bred to animals expressing other viral restriction factors, e.g., MxA. Such animals would have two or more layers of biologic defenses and the virus would have a harder time generating mutations within one virus that could overcome this "combinatorial restriction". In some embodiments, both restriction factors are expressed from a single inducible cis acting element, for example a promoter whose transcriptional activity is stimulated by the presence of a small-molecule that permits an activator to bind and induce transcription of the IFITM genes, so that farmers could add the inducing agent to the animals' feed or water to induce the expression of the transgenes, or increase their basal levels, during times of infection or increased risk of infection.

The present invention also provides a method of screening a cell for a variant form of a gene set forth in Table 1 or 2. A variant can be a gene with a functional deletion, mutation or alteration in the gene such that the amount or activity of the gene product is altered. These cells containing a variant form of a gene can be contacted with a pathogen to determine if cells comprising a naturally occurring variant of a gene set forth in Table 1 or 2 differ in their resistance to infection. For example, cells from an animal, for example, a chicken, can be screened for a variant form of a gene set forth in Table 1 or 2. If a naturally occurring variant is found and chickens possessing a variant form of the gene in their genome are less susceptible to infection, these chickens can be selectively bred to establish flocks that are resistant to infection. By utilizing these methods, flocks of chickens that are resistant to avian flu or other pathogens can be established. Similarly, other animals can be screened for a variant form of a gene set forth in Table 1 or 2. If a naturally occurring variant is found and animals possessing a variant form of the gene in their genome are less susceptible to infection, these animals can be selectively bred to establish populations that are resistant to infection. These animals include, but are not limited to, cats, fish, dogs, livestock (for example, cattle, horses, pigs, sheep, goats, etc.), laboratory animals (for example, mouse, monkey, rabbit, rat, gerbil, guinea pig, etc.) and avian species (for example, flocks of chickens, geese, turkeys, ducks, pheasants, pigeons, doves etc.). Therefore, the present application provides populations of animals that comprise a naturally occurring variant of a gene set forth in Table 1 or 2 that results in decreased or increased susceptibility to viral infection, thus providing populations of animals that are either more or less susceptible to viral infection. Similarly, if a naturally occurring variant is found and animals possessing a variant form of the gene in their genome are more or less susceptible to bacterial, parasitic or fungal infection, these animals can be selectively bred to establish populations that are resistant to bacterial, parasitic or fungal infection.

Methods of Screening

Included herein are methods for screening test compounds, e.g., polypeptides, polynucleotides, inorganic or organic large or small molecule test compounds, to identify agents useful in the treatment or prevention of viral infections by increasing IFITM expression, or those test compounds that can be used to antagonize IFITM expression and/or actions. Infections that can be treated or prevented using the compounds identified by these methods include infections with the intracellular pathogens, e.g., viruses and bacteria, described herein.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Any small molecule that inhibits activity of a gene product set forth in Table 1, or similarly increases the activity of a gene product in Table 2, can be utilized in the methods of the present invention to decrease infection. These molecules are available in the scientific literature, in the StarLite database available from the European Bioinformatics Institute, in DrugBank (Wishart et al. *Nucleic Acids Res.* 2006 Jan. 1; 34 (Database issue):D668-72), package inserts, brochures, chemical suppliers (for example, Sigma, Tocris, Aurora Fine Chemicals, to name a few), or by any other means, such that one of skill in the art makes the association between a gene product of Table 1 and inhibition of this gene product by a molecule, or a gene product of Table 2 and an increase in this gene product by a molecule. Preferred small molecules are those small molecules that have $IC_{50}$ values of less than about 1 mM, less than about 100 micromolar, less than about 75 micromolar, less than about 50 micromolar, less than about 25 micromolar, less than about 10 micromolar, less than about 5 micromolar or less than about 1 micromolar.

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to increase or decrease the expression or function of IFITM proteins is evaluated. In addition, the ability of a test compound to decrease viral infectivity and replication by means of staining for viral protein expression, viral genome production, or progeny virus production (tittering assay) can be evaluated. The specificity of this test compounds actions via IFITM proteins could be confirmed in an IFITM null or hypomorphic genetic background.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect an effect on IFITM expression levels. Ability to modulate signaling via the kallikrein/kinin pathway can be evaluated, e.g., using liberation of bradykinin or other proteolytic products of kininogen (see, e.g., Campbell et al., Braz J Med Biol Res. 2000 June; 33(6):665-77), and using the measurement of cyclic guanine monophosphate (cGMP). Vascular permeability can be evaluated, e.g., as described herein.

A test compound that has been screened by a method described herein and determined to increase expression of IFITM, can be considered a candidate compound. A candidate compound that has been screened, e.g., in an in vivo model of a disorder, e.g., an animal exposed to the virus, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase expression of IFITM) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating or preventing viral infections as described herein, e.g., infections with an intracellular pathogen as described herein, e.g., a virus or bacterium as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a viral infection, as described herein. The animal can be monitored for a change in the disorder, e.g., for an improvement in a parameter of the disorder, e.g., a parameter related to clinical outcome. In some embodiments, the parameter is viral load, and an improvement would be a decrease in viral load. In some embodiments, the subject is a human, e.g., a human with a viral infection, and the parameter is severity or duration of symptoms associated with the viral infection.

Methods of Treatment

The methods described herein include methods for the treatment of disorders associated with infections with the intracellular pathogens, e.g., viruses, bacteria, and bacterial toxins, described herein. In some embodiments, the disorder is infection with an orthomyxovirus or flavivirus, e.g., an influenza virus. In some embodiments, the methods include administering a therapeutically effective amount of a therapeutic compound comprising and IFITM as described herein, to a subject who is in need of, or who has been determined to be in need of, such treatment. In some embodiments, the methods include administering a therapeutically effective amount of an inhibitory nucleic acid that specifically reduces expression of a gene listed in Table 1 as described herein, to a subject who is in need of, or who has been determined to be in need of, such treatment.

As used in this context, to "treat" means to ameliorate at least one symptom of the disorder associated with the infection. In general, administration of a therapeutically effective amount of a compound described herein for the treatment of an infection associated with an intracellular pathogen as described herein will result in a decreased level, duration, or severity of the infection or one or more clinical symptoms of the disorder.

As used herein, "treatment" includes treating, inhibiting, or preventing viral or bacterial infection in an animal, including a human. "Preventing" need not require 100% prevention, but can instead include reducing a subject's risk of developing the infection.

An infection can be a viral infection, bacterial infection, fungal infection or a parasitic infection, to name a few. An increase, or decrease or inhibition, of infection can occur in a cell, in vitro, ex vivo or in vivo. As utilized throughout, the term "infection" encompasses all phases of pathogenic life cycles including, but not limited to, attachment to cellular receptors, entry, internalization, disassembly, replication, genomic integration of pathogenic sequences, transcription of pathogen RNA, translation of pathogen RNA, transcription of host cell mRNA, translation of host cell mRNA, proteolytic cleavage of pathogenic proteins or cellular proteins, assembly of particles, endocytosis, cell lysis, budding, and egress of the pathogen from the cells. Therefore, a decrease or increase in infection can be a decreaseor increase in attachment to cellular receptors, a decrease or increase in entry, a decrease or increase in internalization, a decrease or increase in disassembly, a decrease or increase in replication, a decrease or increase in genomic integration of pathogenic sequences, an increase or decrease in transcription of viral RNA, a decrease or increase in translation of viral RNA, a decrease or increase in transcription of host cell mRNA, a decrease or increase in translation of host cell mRNA, a decrease or increase in proteolytic cleavage of pathogenic proteins or cellular proteins, a decrease or increase in assembly of particles, a decrease or increase in endocytosis, a decrease or increase in cell lysis, a decrease or increase in budding, or a decrease or increase in egress of the pathogen from the cells. This decrease or increase does not have to be complete as this can range from a slight decrease to complete ablation of the infection, or a slight increase to a very large increase.

A decrease in infection can be at least about 10%, 20%, 30%, 40%, 50%, 60, 70%, 80%, 90%, 95%, 100% or any other percentage decrease in between these percentages as compared to the level of infection in a control cell, for example, a cell wherein expression or activity of a gene or a gene product set forth in Table 1 has not been decreased. A decrease in infection can be at least about 10%, 20%, 30%, 40%, 50%, 60, 70%, 80%, 90%, 95%, 100% or any other percentage decrease in between these percentages as compared to the level of infection in a control cell that has not been contacted with a compound that decreases expression or activity of a gene or gene product set forth in Table 1.

In the methods set forth herein, inhibiting transcription of the gene, or inhibiting translation of its gene product can inhibit expression. Similarly, the activity of a gene product (for example, an mRNA, a polypeptide or a protein) can be inhibited, either directly or indirectly. Inhibition or a decrease in expression does not have to be complete as this can range from a slight decrease in expression to complete ablation of expression. For example, expression can be inhibited by about 10%, 20%, 30%, 40%, 50%, 60%, 70%, 80%, 90%, 95%, 99%, 100% or any percentage in between as compared to a control cell wherein the expression of the gene product has not been decreased or inhibited or as compared to the level of infection in a control cell that has not been contacted with a compound that decreases expression or activity of a gene or gene product set forth in Table 1.

Similarly, inhibition or decrease in the activity of a gene product does not have to be complete as this can range from a slight decrease to complete ablation of the activity of the gene product. For example, the activity of a gene product can be inhibited by about 10%, 20%, 30%, 40%, 50%, 60%, 70%, 80%, 90%, 95%, 99%, 100% or any percentage in between as compared to a control cell wherein activity of a gene product set forth in Table 1 has not been decreased or inhibited, or as compared to a control cell not contacted with a compound that inhibits the activity of a gene product set forth in Table 1. As utilized herein, "activity of a gene product" can be an activity that is involved in pathogenicity, for example, interacting directly or indirectly, with pathogen, e.g. viral protein or viral nucleic acids, or an activity that the gene product performs in a normal cell, i.e. in a non-infected cell. Depending on the gene product, one of skill in the art would know how to assay for an activity that is involved in pathogenicity, an activity that is involved in normal cellular function, or both. As set forth above, an activity of the proteins and nucleic acids listed herein can be the ability to bind or interact with other proteins. Therefore, the present invention also provides a method of decreasing infection by inhibiting or decreasing the interaction between any of the proteins of the present invention and other cellular proteins, such as, for example, transcription factors, receptors, enzymes (for example, kinases, phosphatases, synthases, lyases, hydrolases, proteases, transferases, nucleases, ligases, reductases, polymerases) and hormones, provided that such inhibition correlates with decreasing infection by the pathogen. The present invention also provides a method of decreasing infection by inhibiting or decreasing the interaction between any of the proteins of the present invention and a cellular nucleic acid or a viral nucleic acid. Also provided is a method of decreasing infection by inhibiting or decreasing the interaction, either direct or indirect, between any of the proteins of the present invention and a viral, bacterial, parasitic or fungal protein (i.e. a non-host protein).

An increase in infection, such as that which occurs with the genes in Table 2, can be at least about a 2, 3, 4, 5, 6, 7, 8, 9, 10, 20, 30, 40, 50, 60, 70, 80, 90, or 100 fold increase, or any amount below, above, or in between these amounts, as compared to the level of infection in a control cell, for example, a cell wherein expression or activity of a gene or a gene product set forth in Table 2 has not been increased. An increase in infection can be at least about a 2, 3, 4, 5, 6, 7, 8, 9, 10, 20, 30, 40, 50, 60, 70, 80, 90, or 100 fold increase, or any amount below, above, or in between these amounts that has not been contacted with a compound that increases expression or activity of a gene or gene product set forth in Table 2.

The cells of the present invention can be prokaryotic or eukaryotic, such as a cell from an insect, fish, crustacean, mammal, bird, reptile, yeast or a bacterium, such as *E. coli*. The cell can be part of an organism, or part of a cell culture, such as a culture of mammalian cells or a bacterial culture. Therefore, the cell can also be part of a population of cells. Also included are stem cells. The cell(s) can also be in a subject.

Examples of viral infections include but are not limited to, infections caused by RNA viruses (including negative stranded RNA viruses, positive stranded RNA viruses, double stranded RNA viruses and retroviruses) and DNA viruses. All strains, types, subtypes of DNA and RNA viruses are contemplated herein.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include IFITM polypeptides described herein as active ingredients. In general, the compositions will include liposomes or other agents that promote incorporation of the IFITM polypeptide into the cell membranes of the target host cells. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., antiviral or antibacterial compounds.

Pharmaceutical compositions are typically formulated to be compatible with its intended route of administration. Examples of routes of administration include parenteral, e.g., intravenous, intradermal, subcutaneous, oral (e.g., inhalation), transdermal (topical), and transmucosal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Screening

Included herein are methods for screening test compounds, e.g., polypeptides, polynucleotides, inorganic or organic large or small molecule test compounds, to identify agents that modulate infection with a pathogen, e.g., viral or bacterial infection, e.g., infection with influenza A. The methods include selecting one or more target genes or proteins from Table 1 or Table 2, and using known assays to identify test compounds that increase or decrease expression or activity of the selected target gene or protein. For example, a test compound that decreases expression of a gene listed in Table 1, or increases expression of a gene listed in Table 2, would be a candidate compound for decreasing or inhibiting viral infection, whereas a test compound that increases expression of a gene listed in Table 1, or decreases expression of a gene listed in Table 2, would be a candidate compound for increasing or promoting viral infection. Compounds that decrease or inhibit viral infection are useful as potential therapeutics for the treatment of viral infections. Compounds that increase or promote viral infection are useful in the production of viruses, e.g., for research or therapeutic purposes (e.g., for gene therapy) or for use in vaccines.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to increase or decrease expression or activity of a gene or protein listed in Table 1 or Table 2 can be evaluated; alternatively or in addition, the ability of the test compound to inhibit or decrease viral infection in the cell can be evaluated.

In some embodiments, the test sample is, or is derived from (e.g., a sample taken from) an in vivo model of a disorder as described herein. For example, an animal model, e.g., a rodent such as a rat, can be used. Animal models may be particularly useful for validating a compound identified as increasing or decreasing expression or activity of a gene or protein listed in Table 1 or Table 2, e.g., for evaluating the ability of the compound to inhibit (treat) or promote a viral infection in the animal. Animal models useful in evaluating therapeutics for the treatment of viral infections induce mice, ferrets, rats (e.g., cotton rats), pigs, and non-human primates. See, e.g., Barnard, Antiviral Research 82(2):A110-A122 (2009).

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on protein or transcript levels of a gene listed in Table 1 or Table 2. Ability to modulate viral infection can be evaluated, e.g., using immunofluorescence assays that detect changes in viral proteins; viral reporter gene assays where infection results in the activation or expression of a reporter protein, e.g., a fluorescent or other detectable reporter such as green fluorescence protein or beta-galactosidase; or tittering assays, e.g., where the supernatant from the cultures involving the experimentally manipulated cells is replica plated in a well-by-well manner onto fresh host cells and the specific infectivity of the viral supernatant determined; or cytopathic effect assays, wherein imaging of nuclei or quantitation of ATP can be used as a readout for the remaining viable cells that have resisted infection by a virus or other pathogen or toxin after exposure or treatment by a test compound (see, e.g., Li et al., Proc Natl Acad Sci USA. 2009 Sep. 22; 106(38):16410-5; Krishnan et al., Nature. 2008 Sep. 11; 455(7210):242-5; Brass et al., Science. 2008 Feb. 15; 319 (5865):921-6. Epub 2008 Jan. 10.).

A test compound that has been screened by a method described herein and determined to increase or decrease expression or activity of a gene or gene product listed in Table 1 or Table 2 can be considered a candidate compound. A candidate compound that has been screened, e.g., in an in vivo model of a disorder, e.g., an animal model of viral infection, and determined to have a desirable effect on the disorder, e.g., on viral load, or one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase or decrease expression or activity of a gene or gene product listed in Table 1 or Table 2) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with viral infection, as described herein, e.g., influenza. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to a cell or animal model of a disorder associated with an infection, e.g., a viral infection, e.g., an infection with influenza A virus, as described herein. The animal can be monitored for a change in the disorder, e.g., for an improvement in a parameter of the disorder, e.g., a parameter related to clinical outcome. In some embodiments, the parameter is decreased viral activity observed in standard cell culture and mouse protection assays as known in the art, in example indirect immunofluorescence detection of viral Ag in WNV-infected Vero cells or influenza A infected MDCK cells, or infection by the appropriate reporter cells for any number of viruses, bacteria, or toxins using the appropriate cell lines or primary cells and assays, using treated cell media or animal sera. In addition, the pathologic analysis of upper respiratory tract and/or lung tissue infection or airway epithelial damage, encephalitis, and or death could be used as a read out for efficacy or protection. Evidence of an improvement could include decreases in the levels of viral or bacterial products/antigens or viruses or bacteria themselves in cells or animals challenged with the respective virus or other pathogen, as determined by viral titer on reporter cells or animals, and/or decrease in airway tissue and lung tissue viral/pathogen-induced damage, meninegeal and/or brain tissue inflammation or destruction, in addition an improvement would also be increased duration of survival, and/or well-being of cells or animals as measured by standard parameters. See, e.g., Mount and Belz, Methods Mol. Biol. 2010; 595: 299-318; Barnard, Antiviral Research 82(2): A110-A122 (2009); van der Laan et al., Oxford J. Expert Rev Vaccines. 2008 August; 7(6):783-93; Burleson and Burleson, J. Immunotoxicol. 2008 January; 5(1):23-31; Wang et al., J. Nutr. 2009 March; 139(3):598-602; and Chu et al., J. Immunol. 2007 Mar. 1; 178(5):2699-705). In some embodiments, the subject is a human, e.g., a human with influenza, and the parameter is duration or severity of symptoms; an improvement would be a shortening in duration and a lessening of severity of symptoms. Symptoms can include fever, muscle aches, headache, lack of energy, dry cough, pharyngitis (sore throat), and rhinitis (runny nose).

EXAMPLES

The invention is further described in the following examples, which do not limit the scope of the invention described in the claims.

Example 1

An siRNA Screen for Influenza A Virus Infection Modifying Host Factors

RNA interference (RNAi) permits the exploration of functional host-viral interactions. A recent RNAi screen using insect cells identified 98 *D. melanogaster* proteins that are required for infection by a recombinant influenza virus (Hao et al., Nature 454, 890-893, 2008). Considering the complexities of host-pathogen relationships and the fact that flies lack many of the basic mechanisms mammals use to fight viral infections, we reasoned that further interactions could be brought to light using a human genome-wide siRNA screen.

To identify host factors required for influenza A virus infection, a high-throughput RNAi-based screen was undertaken on an arrayed library targeting 17,877 genes (Dharmacon siARRAY siRNA Library (Human Genome, G-005000-05, Thermo Fisher Scientific, Lafayette, Colo., the remaining 3,244 pools of the original 21,121 gene library were not screened because the vast majority have been retired due to revised refseq annotation or other concerning characteristics). siRNAs were transiently reverse transfected into human osteosarcoma cells (U2OS) cells at a 50 nM final concentration, using a final concentration of 0.32% Oligofectamine (Invitrogen, Carlsbad, Calif.) in a 384-well format (384 well, black plastic, clear bottomed assay plate, Corning 3712). U2OS cells were grown in DMEM (Invitrogen Cat#11965) with 10% FBS (Invitrogen). The next day, 5 uL of fresh complete media (DMEM with 10% FBS, Invitrogen) was added to the outer two wells at the plate margins to decrease edge effects. After 72 hours of siRNA-mediated gene knockdown, the medium was removed and the cells were infected with the Influenza A/Puerto Rico/8/34 (PR8, ATCC VR-1469), at an MOI of approximately 0.2-0.3 in 40 uL complete media. After 12 hours, the media was removed and the cells were then fixed with 4% formalin and stained with purified anti-HA monoclonal antibody as a marker for viral infection (Hybridoma HA36-4-5.2, Wistar Institute), followed by an Alexa Fluor 488 goat anti-mouse secondary at 1:1,000 (A11001, Invitrogen). The cells were imaged on an automated Image Express Micro (IXM) microscope (Molecular Devices), and images were analyzed using the Metamorph Cell Scoring software program (Molecular Devices Inc.). A negative control (NT, siCONTROL Non-Targeting siRNA #2, Dharmacon D-001210-02), and positive control siRNA against NXF1 (SMARTpool M-013680-01) and NP (Dharmacon custom siRNA siGenome synthesis, see below) were present on each plate. Wells containing either buffer alone, or an siRNA pool directed against Polo like kinase one (PLK1, Dharmacon) were present on all plates transfected. The screen was performed in triplicate. The results are shown in FIG. 1A.

In the primary screen, siRNA pools were classified as hits (decreased infection) if the average of the triplicate plates showed that the percentage of core positive cells was less than 55% of the plate mean, and cell number was not less than 40% of the mean of the plate. Pools that increased infection by greater than 200% of the plate mean were also selected as hits (increased infection).

The validation round screen in which the four individual oligos comprising each pool were placed into separate wells, and screened again using identical methods as above. siRNA pools were considered validated if two or more of the individual oligos scored (55% or less infected cells (decreased infection)) or 150% or greater infected cells (increased infection) as compared to the negative control wells on the plate, in either both part one and two or part two alone, and the cell number was not less than 40% of the average of the negative control wells on the plate. In some instances, transfections were done with a final concentration of 20 nM siRNA to minimize host cell toxicity while still creating a virustatic hypomorphic state. The percent of infected cells relative to controls, as well as the normalized cell numbers for each of the individual genes that confirmed with two or more siRNAs, was compared. Visual spot inspections of control images were done throughout the screen to confirm the accuracy of the automated imaging and cell scoring systems.

Figure 1B:
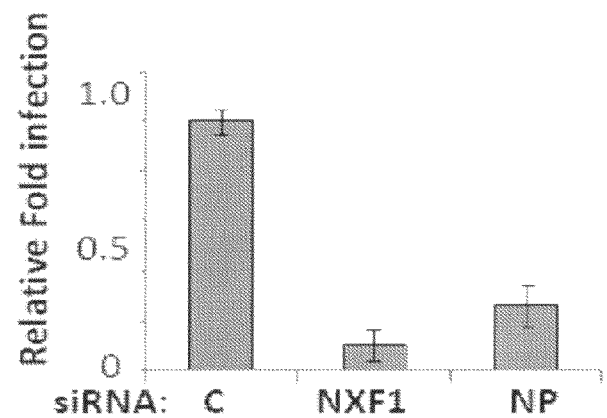
FIG. 1B is a bar graph showing the results of quantification of samples in 1A. Percent infected is relative to control. Values represent the mean±SD, N=4.
Figure 1G:
FIGS. 1G, H and I are Western blots for cells in 1D, 1E and 1F. NP, siRNA targeting flu nucleoprotein, C, Non-targeting siRNA negative control. Ran levels are provided to demonstrate relative protein loading when cross-reacting bands were not present.
Figure 1H:
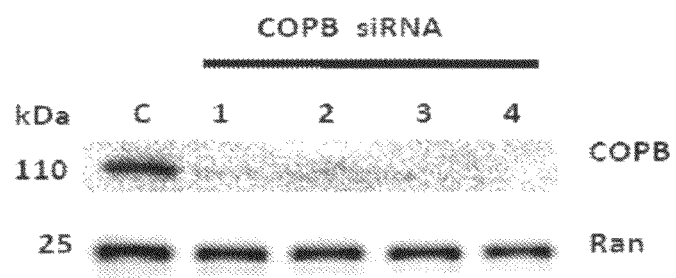
FIG. 1C is a line graph showing the results of the screen are shown with the siRNA SMARTpools ranked in order of average Z-score, from lowest (decreased infection) to highest (increased infection). The position of known influenza A virus-host factors and several newly identified genes that scored in the screen are indicated.
FIGS. 1D, E and F are each bar graphs showing the results when U2OS cells were transfected with the indicated siRNAs for 72 hours, and then infected with PR8. Twelve hours after infection the cells were analyzed by immunofluorescence (IF) for the following influenza A viral proteins, HA (surface or entire cell), NP and M2. Relative fold infection is normalized to non-targeting (C) control. Values represent the mean±SD, N=4.
Figure 1I:

This approach detected proteins needed for the following stages of the viral lifecycle: viral-host receptor binding, endocytosis and fusion of the virion, vRNP trafficking and nuclear import, the transcription, nuclear export and translation of the viral HA mRNA, and the trafficking of HA to the cell surface. In addition, anti-viral host responses might also be detected in this screen. U2OS cells were chosen for the screen because they readily express surface HA after infection with influenza A virus, are highly transfectable with siRNAs, and robustly withstand the stresses of high-throughput screening. The screen was optimized using siRNAs against NP and the host factor, NXF1, an mRNA export protein known to be required for influenza A virus infection (Ge et al., 2003; Hao et al., Nature 454, 890-893, 2008). siRNAs against either NP (GGAUCUUAUUUCCUUCG- GAGUU: SEQ ID NO:588; Ge et al., Proc Natl Acad Sci USA 100, 2718-2723, 2003)) or NXF1 (Dharmacon SMARTpool M-013680-01) resulted in inhibition of infection (NXF1 10 fold, NP 4-6 fold, FIG. 1A, 1B).

Statistical analysis of gene enrichment was performed using a hypergeometric distribution as described in the GOhyperGAll module of Bioconductor for gene ontology terms (Gentleman et al., Genome Biol 5, R80, 2004). Briefly, the R program was employed (v2.8.1) with the following command: phyper(x-1, m, n-m, k, lower.tail=FALSE), where x is the number of 1DF mapped to a specific terms; m, the total number of genes mapped to that term; n total number of unique genes in the Gene Ontology database; and k, the number of IDFs that are mapped to at least one term in the database. P-values were not corrected for multiple testing. Gene Ontology terms (v1587; May 2009) were obtained from the Gene Ontology web page (Ashbumer et al., Nat Genet. 25, 25-29, 2000) and mapping of terms to genes were obtained from the NCBI Gene database (Mar. 17, 2009). This analysis was also applied to KEGG Pathways (Kanehisa et al., Nucleic Acids Res 32, D277-280, 2004), Reactome (Vastrik et al., Genome Biol 8, R39, 2007) and protein interactions. Each pathway, reaction, event or the number of interactions for each proteins were essentially treated as a Gene Ontology term for the purpose of statistical analysis.

The selection criteria were fulfilled by 312 pools (1.7% of the total genes screened, FIG. 1C). Pools that increased HA expression by greater than 200% of the plate mean were also selected for validation (22 pools, 0.1%). The four unique siRNAs from each pool were then rescreened separately. In this validation screen, 260 out of 334 total pools (78%) confirmed with at least one siRNA scoring, and 133 candidates (40%) confirmed with two or more siRNAs, lowering the possibility of off-target effects [OTEs (Echeverri et al., Nat Methods 3, 777-779, 2006)]. Thus, bioinformatics were employed to identify networks and enriched gene sets, using a starting pool of the genes that confirmed by decreasing infection with one or more siRNAs in the validation round.

Figure 2:
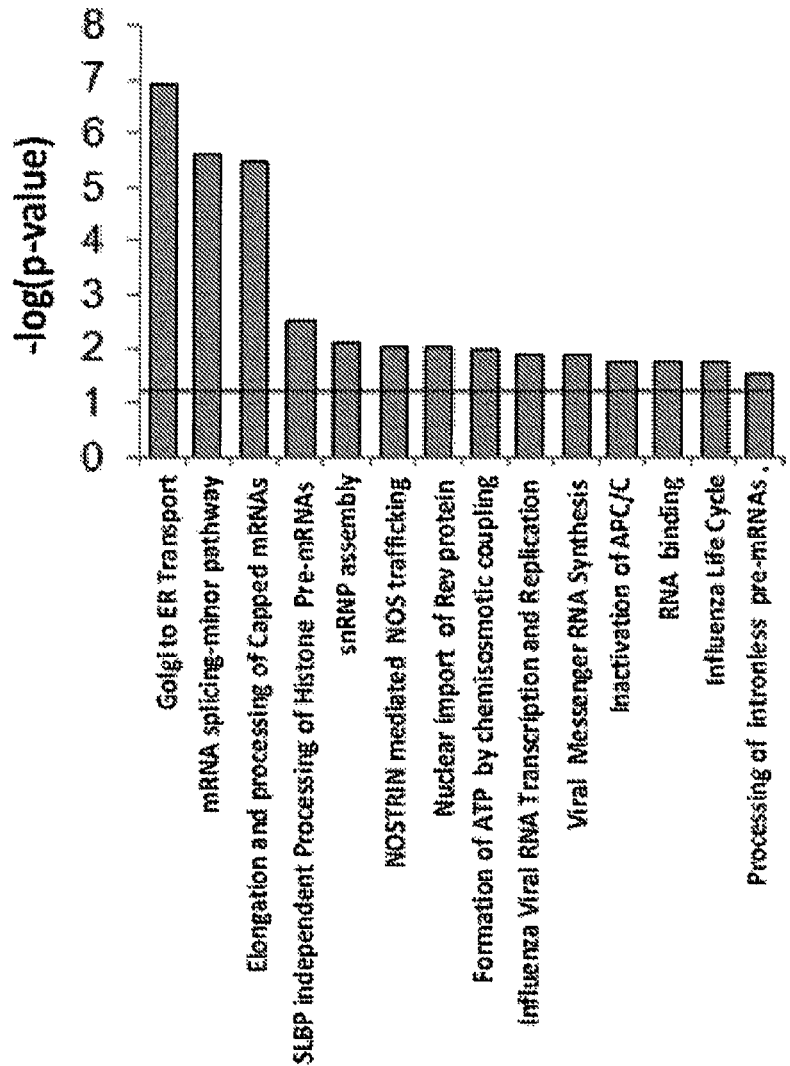
FIG. 2 shows the results of molecular function analysis for candidate genes found in the siRNA screen for influenza A virus host factors. The significance threshold is indicated by a black line at 1.3=−log(P=0.05).

The subcellular localization, gene ontology (GO) biological processes, and molecular functions of the candidates were analyzed. Ninety two GO biological process terms, assigned to 109 genes, were significantly enriched. Of these, 17 terms were non-redundant and assigned to less than 500 human genes, suggesting they were informative and specific. The most significant terms included RNA splicing (22 genes, p=2e-12), proton transport (7 genes, p=2e-5) and mRNA transport (4 genes, p=9e-3, FIG. 2). Analysis of GO molecular functions identified enrichment for 60 statistically significant terms assigned to 152 genes. Twelve terms were non-redundant and assigned to less than 500 human genes. The most significant terms included RNA binding (15 genes, p=0.014), ATPase activity (6 genes, p=0.008), and NADH dehydrogenase activity (4 genes, p=0.016).

Multiple biological pathways and macromolecular complexes were also detected, concordant with known elements of the viral lifecycle. A map of the viral lifecycle was created by connected keywords. Genes were mapped to these keywords using a database that integrates annotation information from UniProt (Bairoch et al., Nucleic Acids Res 33, D154-159, 2005), KEGG (Kanehisa et al., Nucleic Acids Res 32, D277-280, 2004), Reactome (Vastrik et al., 2007, supra), Gene Ontology (Ashbumer et al., 2000, supra), NCBI GeneRIF (Mitchell et al., AMIA Annu Symp Proc, 460-464, 2003) and OMIM Human orthologs were mapped to other species using NCBI HomoloGene (Wheeler et al., Nucleic Acids Res 33, D39-45, 2005) and annotations information from these species was used to infer function of human genes.

Genes were linked to the lifecycle keywords computationally and for each gene the information was reviewed and the mapping was refined manually. In addition protein interaction were used to map additional genes to genes present in the lifecycle map as long as no conflicting evidence was found for the interaction (e.g., different localization). Protein interactions were obtained from the Human Protein Reference Database (Wheeler et al., 2005, supra), The Biomolecular Interaction Network Database (Bader et al., Nucleic Acids Res 29, 242-245, 2001) and BioGrid (Stark et al., Nucleic Acids Res 34, D535-539, 2006). Protein interactions in human as well as in other species were considered.

Influenza A viral infection depends on sialic acid residues on the host cell surface, and depletion of the sialic acid transporter, SLC35A1, decreased infection. Consistent with work showing that influenza virus traffics through both early and late endosomes (Sieczkarski and Whittaker, Traffic 4, 333-343, 2003), the screen confirmed the functional role of two small GTPases, RAB5A (surface internalization to early endosome trafficking) and RAB7L1 (early to late endosome trafficking), for viral infection (Somsel Rodman and Wandinger-Ness, J Cell Sci 113 Pt 2, 183-192, 2000). In agreement with Hao et. al., lowering RAB10 levels inhibited infection (Hao et al., Nature 454, 890-893, 2008). RAB10 regulates the movement of endosomes generated from endocytosis downstream of RAB5 (Chen et al., Mol Biol Cell 17, 1286-1297, 2006; Glodowski et al., Mol Biol Cell 18, 4387-4396, 2007). Consistent with the virus depending on a low pH for fusion, loss of any one of four subunits of the multimeric vacuolar-ATPase proton pump (e.g., ATP6AP1, ATP6V0B, ATP6V1G1, ATP6V0E2) impeded infection (Marshansky and Futai, Curr Opin Cell Biol 20, 415-426, 2008). Once released from the endosome, the vRNPs are transported into the nucleus though the NPC (Boulo et al., Virus Res 124, 12-212007; Buss and Stewart, J Cell Biol 128, 251-261, 1995; Clarkson et al., J Mol Biol 263, 517-524, 1996). Nuclear transport factors recovered in the screen include, NUTF2, NUPL1, NUP88, NUP98, and NUP107.

Several splicing complexes were needed for flu replication, including three components of the U2 small nuclear RNP (snRNP), SF3B1, 2 and 3, and the U2 snRNP-interacting proteins, PRPF8, PTBP1, and FUS. Flu infection also required several members of the U4/U6.U5 tri-snRNP, including SART1, the human homolog of the yeast splicing factor, snu66p, which recruits the tri-snRNP to the pre-spliceosome (Makarova et al., EMBO J. 20, 2553-2563, 2001; Stevens et al., RNA 7, 1543-1553, 2001). Four out of four siRNAs targeting SART1 reduced influenza A viral infection, and decreased SART1 protein levels equivalently (FIG. 1D). SART1 depletion resulted in lower levels of HA (surface-expressed and total protein), NP and M2 proteins (FIG. 1D). Consistent with its splicing function, SART1 loss affected the levels of the M2 protein to a relatively greater extent than that of HA and NP, based on immunoflourescence (IF) staining. However, the decreased levels of all thee viral proteins, products of both spliced (M2) and unspliced (HA, NP) messages, suggests a general block in viral protein production with loss of SART1. SART1 siRNAs were as follows: SART1-1 (Dharmacon D-017283-01; Target sequence CCGAAUACCU-CACGCCUGA (SEQ ID NO:589)); SART1-2 (Dharmacon D-017283-02; Target sequence GCAAGAGCAUGAACGC-GAA (SEQ ID NO:590)); SART1-3 (Dharmacon D-017283-03; Target sequence GCUACAAACCCGACGUUAA (SEQ ID NO:591)); and SART1-4 (Dharmacon D-017283-04 (Target sequence GAACCGAUCGUGAAUAGGG (SEQ ID NO:592)).

The vesicular transport complex, coatomer 1 (COP1), also scored with multiple components in this screen (p-value=1e-7). COP1 directs both retrograde intra-Golgi and Golgi to ER transport (Cai et al., 2007). Depletion of six of seven components of COPI (ARCN1, COPA, COPB1, COPB2, COPG, and COPZ1), inhibited HA surface expression, perhaps by interfering with secretion of the host cell receptor(s) and/or trafficking of HA protein to the cell surface. Three or more independent siRNAs were confirmed in the validation round for COPA1, COPB1, COPG and COPZ. Lower COPB1 levels decreased the levels of the viral NP and M2 proteins, and had a somewhat greater effect on surface expressed versus total HA levels, suggesting that less HA arriving at the cell surface was partly responsible for the observed phenotype (FIG. 1E). COPB1 reduction by all four siRNAs correlated with the inhibition of infection (FIG. 1E, H). CALCOCO2 (NDP52) was also required for infection (FIG. 1F, I). Like COPB1, CALCOCO2 localizes to the Golgi where it interacts with the host proteins TR6BP and Myosin VI and may function in regulating secretion (Morriswood et al., J Cell Sci 120, 2574-2585, 2007). COPB1 siRNAs were as follows: COPB1-1 (Dharmacon D-017940-01; Target sequence CGACACAGC-UAUGUUAGAA (SEQ ID NO:9)); COPB1-2 (Dharmacon D-017940-02, Target sequence UAUAAGGUCUGU-CAUGCUA (SEQ ID NO:10)); COPB1-3 (Dharmacon D-017940-03, Target sequence CCUCAUGACUUCG-CAAAUA (SEQ ID NO:12)); and COPB1-4 (Dharmacon D-017940-04; Target sequence GCUGUUACCGGC-CAUAUAA (SEQ ID NO:11)). CALCOCO2 siRNAs were as follows: CALCOCO2 (Dharmacon D-010637-01, Target sequence GACAAGAUCUUCCCAGCUA (SEQ ID NO:231)); CALCOCO2 (Dharmacon D-010637-03, Target sequence GAAGACAACCCGUGAGUAU (SEQ ID NO:230)); CALCOCO2 (Dharmacon D-010637-04; Target sequence CCAAGGAUGAUGAGUAUUA (SEQ ID NO:229)); and CALCOCO$_2$ (Dharmacon D-010637-17, Target sequence AGACUGAGUGAGAACGAAA (SEQ ID NO:593)).

Protein levels were evaluated in the above using Western analysis as follows. Whole-cell extracts were prepared by cell lysis, equivalent protein content boiled in SDS sample buffer, resolved by SDS/PAGE, transferred to Immobilon-P membrane (Millipore), and probed with the indicated antibodies. Rabbit anti-SART1 was from Bethyl (A301-423A); mouse monoclonal anti-COPB1 (M3A5) from Dr. Victor Hsu (Brigham and Women's Hospital); Purified Rabbit polyclonal to IFITM3 was from Abgent (Cat #AP1153a, along with the corresponding blocking peptide Cat #BP1153); with an additional independent anti-sera from Abcam (#ab74669); mouse purified polyclonal to CALCOCO2 was from Abnova (Cat #H00010241-B01p); mouse monoclonal anti-Ran was from BD Biosciences (610340); monoclonal Anti-HA7 from Sigma-Aldrich (Product code H 3663).

To provide a more integrated view of influenza A virus-host interactions, the functional genomic results of this study were compared with the fly-based genetic screen, and the literature mining data of the Reactome project (Matthews et al., Nucleic Acids Res. 2009 January; 37(Database issue):D619-22. Epub 2008 Nov. 3). Reactome is an expertly-curated resource of human biologic pathways, including the host-viral interactions occurring during influenza A virus infection. The resulting protein network extension analysis provided functional support for the role of six host factors in the Reactome influenza A virus infection pathway (p. 027), and revealed first-order (direct) interactions between 37 host factors found in this screen and those listed in the Reactome (p=0.007). To identify potential key intermediates, human and fly host factors detected in the RNAi screens were used to select proteins that are significantly (p<0.05) connected given the number of their known interactors. Fourteen proteins were predicted as potentially important in the flu lifecycle, including the RNA helicase DHX15, the nuclear transporter TNPO2 and the mRNA surveillance and export protein UPF3A. Such testable hypotheses of possible host-viral "nodes and edges" will likely continue to emerge as comprehensive screening efforts and meta-analyses are completed.

A list of those proteins, deletion of which resulted in decreased Influenza A infection, and that were not redundant with the fly screen or Reactome is given in Table 1.

TABLE 1

Decreased Influenza A Infection

| Gene Symbol | Gene ID | Accession Number | siRNA sequence | SEQ ID NO. | Dharmacon Catalog Number |
|---|---|---|---|---|---|
| ARCN1 | 372 | NM_001655.4 | GAUCAGAACCUUCACAGAA | 1. | D-013063-02 |
|  |  |  | AAACAGAGAGUGUAAGAUA | 2. | D-013063-01 |
|  |  |  | UGAAAUAUCUGAGCACUGU | 3. | D-013063-04 |
|  |  |  | GACGGAGGAUUACAGAAUA | 4. | D-013063-03 |
| COPA | 1314 | NM_004371.3 | ACUCAGAUCUGGUGUAAUA | 5. | D-011835-01 |
|  |  |  | GAGUUGAUCCUCAGCAAUU | 6. | D-011835-04 |
|  |  |  | GCAAUAUGCUACACUAUGU | 7. | D-011835-02 |
|  |  |  | GAUCAGACCAUCCGAGUGU | 8. | D-011835-03 |
| COPB1 | 1315 | NM_016451.4 | CGACACAGCUAUGUUAGAA | 9. | D-017940-01 |
|  |  |  | UAUAAGGUCUGUCAUGCUA | 10. | D-017940-02 |
|  |  |  | GCUGUUACCGGCCAUAUAA | 11. | D-017940-04 |
|  |  |  | CCUCAUGACUUCGCAAAUA | 12. | D-017940-03 |
| COPB2 | 9276 | NM_004766.2 | GAAGGGAGCAUCAUUGUUA | 13. | D-019847-02 |
|  |  |  | UAUGGGCAGUUGUGAAAUA | 14. | D-019847-05 |
|  |  |  | GGACACACCCAUUAUGUUA | 15. | D-019847-04 |
|  |  |  | CAACAGCAUUGUAAAGAUA | 16. | D-019847-03 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| COPZ1 | 22818 | NM_016057.1 | CCAAAGAACAGAUCAAGUG | 17. | D-020293-01 |
|  |  |  | GGCUGUGGAUGAAAUUGUA | 18. | D-020293-02 |
|  |  |  | GAACCUUCCCUGUAUACUG | 19. | D-020293-03 |
|  |  |  | CAACAAGACCCAUCGGACU | 20. | D-020293-04 |
| CYB5R4 | 51167 | NM_016230.3 | GGAACAGGCUUCACACCAA | 21. | D-009347-03 |
|  |  |  | GAAAGGAUCUAACGGGAUU | 22. | D-009347-01 |
|  |  |  | CAAAGAAGGUCCUAGUUAU | 23. | D-009347-02 |
|  |  |  | GGAUAUCAAUUUAGACUCA | 24. | D-009347-04 |
| DHX8 | 1659 | NM_004941.1 | GCAAAGAUCCAGUUGUUAA | 25. | D-010506-02 |
|  |  |  | GCACUGAGCUGGACAAUCA | 26. | D-010506-01 |
|  |  |  | GGAAUAAAGUGAAGUCUAG | 27. | D-010506-03 |
|  |  |  | GGGAUGAUGCCCAAUGAUA | 28. | D-010506-05 |
| NHP2L1 | 4809 | NM_005691.2 | CAGCAGAUCCAAUCCAUUC | 29. | D-019900-04 |
|  |  |  | GACUGAGGCUGAUGUGAAU | 30. | D-019900-03 |
|  |  |  | GAAUGUGCCCUACGUGUUU | 31. | D-019900-01 |
|  |  |  | UGAAGAAGGUGAACAGUUU | 32. | D-007316-04 |
| PRPF31 | 26121 | NM_015629.3 | GGAAGCAGGCCAACCGUAU | 33. | D-020525-02 |
|  |  |  | GAAGCAGAGCGUCGUAUAU | 34. | D-020525-03 |
|  |  |  | GCUCUUAGCUGAUCUCGAA | 35. | D-020525-01 |
|  |  |  | CGGGAUAAGUACUCAAAGA | 36. | D-020525-04 |
| PRPF8 | 10594 | NM_006445.3 | GGAAGAAGCUAACUAAUGC | 37. | D-012252-04 |
|  |  |  | GCAGAUGGAUUGCAGUAUA | 38. | D-012252-02 |
|  |  |  | UGAAGCAUCUCAUCUAUUA | 39. | D-012252-01 |
|  |  |  | GAUAAGGGCUGGCGUGUCA | 40. | D-012252-05 |
| SART1 | 9092 | NM_005146.4 | GCUACAAACCCGACGUUAA | 41. | D-017283-03 |
|  |  |  | GAACCGAUCGUGAAUAGGG | 42. | D-017283-04 |
|  |  |  | GCAAGAGCAUGAACGCGAA | 43. | D-017283-02 |
|  |  |  | CCGAAUACCUCACGCCUGA | 44. | D-017283-01 |
| SLU7 | 10569 | NM_006425.4 | GUGGAGUACUCAAGACAUG | 45. | D-017191-04 |
|  |  |  | GGAGCCAAAUUUACAGGUA | 46. | D-017191-03 |
|  |  |  | CGAAAGAGCAGUUCAGAUA | 47. | D-017191-01 |
|  |  |  | GGAAGGAGAUUGUUAACUC | 48. | D-017191-02 |
| SNRPB | 6628 | NM_003091.3 | GGACCUCCUCCCAAAGAUA | 49. | D-017766-02 |
|  |  |  | CAUAUUGAUUACAGGAUGA | 50. | D-017766-03 |
|  |  |  | UAUGAGACCUCCUAUGGGU | 51. | D-017766-04 |
|  |  |  | CCAAAGAACUCCAAACAAG | 52. | D-017766-01 |
| SNRPD3 | 6634 | NM_004175.3 | CGAUUAAAGUACUGCAUGA | 53. | D-019085-03 |
|  |  |  | AUACAUCCGUGGCAGCAAA | 54. | D-019085-04 |
|  |  |  | GAACACCGGUGAGGUAUAU | 55. | D-019085-02 |
|  |  |  | GAAGAACGCACCCAUGUUA | 56. | D-019085-01 |
| THRSP | 7069 | NM_003251.2 | CAGCCGAGGUGCACAACAU | 57. | D-019569-03 |
|  |  |  | UCAUGCACCUCACCGAGAA | 58. | D-019569-02 |
|  |  |  | CCGCAGAGACAGAGGAAGU | 59. | D-019569-04 |
|  |  |  | GGAAAUGACGGGACAAGUU | 60. | D-019569-01 |
| AMOTL1 | 154810 | NM_130847.2 | ACGAGGAACUGCCCACUUA | 61. | D-017595-03 |
|  |  |  | GGAAAGGGCUUCAAAGUAG | 62. | D-017595-01 |
|  |  |  | GAAUUUCGGAAGCCUAUGA | 63. | D-017595-04 |
|  |  |  | GCAAGCAUAUGUUGAGAAA | 64. | D-017595-02 |
| ATP6AP1 | 537 | NM_001183.4 | CAAGAAGGGUAGUCUCCUC | 65. | D-021378-04 |
|  |  |  | GAAGAUGUCCCAUACACAG | 66. | D-021378-03 |
|  |  |  | GCAGCUCUCUACCUACUUA | 67. | D-021378-01 |
|  |  |  | GAACGACUCUUUGGUACCA | 68. | D-021378-02 |
| ATP6V0B | 533 | NM_004047.3 | CAUCAUGGCAAUUGUCAUU | 69. | D-010907-01 |
|  |  |  | GCAUGGUUCCUGACGGAGA | 70. | D-010907-04 |
|  |  |  | GGAACUACCAUGCAGGCUA | 71. | D-010907-02 |
|  |  |  | GUGAGGCUGUGGCCAUCUA | 72. | D-010907-03 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| ATP6V1G1 | 9550 | NM_004888.3 | UGGACAACCUCUUGGCUUU | 73. | D-013608-02 |
| | | | GCAUUGGGAUCCCGUGGCA | 74. | D-013608-04 |
| | | | UGACCAUCCUCCAGACAUA | 75. | D-013608-01 |
| | | | CAUGAAAACUACCGCAUAA | 76. | D-013608-03 |
| COPG | 22820 | NM_016128.3 | GAGGGUGGCUUUGAGUAUA | 77. | D-019138-01 |
| | | | GAAGAGGCUGUGGGUAAUA | 78. | D-019138-03 |
| | | | GCAAACACGCCGUCCUUAU | 79. | D-019138-02 |
| | | | GGAGGCCCGUGUAUUUAAU | 80. | D-019138-04 |
| CPLX1 | 10815 | NM_006651.3 | CCAAGUACGCCAAGAUGGA | 81. | D-013031-02 |
| | | | GAAGCAGGCUCUAGGAGGG | 82. | D-013031-01 |
| | | | AGGGCAUCCGAGACAAGUA | 83. | D-013031-04 |
| | | | AGAAGAAGGAGGAGCGCGA | 84. | D-013031-03 |
| CRNKL1 | 51340 | NM_016652.4 | CAAUUAUGAUGCAUGGUUU | 85. | D-019013-03 |
| | | | GAAAGGGUACGAGUGAUUU | 86. | D-019013-02 |
| | | | GAUCAAGUAUGCCCGCUUU | 87. | D-019013-01 |
| | | | CGAGCGUGCUUUAGAUGUA | 88. | D-019013-04 |
| EFTUD2 | 9343 | NM_004247.3 | AUGAUGAGUUUGGGAAUUA | 89. | D-019851-03 |
| | | | GACCAAGAUCUGUGCUAUA | 90. | D-019851-04 |
| | | | UGGAUGAGGUCAAUGGAUU | 91. | D-019851-02 |
| | | | UGGCGGAUCUGAUGGAUAA | 92. | D-019851-01 |
| ESAM | 90952 | NM_138961.2 | GCACCAGCAUUAGAUGUCA | 93. | D-016663-03 |
| | | | GGCCCACCCUCAACCAAUA | 94. | D-016663-02 |
| | | | CCAAUGAUAUCAAGGAGGA | 95. | D-016663-01 |
| | | | GCCUGGAGCUGCAGUGGUU | 96. | D-016663-04 |
| FUS | 2521 | NM_004960.3 | CGGGACAGCCCAUGAUUAA | 97. | D-009497-06 |
| | | | CCUACGGACAGCAGAGUUA | 98. | D-009497-02 |
| | | | GAUUAUACCCAACAAGCAA | 99. | D-009497-04 |
| | | | GAUCAAUCCUCCAUGAGUA | 100. | D-009497-05 |
| GJA3 | 2700 | NM_021954.3 | GGACCUACGUCUUCAACAU | 101. | D-015676-01 |
| | | NM_029726.2 | GCAGGACAAUCCCUCGUCG | 102. | D-015676-03 |
| | | | CGGAGGACUUGGCCAUCUA | 103. | D-015676-02 |
| | | NM_012317.2 | CGUCUUACAUGCUCGUGAA | 104. | D-012461-03 |
| HNRPU | 3192 | NM_004501.3 | CGUAUUGGCUGGUCACUAA | 105. | D-013501-04 |
| | | | GAACAGAAAGGCGGAGAUA | 106. | D-013501-03 |
| | | | GGAAAGACCUACCAGAACA | 107. | D-013501-01 |
| | | | GUAGAACUCUCGUAUGCUA | 108. | D-013501-02 |
| KIAA1604 | 57703 | NM_020943.2 | GAAACAAACAAGUUGCGAA | 109. | D-023101-04 |
| | | | CUUAUUAGCUGGGCGAUUU | 110. | D-023101-03 |
| | | | GGAAUGUGGCCUCAAAUUA | 111. | D-023101-01 |
| | | | AAAUUAACCUGGUCUCAUU | 112. | D-023101-02 |
| MFAP1 | 4236 | NM_005926.2 | AAGUGAAGGUAAAGCGUUA | 113. | D-020071-03 |
| | | | GCUCAGGUCGCACCAAAUA | 114. | D-020071-02 |
| | | | UAUGAGGCAUGGAAAGUUC | 115. | D-020071-04 |
| | | | GGAGAAAGCAGAAAUUGAA | 116. | D-020071-01 |
| MGC2452 | 84730 | NM_005036.4 | GCUGGUACCUCUUCAACAG | 117. | D-014948-03 |
| | | | GGGGAAAGCUGGCCACCUU | 118. | D-014948-04 |
| | | | GCUCUGGGCAGCUUUCAAA | 119. | D-014948-02 |
| | | | GCCCACAGCUCACCACCUA | 120. | D-014948-01 |
| NDUFB8 | 4714 | NM_005004.2 | GUAUGCAGCUCUUCGGUUU | 121. | D-019898-03 |
| | | | CCGCCAAGAAGUAUAAUAU | 122. | D-019898-04 |
| | | | UGAGAGAGAUCCAUGGUAU | 123. | D-019898-02 |
| | | | GACCAAAGCAGUAUCCUUA | 124. | D-019898-01 |
| NUTF2 | 10204 | NM_005796.1 | CAACGAUGCUUUGGGUUUGC | 125. | D-012132-04 |
| | | | GGGGAAAGCUGCCAUUGUG | 126. | D-012132-03 |
| | | | CAGAUUGGAUCCAGCUUCA | 127. | D-012132-01 |
| | | | CGUCAUGCCUUACGUGGGA | 128. | D-012132-02 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| PGD | 5226 | NM_002631.2 | GAUCAUCUCUUACGCUCAA | 129. | D-008371-01 |
| | | | GAAAUCACAGCCAAUAUUC | 130. | D-008371-03 |
| | | | UAAUAGGACUGUCUCCAAA | 131. | D-008371-02 |
| | | | GAAAUUGGUACCAUUGUUG | 132. | D-008371-04 |
| PRRT1 | 80863 | NM_030651.3 | CCACACGACUACAUGCCCA | 133. | D-016655-04 |
| | | | GCAUGCCACCCGACCCUUA | 134. | D-016655-02 |
| | | | CUGCUUACGUGCCGGUCUA | 135. | D-016655-03 |
| | | | GAACUACUGGGAUCCCUAA | 136. | D-016655-01 |
| PRSS8 | 5652 | NM_002773.3 | CCAGCGAGCACCACAAGGA | 137. | D-003696-02 |
| | | | GUAACUGCCUGUACAACAU | 138. | D-003696-01 |
| | | | CGACAUUGCACUCCUCCAA | 139. | D-003696-04 |
| | | | GUGGCUCUCUCGUGUCUGA | 140. | D-003696-03 |
| RBM14 | 10432 | NM_006328.3 | CUACGACGAUCCCUACAAA | 141. | D-020144-04 |
| | | | GAGCUGCGCCGUCAUGAAA | 142. | D-020144-03 |
| | | | UAGCCGAGCUCUCUGAUUA | 143. | D-020144-01 |
| | | | CCAGGCAGCUUCAUAUAAU | 144. | D-020144-02 |
| SF3B1 | 23451 | NM_012433, NM_001005526.1 | GGAUACGUGACAUCAAUUG | 145. | D-020061-08 |
| | | | CGAGUUUGCUUGGUCAGAA | 146. | D-020061-07 |
| | | | GGAGUGGGCCUCGAUUCUA | 147. | D-020061-06 |
| | | | CGAGUUUGCUUGGUCAGAA | 148. | D-020061-07 |
| SF3B2 | 10992 | NM_006842.2 | UGACAUCGACUACCAGAAA | 149. | D-026599-03 |
| | | | GGACAAAGCCGCUCCACCU | 150. | D-026599-04 |
| | | | GAGAGAAAGUUCGGCCUAA | 151. | D-026599-01 |
| | | | UAUGACAUGUCCACGGUUA | 152. | D-026599-02 |
| SF3B3 | 23450 | NM_012426.4 | GAUAUCCGCUGUCCAAUUC | 153. | D-020085-02 |
| | | | GCCAAGGACCUGAUACUAA | 154. | D-020085-04 |
| | | | GGACAUAGGGUAAUUGUAU | 155. | D-020085-01 |
| | | | UAGCUGAUCUGGCCAAUGA | 156. | D-020085-03 |
| SLC2A2 | 6514 | NM_000340 | GGACUAUAUUGUGGGCUAA | 157. | D-007515-05 |
| | | | GAGCAGAAAGUCUCUAUAA | 158. | D-007515-01 |
| | | | GCAUGUGGCUCAGCAAUUU | 159. | D-007515-04 |
| | | | GAAAAGCUAUCAACAACUA | 160. | D-007515-03 |
| SNRPD2 | 6633 | NM_004597.5 | GAUAGGCACUGCAACAUGG | 161. | D-013617-01 |
| | | | UCAAGAACAAUACCCAAGU | 162. | D-013617-03 |
| | | | AUCAACUGCCGCAACAAUA | 163. | D-013617-04 |
| | | | UCAACAAGCCCAAGAGUGA | 164. | D-013617-02 |
| UBL5 | 59286 | NM_024292.3 | AAGAAGUGGUACACGAUUU | 165. | D-014320-03 |
| | | | GAACCUGGAGCUUUAUUAU | 166. | D-014320-02 |
| | | | GGACUAUGAAAUCCACGAU | 167. | D-014320-04 |
| | | | GGAAGAAGGUCCGCGUUAA | 168. | D-014320-01 |
| YTHDC1 | 91746 | NM_133370.2 | CAAGACAACUGGUUUCUAA | 169. | D-015332-01 |
| | | | CAGAGAACCUUAUAAGAAU | 170. | D-015332-03 |
| | | | GAAUGAACAUAAACCAGUA | 171. | D-015332-02 |
| | | | GGAAUUUCAUAACAUGGGA | 172. | D-015332-04 |
| ZNF16 | 7564 | NM_006958.2 | AAACUAUGCUGGUGAUGUU | 173. | D-012773-01 |
| | | | AUACUGAGCUGGAAGCCAU | 174. | D-012773-04 |
| | | | ACAAGGAGUUUCUUCACAA | 175. | D-012773-02 |
| | | | GCUGAAAGUCCACUCAUAU | 176. | D-012773-03 |
| ZNF552 | 79818 | NM_024762.3 | GCCGAAAGCUCCAGUCUCA | 177. | D-014438-02 |
| | | | GCGAAGAGGUGUAAGUUGC | 178. | D-014438-03 |
| | | | CCAAAGAUAUACUCAGUCA | 179. | D-014438-01 |
| | | | CUACAUUCCGUGUUCAUAA | 180. | D-014438-04 |
| ABCD1 | 215 | NM_000033.3 | CAAGUACGCCCUCCUGGAU | 181. | D-009605-03 |
| | | | CGGAGGAGAUCGCCUUCUA | 182. | D-009605-04 |
| | | | GUUCAGCGCUGUCACUUCA | 183. | D-009605-02 |
| | | | GAACGCCUGUGGUAUGUUA | 184. | D-009605-01 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| AHCY | 191 | NM_000687.2 | GGACCCAUCCAGACAAGUA | 185. | D-009599-04 |
| | | | UCAAGUGGCUCAACGAGAA | 186. | D-009599-02 |
| | | | GCGAAACGGACGAGGAGUA | 187. | D-009599-05 |
| | | | GAGCAGACCCUGUACUUCA | 188. | D-009599-03 |
| ANGPTL3 | 27329 | NM_014495.2 | GAACUCAACUCAAAACUUG | 189. | D-007806-02 |
| | | | GAGAAGAUAUACUCCAUAG | 190. | D-007806-03 |
| | | | GAACUACUCCCUUUCUUCA | 191. | D-007806-04 |
| | | | UAACAGAGGUGAACAUACA | 192. | D-007806-01 |
| ATP5F1 | 515 | NM_001688.4 | CGCCUGGACUAUCAUAUAU | 193. | D-015956-04 |
| | | | AGAAUGCAAUUGAUACGGA | 194. | D-015956-03 |
| | | | GGGAACGACUGUAUAGAGU | 195. | D-015956-02 |
| | | | GAACUGGGCUUAUCUUGUA | 196. | D-015956-01 |
| ATP6V0E2 | 155066 | NM_001100592.1 | GUGCCCAGCUCUCGGAAUG | 197. | D-025369-03 |
| | | | GGGAUGUCCUGCUCCAAUA | 198. | D-025369-01 |
| | | | CCACCGCCGUCUGCUGUUA | 199. | D-025369-02 |
| | | | GGUGGGGUCUUUCCCUUUA | 200. | D-025369-04 |
| B4GALT2 | 8704 | NM_003780.3 | UCAGAGGUUUACCAAGAUU | 201. | D-011518-03 |
| | | | CAACCACUCUUCACCAAUA | 202. | D-011518-01 |
| | | | CGACAAGCAUAACGAACCU | 203. | D-011518-04 |
| | | | GAAGGAGGAUGCCGCCUAU | 204. | D-011518-02 |
| BACE1 | 23621 | NM_012104.3 | CGAAUUGGCUUUGCUGUCA | 205. | D-003747-03 |
| | | | GGAGAUCAAUGGACAGGAU | 206. | D-003747-02 |
| | | | AGACGACUGUUACAAGUUU | 207. | D-003747-01 |
| | | | GCACCGACCUGGUAAGCAU | 208. | D-003747-04 |
| BIRC4 | 331 | NM_001167.2 | GAGGAACCCUGCCAUGUAU | 209. | D-004098-03 |
| | | | GAGGAGGGCUAACUGAUUG | 210. | D-004098-02 |
| | | | GCACGGAUCUUUACUUUUG | 211. | D-004098-04 |
| | | | GAACUGGGCAGGUUGUAGA | 212. | D-004098-05 |
| C16orf24 | 65990 | NM_023933.1 | GCAAGGAUCUCUGGAAGGU | 213. | D-014255-01 |
| | | | AGUAUGGGCUUAUGAUGUU | 214. | D-014255-02 |
| | | | CAACGUGUCUGUGUUCCUG | 215. | D-014255-03 |
| | | | GAGCACGUGUUGUCGCUGC | 216. | D-014255-04 |
| C19orf29 | 58509 | NM_001080543.1 | GGACAUCGCUUUCAAGAUC | 217. | D-031204-01 |
| | | | CGGGAGCGCAGGUCAGAUU | 218. | D-031204-04 |
| | | | GCGCAGGCUUCGGCUAUUG | 219. | D-031204-03 |
| | | | CCAAGAUCGUGCAGGGAUA | 220. | D-031204-02 |
| C22orf15 | 150248 | NM_182520.2 | GCAGGUGAGUGUCAGGGUA | 221. | D-018678-03 |
| | | | GGGCACACCUUCUCCCUAA | 222. | D-018678-01 |
| | | | GAGCAAAGCCCCACUUCAA | 223. | D-018678-04 |
| | | | GAACCUGGAUGACCAUUAC | 224. | D-018678-02 |
| CADM2 | 253559 | NM_153184.3 | GGAUUCUCAUCACCAGUUA | 225. | D-016035-03 |
| | | | GAAAUACACUAUACACCAU | 226. | D-016035-02 |
| | | | GGCAUAAAGGAACGUAUUU | 227. | D-016035-04 |
| | | | UGGCAUGAAUUGAGUAUUA | 228. | D-016035-01 |
| CALCOCO2 | 10241 | NM_005831.3 | CCAAGGAUGAUGAGUAUUA | 229. | D-010637-04 |
| | | | GAAGACAACCCGUGAGUAU | 230. | D-010637-03 |
| | | | GACAAGAUCUUCCCAGCUA | 231. | D-010637-01 |
| | | | GAAUGAAACUACUGCAAUG | 232. | D-010637-02 |
| CCDC74A | 90557 | NM_138770.1 | UCAAGUCCAUCUCUAAUUC | 233. | D-016548-02 |
| | | | GAAGAAAGAUGGCCCCUCA | 234. | D-016548-04 |
| | | | GAACAACUUUGCCGAGAGG | 235. | D-016548-03 |
| | | | AAACAAGGAUCUCCAUUAC | 236. | D-016548-01 |
| CCDC74B | 91409 | NM_207310.1 | GAACAACUUUGCCGAGAGG | 237. | D-022933-02 |
| | | | AAACAAGGAUCUCCGUUAC | 238. | D-022933-04 |
| | | | GAAGAAAGAUGGCCCCUCA | 239. | D-022933-03 |
| | | | UCAAGUCCAUCUCUAAUUC | 240. | D-022933-01 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| CHMP2B | 25978 | NM_014043.3 | GAAGAUGGCUGGAGCAAUG | 241. | D-004700-01 |
| | | | GCCAGGAUAUUGUGAAUCA | 242. | D-004700-04 |
| | | | UAAGGAAGCUUGCAAAGUU | 243. | D-004700-02 |
| | | | GCUCGAAGCUUACCAUCUG | 244. | D-004700-03 |
| FLJ25416 | 220042 | NM_I 45018.3 | ACACAGAGCUAUUCUAUUG | 245. | D-007159-03 |
| | | | GAAGAGAUAUGUCAGAAUA | 246. | D-007159-01 |
| | | | GCAAUGCUCUGACCACAAA | 247. | D-007159-04 |
| | | | GAAUGGAUGUGGAGAAAUA | 248. | D-007159-02 |
| CXorf59 | 286464 | NM_173695.1 | UAUAAGAGGUGGAUUGAAA | 249. | D-018043-01 |
| | | | GAGAAUACUCGACAUGUGA | 250. | D-018043-02 |
| | | | GGAGAUGGAUGCAGGAGUC | 251. | D-018043-03 |
| | | | CUGCACAAUUGCCUGAUUA | 252. | D-018043-04 |
| TPRX1 | 284355 | NM_198479.2 | GUUAUUCCCUCACUUCACA | 253. | D-027234-01 |
| | | | GCUCAGAUCCCAAGCCCGA | 254. | D-027234-03 |
| | | | AGGCCCAGGUCCCAUCUUA | 255. | D-027234-02 |
| | | | GGGAUGACUCUAUGGGCAA | 256. | D-027234-04 |
| CLK3 | 1198 | NM_001130028.1 NM_003992.4 | GGACUACUAUGGACCUUCA | 257. | D-004802-03 |
| | | | GAGCGGAGCCCAUCCUUUG | 258. | D-004802-04 |
| | | | GAACCAGACCCGUACCUGA | 259. | D-004802-05 |
| | | | GCAAGAACACCUUUGAGUU | 260. | D-004802-02 |
| CLN5 | 1203 | NM_006493.2 | UAACAAGUUGGCUGAAUUU | 261. | D-020163-04 |
| | | | AGACAUGGUUUGAUUCCUA | 262. | D-020163-03 |
| | | | GAAAUCCCUUUUACCUAUCA | 263. | D-020163-01 |
| | | | GACAUUAGUUCAAGUAGCA | 264. | D-020163-02 |
| CNTN5 | 53942 | NM_014361.2 | GAAAGUGUCCCUCCUCUUA | 265. | D-007858-01 |
| | | | GCCAGUAUCUGAAGAGUUU | 266. | D-007858-03 |
| | | | UCACAUGGAUGAAGGUUAA | 267. | D-007858-04 |
| | | | GCAAUCCAGUUCCCAGUUA | 268. | D-007858-02 |
| CRADD | 8738 | NM_003805.3 | ACGGAUAUCUACCGCUGUA | 269. | D-004412-01 |
| | | | GGCCAGAGACAAACAAGUA | 270. | D-004412-02 |
| | | | ACAAUGCUCCUGCUGGAUA | 271. | D-004412-03 |
| | | | UAGAUUCCCUACAGGAGUU | 272. | D-004412-04 |
| DCLRE1B | 64858 | NM_021036.2 | ACUCUGACCAUUCCUCUUA | 273. | D-015780-03 |
| | | | GAAAACACCCACAACAUAA | 274. | D-015780-02 |
| | | | CGGACUCUGUACAGCAAUA | 275. | D-015780-04 |
| | | | GGAAGAUGGUUGGCGACGU | 276. | D-014116-01 |
| DKFZp434N035 | 84222 | NM__032262.1 | GGAUCUUGCUCAUGUAUUU | 277. | D-014823-01 |
| | | | GCUCUAGGCAUACCACAUA | 278. | D-014823-03 |
| | | | GCAGCUAGCUUCGAUUGUU | 279. | D-014823-02 |
| | | | GGACGAGUUUACCUACAGU | 280. | D-014823-04 |
| DMD | 1756 | NM_000109.3 | CAAGACAGUUGGGUGAAGU | 281. | D-011809-04 |
| | | | GAAUGUUUAUGAUACGGGA | 282. | D-011809-01 |
| | | | GUCAGAUUCUCAGCUUAUA | 283. | D-011809-03 |
| | | | GCAAGUGGCAAGUUCAACA | 284. | D-011809-02 |
| DSC3 | 1825 | NM_001941.3 | AGACAUGGAUGGCCAGUUU | 285. | D-003651-04 |
| | | | UAAAGCCACUGAAUUAUGA | 286. | D-003651-01 |
| | | | GAAAGUAGUAGACCUGGUA | 287. | D-003651-02 |
| | | | GAACUAUACUGUCUUCUAC | 288. | D-003651-03 |
| DYNC111 | 1780 | NM_004411.4 | GACAAUCGCAGUCAUCGAA | 289. | D-019799-03 |
| | | | CAAGGGAAGUAGUGUCCUA | 290. | D-019799-02 |
| | | | GGAAAUUCGUGCUAACAGA | 291. | D-019799-01 |
| | | | CGGGAGACGUCAAUAACUU | 292. | D-019799-04 |
| EPRS | 2058 | NM_004446.2 | GUAAUCUCUGUAUGAUGA | 293. | D-008245-01 |
| | | | GGAAACUGAUCAUGAGAUU | 294. | D-008245-04 |
| | | | GAAGAGGGAUGACAGUUGA | 295. | D-008245-03 |
| | | | GAAGAAAGCUCCAGUUCAU | 296. | D-008245-02 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| EVC2 | 132884 | NM_147127.4 | GAACAGUGUCGUGCUAGAA | 297. | D-018291-03 |
|  |  |  | UAACACACCGCCUGUAUGG | 298. | D-018291-04 |
|  |  |  | GGAGUACGAUCGGAAGAUG | 299. | D-018291-01 |
|  |  |  | AGACGAGAGUUGCUACAAA | 300. | D-018291-02 |
| FAM38A | 9780 | NM_001142864.2 | UCGCGGUGGUCGUCAAGUA | 301. | D-020870-03 |
|  |  |  | GCAAGUUCGUGCGCGGAUU | 302. | D-020870-04 |
|  |  |  | AAAGACAGAUGGAGCGUAU | 303. | D-020870-01 |
|  |  |  | GCAAGACCGUGCUGGGCAA | 304. | D-020870-02 |
| FCGR2A | 2212 | NM_021642.3 | CCACCUGGACGUCAAAUGA | 305. | D-014152-04 |
|  |  |  | CAACAAUGACUAUGAAACA | 306. | D-014152-03 |
|  |  |  | GGGCAGCUCUUCACCAAUG | 307. | D-014152-02 |
|  |  |  | UGUGAAGGCUGCCCAAUUU | 308. | D-014152-01 |
| GDPD5 | 81544 | NM_030792.6 | AUACAUCGCUGGCCUCCUG | 309. | D-019423-03 |
|  |  |  | GAUGUGCUCUCCGUAUGUU | 310. | D-019423-02 |
|  |  |  | GCUACAACCCUGAGCAGAU | 311. | D-019423-04 |
|  |  |  | GGACGAGUACUGUCUCAUG | 312. | D-019423-01 |
| GINS2 | 51659 | NM_016095.2 | CUGGAUAACUUGACCUUGA | 313. | D-020418-01 |
|  |  |  | CCUGUUAAAUCAUGCUUCA | 314. | D-020418-04 |
|  |  |  | GGACACUCGUAUAGCCAAA | 315. | D-020418-02 |
|  |  |  | CCCUGUGGCUGGCGAUUAA | 316. | D-020418-03 |
| GPKOW | 27238 | NM_015698.3 | GAACGGAACUGCCUCAUCA | 317. | D-015129-01 |
|  |  |  | GGACCUGCGUGUGCGGUUU | 318. | D-015129-04 |
|  |  |  | ACACCAAGAUGAUAAUUGA | 319. | D-015129-02 |
|  |  |  | UGCCAGAGGAGGCUAAUUA | 320. | D-015129-03 |
| GSK3A | 2931 | NM_019884.2 | GAACCCAGCUGCCUAACAA | 321. | D-003009-06 |
|  |  |  | GCUCUAGCCUGCUGGAGUA | 322. | D-003009-08 |
|  |  |  | GGACAAAGGUGUUCAAAUC | 323. | D-003009-05 |
|  |  |  | GCGCACAGCUUCUUUGAUG | 324. | D-003009-07 |
| HRK | 8739 | NM_003806.1 | GCUCAAGGCGCUAGGCGAC | 325. | D-008216-01 |
|  |  |  | UAGGCGACGAGCUGCACCA | 326. | D-008216-04 |
|  |  |  | UCAAGGCGCUAGGCGACGA | 327. | D-008216-05 |
|  |  |  | CUGCUCGGCAGGCGGAACU | 328. | D-008216-03 |
| INMT | 11185 | NM_006774.4 | GCUGUAGCCUUGAUGCCUA | 329. | D-015314-03 |
|  |  |  | GGGACUACUUGGCUACUUA | 330. | D-015314-01 |
|  |  |  | CAAGUGCGAUGUCCACCUG | 331. | D-015314-04 |
|  |  |  | GCUCAGGUCCUACCAUCUA | 332. | D-015314-02 |
| IQSEC1 | 9922 | NM_014869.4 | GGAAGAAAUUCACCGAUGA | 333. | D-006458-01 |
|  |  |  | CGAGAAAUCUUCCUGUUCA | 334. | D-006458-02 |
|  |  |  | GACAGUCCUUCUCCUUGUA | 335. | D-006458-04 |
|  |  |  | GGACGAUGGUGAGGACAUU | 336. | D-006458-03 |
| LOC163233 | 163233 | XM_290865.5 | UUAACCAGCUAUCAACUUU | 337. | D-024000-01 |
|  |  |  | GGACACCUCUGCCCUUACU | 338. | D-024000-03 |
|  |  |  | GACAACUACUCAAAGCAAA | 339. | D-024000-02 |
|  |  |  | AAGCGCUCCUUUAUCCUUA | 340. | D-024000-04 |
| LOC51149 | 51149 | NM_016175.3 | CCUCAUGGGACGCAAGGAC | 341. | D-021060-04 |
|  |  |  | GCACAGAAUCCUCGACCCA | 342. | D-021060-02 |
|  |  |  | ACGACUAUGUGACCUCUUU | 343. | D-021060-01 |
|  |  |  | CGAUUUGUCCUGCCACCUA | 344. | D-021060-03 |
| LRP1B | 53353 | NM_018557.2 | GAAUAUACCUGUGAAGAUA | 345. | D-010665-02 |
|  |  |  | GAGAGAAACUGCCAUAUAA | 346. | D-010665-01 |
|  |  |  | AGACAACUCUGAUGAAUUA | 347. | D-010665-03 |
|  |  |  | GGACUGAUAUUCACUCAUU | 348. | D-010665-04 |
| LY6G6C | 80740 | NM_025261.1 | GGACAACUGCAACAGCGCA | 349. | D-014622-04 |
|  |  |  | GACAACACAUGCAUACCUU | 350. | D-014622-01 |
|  |  |  | GGUCUCAGCUGACAUUCGC | 351. | D-014622-03 |
|  |  |  | UAAGCUGGGUCUGACAUAU | 352. | D-014622-02 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| MGC33212 | 255758 | NM_152773.3 | UAUAUUCUGCGGCCUGUUU | 353. | D-015945-04 |
|  |  |  | GCAAGUAGUGAUUGGAGAA | 354. | D-015945-02 |
|  |  |  | CAACUAUACUCAUGAUGUU | 355. | D-015945-01 |
|  |  |  | GACAGUUUAUUCUGCGUUG | 356. | D-015945-03 |
| MLKL | 197259 | NM_152649.2 | GAGAUGAAAUACUGCAAGA | 357. | D-005326-04 |
|  |  |  | GAGCAACGOAUGCCUGUUU | 358. | D-005326-02 |
|  |  |  | GGAAGGAGCUCUCGCUGUU | 359. | D-005326-01 |
|  |  |  | AAUAGAAGCUUCACUGAGA | 360. | D-005326-03 |
| MPG | 4350 | NM_002434.2 | GGAUGAACCGGCCCACUCA | 361. | D-005146-01 |
|  |  |  | GAAGCAGCGACCAGCUAGA | 362. | D-005146-02 |
|  |  |  | ACAUCAUUUACGGCAUGUA | 363. | D-005146-03 |
|  |  |  | GGCCCAUACCGCAGCAUCU | 364. | D-005146-04 |
| MPZL1 | 9019 | NM_003953.5 | CAAGAAAGAUGCAUCAAUC | 365. | D-015738-01 |
|  |  |  | AGUCAUAUAUGCACAGUUA | 366. | D-015738-03 |
|  |  |  | GGAAUUAUCCACCAUUUAA | 367. | D-015738-06 |
|  |  |  | UCAUAUAUGCACAGUUAGA | 368. | D-015738-05 |
| MTFR1 | 9650 | NM_014637.3 | GAAGAUUUGCGCUCUCGAA | 369. | D-019432-03 |
|  |  |  | GGUACUAAUUUGUCUCUGA | 370. | D-019432-02 |
|  |  |  | GCUUAUCGGUAUCGAAGUG | 371. | D-019432-04 |
|  |  |  | GAGUUCAGUUUCAGAUUAA | 372. | D-019432-01 |
| MYOCD | 93649 | NM_153604.2 | GAUAAUGGAUGGAUUCUCU | 373. | D-015905-02 |
|  |  |  | GCAAUGGGCUGCAGUUAAG | 374. | D-015905-01 |
|  |  |  | GGUUUACACUCUUCUGAUA | 375. | D-015905-03 |
|  |  |  | GUGCCGACUUGGUUAAUAU | 376. | D-015905-04 |
| NOS3 | 4846 | NM_000603.4 | CGGAACAGCACAAGAGUUA | 377. | D-006490-02 |
|  |  |  | AGGAGAUGGUCAACUAUUU | 378. | D-006490-04 |
|  |  |  | CGAGGAGACUUCCGAAUCU | 379. | D-006490-03 |
|  |  |  | UGAAGCACCUGGAGAAUGA | 380. | D-006490-01 |
| NOSTRIN | 115677 | NM_052946.2 | CCUACAAACUGUCAUCAAU | 381. | D-015170-03 |
|  |  |  | GCAAUAACUUAAACCAGUA | 382. | D-015170-01 |
|  |  |  | CCGCUUAUGUGGAGGAGUU | 383. | D-015170-04 |
|  |  |  | GAAAGACACAGCAGCGUUA | 384. | D-015170-02 |
| NUPL1 | 9818 | NM_014089.3 | GAAUCUUGGUUCAGCAAUU | 385. | D-013864-02 |
|  |  |  | CAGAACACACCCAGAGUUA | 386. | D-013864-03 |
|  |  |  | UGAAAUAGCUUUAAGAACC | 387. | D-013864-01 |
|  |  |  | CAACUAUAACUACAGGAUU | 388. | D-013864-04 |
| PCDHGA1 | 56114 | NM_018912.2 | GAAAUAACGACUCCAGGUA | 389. | D-013277-01 |
|  |  |  | GUAACGUACUCCUUUCACA | 390. | D-013277-04 |
|  |  |  | CAACGUGUCUCUCAGCCUA | 391. | D-013277-02 |
|  |  |  | GCCCAAAUAUUUCGUUUAG | 392. | D-013277-03 |
| PCGF6 | 84108 | NM_032154.3 | GAGGAGGAGCGCCUGAUUA | 393. | D-007084-04 |
|  |  |  | GAAGUUUGUUCGAGUUUCA | 394. | D-007084-03 |
|  |  |  | GGAAAUCCGACGUGCAAUA | 395. | D-007084-01 |
|  |  |  | GAUAUAAUCUGUGGUGAUC | 396. | D-007084-02 |
| PDLIM3 | 27295 | NM_014476.3 | CGGCUAAGCUGGCCCCUAA | 397. | D-020229-03 |
|  |  |  | GCAUAAUAUUCGGCCCAAA | 398. | D-020229-04 |
|  |  |  | GUACUCAGAUGACAAUAUU | 399. | D-020229-01 |
|  |  |  | GGACAGGAUUAAAGCAGCA | 400. | D-020229-02 |
| PIP | 5304 | NM_002652.2 | GGACAACACUCGGAAGAUC | 401. | D-004904-01 |
|  |  |  | AAGAAUGCAUGGUGGUUAA | 402. | D-004904-02 |
|  |  |  | GUAUACUGCCUGCCUAUGU | 403. | D-004904-04 |
|  |  |  | GAACGAGUAGGUAUGUCUU | 404. | D-012050-03 |
| PLCH2 | 9651 | NM_014638.2 | CAAUCGAAAGCGUGUAGAA | 405. | D-027529-04 |
|  |  |  | UCCCAUACCUGACGAACUG | 406. | D-027529-03 |
|  |  |  | CAUCGGGCGUGACUUCAUU | 407. | D-027529-01 |
|  |  |  | AGUCACGGGUGGACAUGUA | 408. | D-027529-02 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| POLM | 27434 | NM_013284.2 | GAACACUCCUCUAGGGUUG | 409. | D-010035-04 |
|  |  |  | CGACACAUGUUGUGAUGGA | 410. | D-010035-01 |
|  |  |  | GGACAUAAGCUGGUUAACA | 411. | D-010035-02 |
|  |  |  | CCAUGAAGCUCUUCACCCA | 412. | D-010035-03 |
| PPAN | 56342 | NM_020230.4 | GCAAAGUGAUGUUCCACAG | 413. | D-017891-01 |
|  |  |  | AGUACUCGCUGGUGCGUGA | 414. | D-017891-04 |
|  |  |  | GGAGUUGGGUGAGGACGAU | 415. | D-017891-03 |
|  |  |  | GUAAGAAGAACUCGCUGAA | 416. | D-017891-02 |
| SAMM50 | 25813 | NM_015380.4 | CGAAGGAGACUACCUAGGU | 417. | D-017871-03 |
|  |  |  | GAACAAGCAACUCAUAUUU | 418. | D-017871-01 |
|  |  |  | UAACUGAAUUGAGGAGAUU | 419. | D-017871-02 |
|  |  |  | CAAAUGGGUUAGACGUUAC | 420. | D-017871-04 |
| SCYL3 | 57147 | NM_020423.5 | GAGCUGAACUGGGAAGAUA | 421. | D-005357-02 |
|  |  |  | GAACAUUGGUGGAAAGUUU | 422. | D-005357-01 |
|  |  |  | UUAAAGAGCUAUACACUGA | 423. | D-005357-03 |
|  |  |  | CAACAGACCUUGCACUCAA | 424. | D-005357-04 |
| SEL1 | 85465 | NM_033505.2 | GAAACUCAAUUCAGUCUAU | 425. | D-027817-02 |
|  |  |  | UGACUGGGUUUGGAUUGUA | 426. | D-027817-03 |
|  |  |  | GAUUAUGGGUUGUGCAUUA | 427. | D-027817-01 |
|  |  |  | AGAGCUACAUCCUAGAGUA | 428. | D-027817-04 |
| SFXN2 | 118980 | NM_178858.4 | GCGCAUGUCUUUCCAGCUU | 429. | D-018547-01 |
|  |  |  | GCGGCUAACUGUGUCAAUA | 430. | D-018547-02 |
|  |  |  | GUAGUUAUUUCUCGGAUCA | 431. | D-018547-03 |
|  |  |  | AUGGAGAACUUGAGCCUUA | 432. | D-018547-04 |
| SLC1A3 | 6507 | NM_004172.4 | GAACUGAACUUCGGACAAA | 433. | D-007427-01 |
|  |  |  | GAAGAAACCAUAUCAACUG | 434. | D-007427-03 |
|  |  |  | GCUGUAGUCUAUUAUAUGA | 435. | D-007427-04 |
|  |  |  | GGUAUUCUCUUCCUGAUUG | 436. | D-007427-02 |
| SLC35A1 | 10559 | NM_006416.4 | CGCUAUAGCUAUUGCUGUA | 437. | D-007537-04 |
|  |  |  | GACAUUAGCUGGCGUCUAC | 438. | D-007537-02 |
|  |  |  | CAACAUGGCUUUCCUAGCU | 439. | D-007537-01 |
|  |  |  | UACCAUAGCUUUAAGAUAC | 440. | D-007537-03 |
| SLC41A3 | 54946 | NM_017836.3 | CAACCUACCUGCACAUGUG | 441. | D-007330-01 |
|  |  |  | CCAAGCCACUGGAGACUGA | 442. | D-007330-04 |
|  |  |  | ACACAAAGAUAGUCGGUAU | 443. | D-007330-03 |
|  |  |  | GCAUGCUUCUGGACUAUUU | 444. | D-007330-02 |
| SRP54 | 6729 | NM_003136.3 | GCAAGAGGAUCGGGUGUAU | 445. | D-005122-04 |
|  |  |  | GAAAUGAACAGGAGUCAAU | 446. | D-005122-03 |
|  |  |  | GAAGAGGUAUUGAAUGCUA | 447. | D-005122-01 |
|  |  |  | GAAGACCUGUUUAAUAUGU | 448. | D-005122-02 |
| STAC3 | 246329 | NM_145064.1 | CUAAGCUGGUCAACGAUAA | 449. | D-015865-02 |
|  |  |  | UCGCAAUGAUCCUGUGUUU | 450. | D-015865-01 |
|  |  |  | GCGGCUACGUCAAGGUCUA | 451. | D-015865-04 |
|  |  |  | AAACCAACAUCCAUGAACA | 452. | D-015865-03 |
| STARD5 | 80765 | NM_181900.2 | CCGAGAAGAUGCUCCAGUA | 453. | D-014629-01 |
|  |  |  | GCGGUUACCUCCCACAGAA | 454. | D-014629-03 |
|  |  |  | GAAGCAAUUCCAUGAGUAA | 455. | D-014629-02 |
|  |  |  | GAGGAGAAGGCAUUGUAUA | 456. | D-014629-04 |
| SULT1C4 | 27233 | NM_006588.2 | GAACAUGGGAAGAGUAUUU | 457. | D-010391-03 |
|  |  |  | ACAACAUGGUGUCCUAUUA | 458. | D-010391-04 |
|  |  |  | GGAGAUAGUGGAAUUAUUA | 459. | D-010391-02 |
|  |  |  | GAACAAAGCGCUUAAGUGU | 460. | D-010391-01 |
| TGS1 | 96764 | NM_024831.6 | GAACAGAACUUCCUUAACA | 461. | D-017151-01 |
|  |  |  | UAAGUGAAGUUAGUAGCAA | 462. | D-017151-04 |
|  |  |  | GCGGGAGGAUUGUAAGAUA | 463. | D-017151-03 |
|  |  |  | GCACGACGCUUCCACAAGU | 464. | D-017151-02 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| TRIM28 | 10155 | NM_005762.2 | AGAAUUAUUCAUGCGUGA | 465. | D-005046-06 |
| | | | GACCAAACCUGUGCUUAUG | 466. | D-005046-03 |
| | | | GAUGAUCCCUACUCAAGUG | 467. | D-005046-04 |
| | | | GCGAUCUGGUUAUGUGCAA | 468. | D-005046-05 |
| UBE2A | 7319 | NM_003336.2 | GCGUGUUUCUGCAAUAGUA | 469. | D-009424-03 |
| | | | GAUGAACCCAAUCCCAAUA | 470. | D-009424-02 |
| | | | CUAUGCAGAUGGUAGUAUA | 471. | D-009424-04 |
| | | | GAUGUGUCUUCCAUUCUAA | 472. | D-009424-01 |
| WDR18 | 57418 | NM_024100.3 | GGGCACAGGAACCAGGUGA | 473. | D-021451-04 |
| | | | GGACCUGCACUGCGGCUUU | 474. | D-021451-03 |
| | | | GCAGAAAGCAUCCACCUGU | 475. | D-021451-01 |
| | | | GCAGUGAGGGCUCCAUCUU | 476. | D-021451-02 |
| ZNF132 | 7691 | NM_003433.3 | GACAGGGACGCACUUAUGA | 477. | D-019560-04 |
| | | | UGAGGAAGCACCAGAAAUU | 478. | D-019560-01 |
| | | | GAAAGUUCACACACAGGUA | 479. | D-019560-03 |
| | | | AGUAAUAGCUCCACCCUCA | 480. | D-019560-02 |
| ZNF154 | 7710 | NM_001085384.1 | AGGCAAAGCUCUAGUCUCA | 481. | D-023833-01 |
| | | | GCAGUACGACCUCAUGAAU | 482. | D-023833-04 |
| | | | GGUCUGCACUCCUUCAACA | 483. | D-023833-03 |
| | | | GGCAGAGCCUUGUUUGUGA | 484. | D-023833-02 |
| ZNF224 | 7767 | NM_013398.1 | GGGAAGAGAUUUACUCAAA | 485. | D-006593-03 |
| | | | GGUAAGAGCUUCUGUGGUA | 486. | D-006593-02 |
| | | | GGAAGGGCUACAAUAGUA | 487. | D-006593-01 |
| | | | GGAAGGGCUACAAUAGUA | 488. | D-006593-01 |
| ZNF432 | 9668 | NM_014650.2 | GAAGAGCCGUAUGAUCGAA | 489. | D-020326-03 |
| | | | GAAUAGCGGACUGAUGUUA | 490. | D-020326-02 |
| | | | GGGAAGAGCAUGCUUAUUA | 491. | D-020326-01 |
| | | | CAAGCGUAAUCUCAUUGUA | 492. | D-020326-04 |
| ZNF473 | 25888 | NM_015428.1 | ACCCGGAUCUUCCACCUUA | 493. | D-023781-03 |
| | | | GAGGACACCUGGUUAGAUA | 494. | D-023781-01 |
| | | | GCAAAUACCUAACUCAGCA | 495. | D-023781-02 |
| | | | GUACUCGGCUCAUUCACCA | 496. | D-023781-04 |
| ADAT1 | 23536 | NM_012091.2 | GGAGACAUCCUCAAUGAUA | 497. | D-009346-01 |
| | | | GAGCAGCCUUUGGAUGUUA | 498. | D-009346-04 |
| | | | CUUCGGAGUUCAAGAAUUA | 499. | D-009346-03 |
| | | | GAAGGAGUUUCCAAAGGUA | 500. | D-009346-02 |
| ALG10 | 84920 | NM_032834.3 | UCAAAGGUUUAUGUGGUAA | 501. | D-027138-04 |
| | | | GGAAUUUCGUUACUUCAUU | 502. | D-027138-01 |
| | | | AUAAAUACUUGCUAGCAGA | 503. | D-027138-03 |
| | | | CGUAUUUGAUGUGUCUUUA | 504. | D-027138-02 |
| ASAH1 | 427 | NM_004315.4 | GAAAAUAGCACAAGUUAUG | 505. | D-005228-04 |
| | | | GGUCAUAACUGAGCAACUA | 506. | D-005228-02 |
| | | | CACCAUAAAUCUUGACUUA | 507. | D-005228-01 |
| | | | UAUAUGAACUCGAUGCUAA | 508. | D-005228-03 |
| B3GALT2 | 8707 | NM_003783.3 | GAUAGCAAGUGGUACAUGC | 509. | D-013692-04 |
| | | | GAACUGGGUUGCAACAUAC | 510. | D-013692-03 |
| | | | AAAUACAGCCACCUAAUUA | 511. | D-013692-01 |
| | | | GUAUUAAGCUAAAUGGCUA | 512. | D-013692-02 |
| GCAT | 23464 | NM_014291.2 | GAACCAUGCCUCCAUCAUC | 513. | D-009547-02 |
| | | | GGCCAUACCUCUUCUCCAA | 514. | D-009547-01 |
| | | | GCUGCUGGCUUCACUAUCU | 515. | D-009547-03 |
| | | | UAACUUCUGUGCCAACAAC | 516. | D-009547-04 |
| HPSE | 10855 | NM_006665.4 | GAUCAAACCUUGCCACCUU | 517. | D-015322-02 |
| | | | GCAAUGAACCUAACAGUUU | 518. | D-015322-01 |
| | | | GGACUGGACUUGAUCUUUG | 519. | D-015322-03 |
| | | | GAACAGCACCUACUCAAGA | 520. | D-015322-04 |

TABLE 1-continued

Decreased Influenza A Infection

| Gene Symbol | Gene ID | Accession Number | siRNA sequence | SEQ ID NO. | Dharmacon Catalog Number |
|---|---|---|---|---|---|
| LFNG | 3955 | NM_002304.2 XM_496845 | GCAACGUGGUCAUCACAAA | 521. | D-025279-01 |
| | | | GAAUACGGCUGAGCGGAUC | 522. | D-025279-04 |
| | | | CAAGAUGGCCGUGGAGUAU | 523. | D-025279-05 |
| | | | GAGCUACGGUAUGUUUGAA | 524. | D-025279-02 |
| MOCS3 | 27304 | NM_014484.3 | CCCACUCGCUACCUGGUUA | 525. | D-006406-02 |
| | | | GAUGAGAUUCUGCGCUAUA | 526. | D-006406-03 |
| | | | GGAGGUACUCGCCUUACAA | 527. | D-006406-01 |
| | | | GAAGAUCCUCCAGUCCUUA | 528. | D-006406-04 |
| NAGA | 4668 | NM_000262.2 | CCGGGUCUGUGAUAUAUGA | 529. | D-011090-03 |
| | | | GGGACAUGGGCUACACAUA | 530. | D-011090-04 |
| | | | GCAGGACCGAUAUGCCUUA | 531. | D-011090-02 |
| | | | GAACUUUGGUCUCAGCUUA | 532. | D-011090-01 |
| NT5C | 30833 | NM_014595.1 | GGACACAGUUCGAGGCCAG | 533. | D-020511-04 |
| | | | GAGCACAUCUUGUUCACCU | 534. | D-020511-02 |
| | | | GAAUUAUCCUGACAAGGGA | 535. | D-020511-01 |
| | | | CAACUGGAGGGAGAUCUUA | 536. | D-020511-03 |
| PCSK5 | 5125 | NM_006200.3 | GGACAAAGAGGGAUUAUGA | 537 | D-005987-01 |
| | | | GUGCAGAGCUGUAGUAUCA | 538. | D-005987-03 |
| | | | GAGGAGACCUGGCCAUCUA | 539. | D-005987-04 |
| | | | GGAACUAGGUCUCAGCUUU | 540. | D-005987-02 |
| PIP4K2B | 8396 | NM_003559.4 | AAAGAAAUACCACCAGUUU | 541. | D-006779-04 |
| | | | GCCAGAAAGUGAAGCUAUU | 542. | D-006779-05 |
| | | | CCUCAAGGGUUCUACGGUU | 543. | D-006779-06 |
| | | | UCAAUGAGCUGAGCAAUGU | 544. | D-006779-02 |
| PTS | 5805 | NM_000317.2 | GAUCAUAAGAAUCUGGAUA | 545. | D-010377-02 |
| | | | GACAGUACAUGGAGAGAUU | 546. | D-010377-01 |
| | | | GCCAUGGGCACAAUUAUAA | 547. | D-010377-05 |
| | | | CUACGGGAAUGGUUAUGAA | 548. | D-010377-03 |
| ST8S1A1 | 6489 | NM_003034.3 | GCAUAAUUCGGCAAAGGUU | 549. | D-011775-04 |
| | | | CAUCUUUGAGGGUUUAUUA | 550. | D-011775-02 |
| | | | GUGAAGAGGUGGCCAUCUA | 551. | D-011775-01 |
| | | | GAAAUGCGCGGUGGUGGGA | 552 | D-011775-03 |
| TPSAB1 | 7177 | NM_003294.3 | CGGGAGACGACGUCCGCAU | 553. | D-006055-03 |
| | | | UGGAGGAGCCGGUGAACGU | 554. | D-006055-02 |
| | | | UGGACUGGAUCCACCACUA | 555. | D-006055-04 |
| | | | CCACAUUUGUGACGCAAAA | 556. | D-006055-01 |
| TSTA3 | 7264 | NM_003313.3 | GAAGUCACCUUUGAUACAA | 557. | D-011412-01 |
| | | | CAAGACGACCUACCCGAUA | 558. | D-011412-02 |
| | | | CGGAUGGGCAGUUUAAGAA | 559. | D-011412-03 |
| | | | CCGCGGAGGCAGUUCAUAU | 560. | D-011412-04 |
| UBE2E1 | 7324 | NM_003341.3 | GAGAGUAAAGUCAGCAUGA | 561. | D-008850-04 |
| | | | GCGAUAACAUCUAUGAAUG | 562. | D-008850-01 |
| | | | GUAUGAGGGUGGUGUAUUC | 563. | D-008850-05 |
| | | | GGUGUAUUCUUUCUCGAUA | 564 | D-008850-02 |

A list of those proteins, deletion of which resulted in increased Influenza A infection, and that were not redundant with the fly screen or Reactome, is given in Table 2.

TABLE 2

Increased Influenza A Infection

| Gene Symbol | Gene ID | Accession Number | siRNA sequence | SEQ ID NO: | Dharmacon (D-) or Ambion Catalog Number |
|---|---|---|---|---|---|
| IFITM3 | 10410 | NM_021034.2 | GCAUUCGCCUACUCCGUGA | 565. | D-014116-04 |
| | | | UCAACACCCUCUUCAUGAA | 566. | D-014116-03 |
| | | | CAAACCUUCUUCUCUCCUG | 567. | D-014116-02 |

TABLE 2-continued

Increased Influenza A Infection

| Gene Symbol | Gene ID Number | Accession | siRNA sequence | SEQ ID NO: | Dharmacon (D-) or Ambion Catalog Number |
|---|---|---|---|---|---|
| | | | UUGAAAGGCUCUUAGUCUA | 568. | D-019900-02 |
| | | | ACGUGUUUCUGGUGCUAAA | 569. | D-014116-13 |
| | | | AUGGAUAGAUCAGGAGGCA | 570. | D-014116-14 |
| | | | UGCUGAUCUUCCAGGCCUA | 571. | D-014116-15 |
| | | | UCGUCAUCCCAGUGCUGAU | 572. | D-014116-16 |
| | | | GCCUAUGGAUAGAUCAGGATT | 573. | Ambion s195033 |
| | | | CCCACGUACUCCAACUUCCTT | 574. | Ambion s195035 |
| | | | UGUCCAAACCUUCUUCUCUTT | 575. | Ambion s237512 |
| PUSL1 | 126789 | NM_153339.1 | GUACGUGGGCACCGACUUU | 576. | D-016667-03 |
| | | | GAGCCAGUCUUUCCUGUAU | 577. | D-016667-01 |
| | | | UGAAGACGAUUCUGGAGAG | 578. | D-016667-04 |
| | | | GAACGCAACCUAUGCUGGA | 579. | D-016667-02 |
| TPST1 | 8460 | NM_003596.3 | GGAGAGAUCUACAGACCAA | 580. | D-008839-02 |
| | | | GGAAUGCCAUCACCGGAUA | 581. | D-008839-01 |
| | | | GAUUUGAUCUGAACAGCUA | 582. | D-008839-04 |
| | | | GGACGCACAUCCUGACAUU | 583. | D-008839-03 |
| WDR33 | 55339 | NM_018383.3 | UAAAGUAAAGUGUCCUGUA | 584. | D-017101-02 |
| | | | GCCCGGAGAUGAACGUUUC | 585. | D-017101-03 |
| | | | GGCCAGGUCAUGAACAUUU | 586. | D-017101-04 |
| | | | GCACAUAAGGAGGCGAUUA | 587. | D-017101-01 |

Example 2

The Genetic Screen Identifies IFITM3 as an Influenza A Virus Restriction Factor In the validation round, the depletion of four genes, interferon-inducible transmembrane protein 3 (IFITM3), PUSL1, TPST1, and WDR33, resulted in increased viral infection, with two or more siRNAs per pool; see Table 3.

TABLE 3

| Gene Symbol | Dharmacon Catalogue Number | 50 nM siRNA concentration Normalized Cell # | SD | Normalized Percent Infected Cells | SD |
|---|---|---|---|---|---|
| IFITM3 | D-014116-04 | 1.18 | 0.24 | 0.90 | 0.02 |
| IFITM3 | D-014116-03 | 1.11 | 0.24 | 1.99 | 0.11 |
| IFITM3 | D-014116-02 | 0.71 | 0.24 | 1.51 | 0.10 |
| IFITM3 | D-014116-01 | 1.18 | 0.05 | 1.91 | 0.05 |
| PUSL1 | D-016667-03 | 1.59 | 0.16 | 1.66 | 0.05 |
| PUSL1 | D-016667-01 | 0.72 | 0.02 | 1.88 | 0.13 |
| PUSL1 | D-016667-04 | 0.57 | 0.34 | 0.60 | 0.03 |
| PUSL1 | D-016667-02 | 1.67 | 0.08 | 0.86 | 0.03 |
| TPST1 | D-008839-02 | 0.85 | 0.12 | 1.73 | 0.13 |
| TPST1 | D-008839-01 | 0.63 | 0.15 | 1.58 | 0.01 |
| TPST1 | D-008839-04 | 0.42 | 0.05 | 0.77 | 0.15 |
| TPST1 | D-008839-03 | 0.58 | 0.05 | 1.74 | 0.03 |
| WDR33 | D-017101-02 | 1.09 | 0.37 | 2.26 | 0.03 |
| WDR33 | D-017101-03 | 0.94 | 0.27 | 1.60 | 0.29 |
| WDR33 | D-017101-04 | 0.74 | 0.11 | 2.03 | 0.08 |
| WDR33 | D-017101-01 | 1.07 | 0.06 | 1.71 | 0.02 |

Depletion of IFITM3 by each of three distinct siRNAs caused increased infection. Five out of six additional unique siRNAs targeting IFITM3 also increased infection in U2OS cells, with the phenotype correlating with the level of IFITM3 depletion (FIG. 3A, 3B). The sequence of the IFITM3 siRNAs were IFITM3-1 (Dharmacon D-014116-13, Target sequence ACGUGUUUCUGGUGCUAAA (SEQ ID NO:569)); IFITM3-2 (Dharmacon D-014116-14, Target sequence AUGGAUAGAUCAGGAGGCA (SEQ ID NO:570)); IFITM3-3 (Dharmacon D-014116-15, Target sequence UGCUGAUCUUCCAGGCCUA (SEQ ID NO:571)); IFITM3-4 (Dharmacon D-014116-16, Target sequence UCGUCAUCCCAGUGCUGAU (SEQ ID NO:572)); IFITM3-5 (Ambion s195033, Sense GCCUAUG-GAUAGAUCAGGATT (SEQ ID NO:573)); and IFITM3-6 (Ambion s195035, Sense CCCACGUACUCCAACUUC-CTT (SEQ ID NO:574)).

Importantly, increased influenza A virus infection was also observed when IFITM3 levels were depleted in human primary lung fibroblasts, a more physiologically relevant host cell (WI-38 cells). In addition, cervical adenocarcinoma cells (HeLa cells, grown in DMEM (Invitrogen Cat#11965) with 10% FBS (Invitrogen)) showed elevated infection when treated with the IFITM3 siRNAs, and newly budded virus from these IFITM3-depleted cells was also increased>5 fold in tittering assays. Lowering IFITM3 levels similarly increased infection by the influenza A H1N1 viral strain, WS/33, which expresses an NS1 protein that has been suggested to be more virulent than PR8's NS1 (FIG. 10 (Haye et al., 2009; Kochs et al., 2007)).

Cells stably expressing a C-terminal HA-tagged protein, IFITM3-HA$^{6R}$, lacking the 3'-untranslated region targeted by siRNA IFITM3-6, were created. The coding sequence for IFITM3 was obtained from the Vidal Lab Human Orfeome in pDONR-223, after being fully sequence confirmed as correct with the designated Refseq sequence (NM_021034.2), it was recombined into a Gateway-compatible destination vector with a C-terminal HA epitope tag and a Puromycin selectable gene, using LR-clonase (Invitrogen) to produce pMSCV-IFITM36R. An empty version of the expression vector (pMSCV-puro) was used as control. IFITM3-transducing pseudovirus was generated as previously described (Huang et al., 2006, J. Biol. Chem. 281 (2006), pp. 3198-3203; Huang et al., 2008 J. Virol. 82 (2008), pp. 4834-4843), except that myc-IFITM3 was ligated into the pQCXIX vector (Clontech), and used to generate transducing virus, MVL-myc-IFITM3, and myc-IFITM3-expressing virus was incubated with A549 cells. Cells were washed one hour later, and two days later, challenged with MLV-GFP pseudovirus bearing the indicated entry protein. Entry measured by GFP-expression was measured two days later by flow cytometry.

Overexpression of IFITM3-HA$^{6R}$ rescued resistance to the virus in the face of siRNA-mediated depletion of the endogenous protein, further confirming it is an "on target" effect (FIG. 3C, D). Thus, IFITM3 is required for basal levels of cellular resistance to influenza A virus infection.

The mRNAs for IFITM3, and the closely related and linked genes, IFITM1 and 2 (50%, and 92% amino acid identity, respectively, FIG. 4I, 6F), have been reported to be inducible by both IFN type I (α) and II [γ (Friedman et al., Cell 38, 745-755, 1984; Lewin et al., Eur J Biochem 199, 417-423, 1991)]. This was confirmed for the IFITM3 protein by Western blot and IF (WI-38 cells, cultured in DMEM (Invitrogen Cat#10569), containing 1×MEM non-essential amino acids (Invitrogen Cat#11140, 10 mM stock/100×) and 15% FBS, FIG. 3E). Interferon-gamma (Invitrogen Cat #PHC4031) was used at 100 ng/ml, Interferon-alpha A (Invitrogen Cat#PHC4014) was used at 100 ng/ml. Cells were incubated with cytokines for 24 hours prior to viral infection. In unstimulated cells, the majority of IFITM3 resides in the ER (based on co-localization with sialic acid and N-acetylglucosamine-conjugated proteins stained by the plant lectin, wheat germ agglutinin, WGA, S3A). IFN exposure, in contrast, triggers the distribution of IFITM3 in a vesicular pattern throughout the cell. The IFN-induction and localization of IFITM3 was confirmed using additional cell lines (U2OS and HeLa), anti-sera, and specificity controls (siRNA-targeting and peptide-blocking).

Example 3

IFITM3 is Required for IFN's Anti-viral Effect

In view of these dynamic changes, IFITM3's functional role in the IFN response was examined. About 2200 cells were plated per well in clear bottom 96 well plates (Corning 3603), one day prior to transfections. Cells were transfected with siRNAs at 50 nM final concentration and Oligofectamine at 0.4% in DMEM containing 15% FBS. For WI-38 primary fibroblast cells, 6000 cells were plated per well one day prior to transfection in Corning 3603 plates. The following day, transfections were done using Lipofectamine 2000 and 100 nM final concentration siRNA. siRNA-mediated target gene depletion occurred over three days, then cells were challenged with one of the following: influenza A virus (H1N1) A/PR/8/34, influenza A (H1N1) virus A/WS/33, or MLV-GPF pseudoviruses (either H1 or VSV-G envelope proteins).

Viral propagation and titration were evaluated as follows. Influenza A (H1N1) virus A/PR/8/34 (ATCC VR-1469) and influenza A (H1N1) virus A/WS/33 (ATCC VR-1520) were propagated and viral infectivity was titrated as previously described (Huang et al., 2008).

Either IFN-alpha or -gamma strongly decreased basal levels of influenza A virus infection in both U2OS or HeLa cells (FIG. 3E, 3H, 3I). The depletion of IFITM3 profoundly decreased the antiviral actions of either IFN-gamma or -alpha (FIG. 3F, FIG. 3H, 3I). This effect was most pronounced with increasing amounts of virus, consistent with the saturation of a restriction factor. IFN's protective effects were largely restored with the stable expression of IFITM3-HA$^{6R}$, which is resistant to the 3'UTR-targeting siRNA, IFITM3-6 (FIG. 3G). Because this is a population of cells stably expressing IFITM3-HA$^{6R}$ to different levels, it would not be expected to see complete restoration of resistance. These results indicate that IFITM3 is required both for basal levels of resistance, as well as for the heightened defenses elicited by IFN γ and α in vitro.

Example 4

IFITM1 and IFITM2 Inhibit Early Replication of Influenza A Virus

Figure 4A:
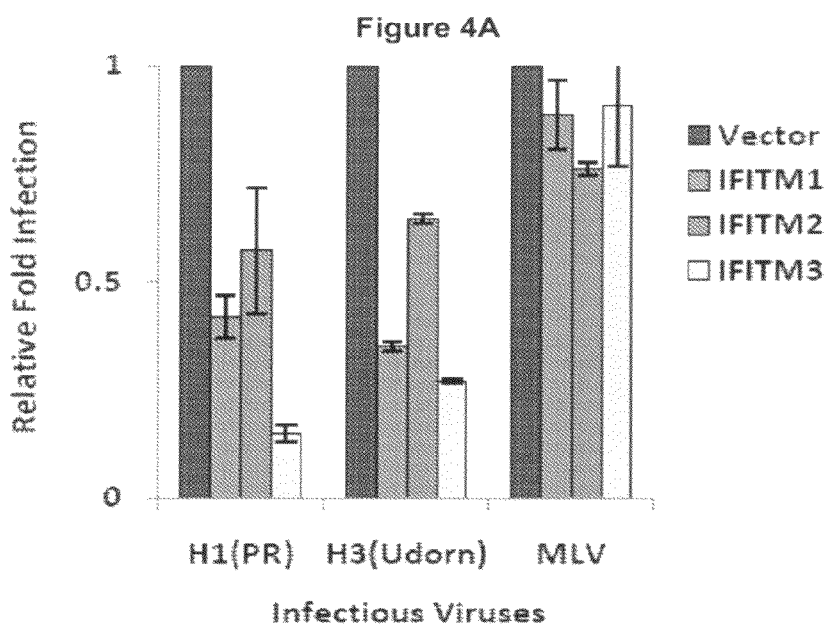
FIG. 4A is a bar graph showing changes in relative fold infection in A549 cells transduced with retroviruses containing epitope tagged cDNAs for the indicated IFITM proteins, or empty viral vector alone (vector). Two days later the transduced cells were infected with one of the following viruses: influenza A H1N1 PR8 [H1(PR)], influenza A H3N2 A/Udorn/72 [H3(Udorn)], or Moloney Leukemia virus (MLV). Twelve hours after infection the cells were checked for HA surface expression by FACS. Values represent the mean±SD, N=3.
Figure 4B:
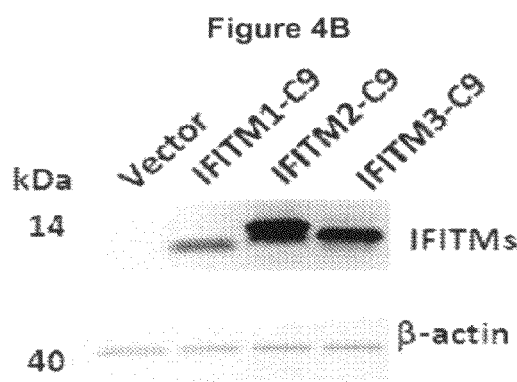
FIG. 4B is an image showing the results of Western blot analysis of A549 cells transduced with retroviruses containing the indicated IFITM proteins, or the empty vector control virus. After 48 hours the levels of the IFITM protein were checked using anti-C9 antibody, which detects the epitope tag. β-actin levels show relative protein loading.
Figure 4G:
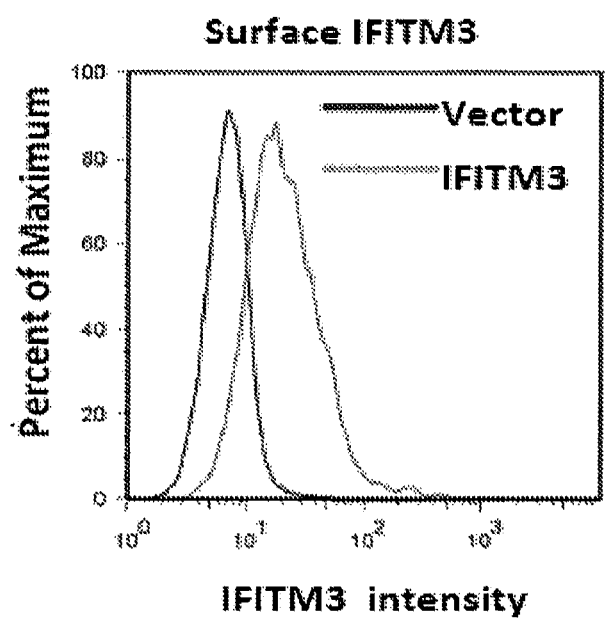
FIG. 4G is a line graph illustrating cell surface expression of N-terminally epitope tagged IFITM3, measured by flow cytometry using the anti-Myc antibody 9E10, is shown for vector and Myc-IFITM3-transduced (IFITM3) A549 cells analyzed in (A and E). Cells were assayed without permeabilization.
Figure 4I:
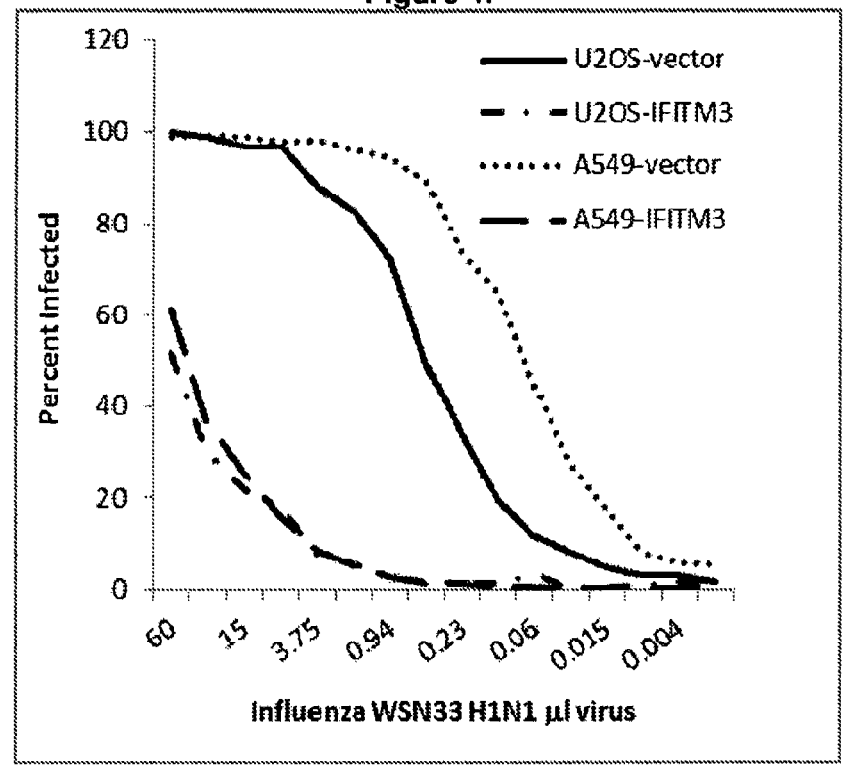
FIG. 4I is a line graph showing the results of experiments wherein A549 or U2OS cells stably over-expressing either IFITM3 or the vector alone (also shown in 4C, D), were infected with influenza A virus H1N1 WSN/33 at the indicated two-fold dilutions of viral supernatant (384 well plates with 64 ul total volume per well). 24 hours. later, the cells were fixed and stained for HA expression by IF. Values represent the mean±SD, N=3.

The effects of over-expression of IFITM3, or its paralogs, IFITM1 and 2, on viral infection were evaluated. A549 lung epithelial carcinoma cells (grown in DMEM (Invitrogen Cat#11965) with 10% FBS (Invitrogen)) were transduced with viruses expressing the IFITM1, 2 or 3 proteins (FIG. 4A). Two days later, the transduced cells expressing the IFITM proteins demonstrated increased resistance to infection with influenza A viruses PR8 (H1(PR)), or H3N2 A/Udorn/72 (H3 (Udorn), FIG. 4A, B). This restriction was not universal, because IFITM proteins did not inhibit Moloney Leukemia virus (MLV, amphotropic envelope). Profound restriction was also seen when IFITM3 was stably over-expressed in both A549 and U2OS cells (FIG. 4C, 4J). To begin to address where in the viral lifecycle the IFITM-induced block was occurring, we used viral pseudoparticles. The pseudoparticles universally contain an MLV genome encoding the enhanced green fluorescent protein (EGFP) cDNA, however, each strain is exclusively coated with the envelope proteins from one of the following viruses: influenza A virus (strains H1, H3, H5, H7), vesicular stomatitis virus G-protein (VSV-G), Machupo virus (MACH), or MLV (FIG. 4D). Overexpression of any of the three IFITM proteins blocked infection by all four of the influenza A enveloped pseudoviruses, with less restriction seen against VSV-G protein, and no decrement observed on viral entry mediated by the MLV (γ-retrovirus) or MACH (arena virus) envelope proteins.

Figure 8A:
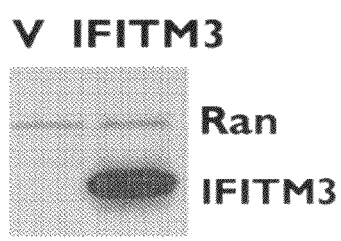
FIG. 8A is a Western blot of MDCK cells stably expressing either the vector control or IFITM3 transgene.
Figure 8B:
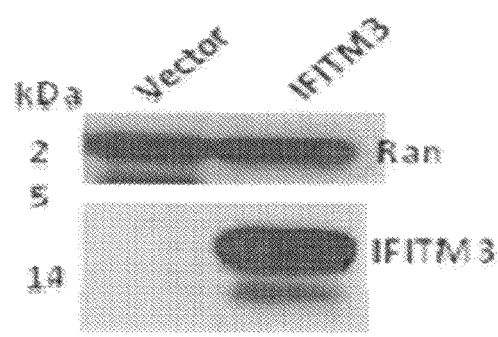
FIG. 8B is an image of a Western blot showing the results of an experiment wherein primary chicken fibroblasts (ChEFs) stably expressing IFITM3 or vector alone were checked for IFITM3 expression.

IFITM3 also potently inhibited additional contemporary virulent strains of influenza A viruses. MDKC or A549 cells stably expressing the IFITM3 protein, or the vector only control (V), were incubated with the indicated viruses. 12 hours after infection, the cells were fixed, and stained for either HA protein expression (H3N2 A/Aichi/68 and H1N1 A/Brisbane/07), or NP(H3N2 A/716/Uruguay/07). Host cell nuclei were stained blue. The mean percent infection is provided +/1 SD, n=3. The over-expression of IFITM3 in a canine cell line used for propagating influenza A viruses (Madin-Darby canine kidney (MDCK) cells), strongly inhibited the cytopathic effect of sequential rounds of viral infection; FIG. 8A depicts a Western blot demonstrating the expression of the exogenous IFITM3 transgene in the MDCK cells. Similarly, profound restriction was seen when IFITM3 was stably over-expressed in primary Chicken fibroblast cells (ChEFs), see FIG. 8B.

These results demonstrate the IFITM3 expression is sufficient to induce a strong block to virulent influenza A virus infection, even in the absence of additional interferon-mediated anti-viral actions. Indeed, the Aichi strain contributed to the Hong Kong flu pandemic of 1968, and both the Brisbane and Uruguay viral strains are current pathogenic isolates and are as such contained in the 2009/2010 influenza A and B vaccine.

To complement these gain-of-function results, we depleted IFITM3 with siRNAs in U2OS cells, than infected them with pseudoparticles, expressing either influenza A virus receptor (H1(PR)) or VSV-G (FIG. 4E). Consistent with the over-expression data, depleting IFITM3 led to increased infection of the influenza A H1 pseudoviruses, with VSV-G entry elevated to a lesser extent, with the more potent of the two siRNAs, IFITM3-6. Because the lifecycles of the pseudoviruses only differ in the means of entry mediated by their respective viral envelopes, these data are consistent with the IFITM proteins blocking influenza A virus infection early in the viral lifecycle, somewhere between and including viral-host receptor binding and entry of the vRNP into the cytosol.

Influenza A virus infection begins with the viral envelope proteins interacting with sialylated glycoproteins on the host cell's surface (Lamb and Krug, 2001). There was no reduction, and even a slight increase, in the levels of either α-2,6-sialic acid (SA) or α-2,3-SA when IFITM proteins were over-expressed, pointing away from a reduction in SA concentration underlying the anti-viral actions of the IFITM proteins (FIG. 4F).

Interestingly, when expression of IFITM3 protein in the transduced cells was assessed by flow cytometry, the N-terminal epitope tag was bound by the anti-Myc antibody without membrane permeabilization, revealing that the N-terminus is extracellular. In addition, the C-terminal HA epitope tag of IFITM3$^{6R}$ was stained in IF studies using non-permeabilized cells, demonstrating that IFITM3's C-terminus, similar to its N-terminus, is extracellular. In addition, the anti-HA antibody used to detect PR8 flu infection does not recognize the HA nonapeptide tag on IFITM3-HA$^{6R}$ (FIG. 3C, G, uninfected controls (no virus)).

Example 5

IFITM3 Inhibits the Early Replication of West Nile virus and Dengue Virus

To better determine the specificity of IFITM-mediated restriction, a panel of viral-like particles (VLPs) and pseudotyped viruses, each uniquely expressing a unique envelope protein, was tested. MLV-GFP pseudoviruses have been previously described (Huang et al., 2006; Huang et al., 2008). The level of infection of transduced A549 cells was assessed 2 days later by measuring GFP expression by flow cytometry. The level of infection of siRNA-transfected U2OS cells after two days of infection was determined by calculating the percent GPF positive cells by IF using the IXM scanning miscoscope, after fixation with 4% PFA and staining of nuclei with Hoechst 33342.

Figure 5A:
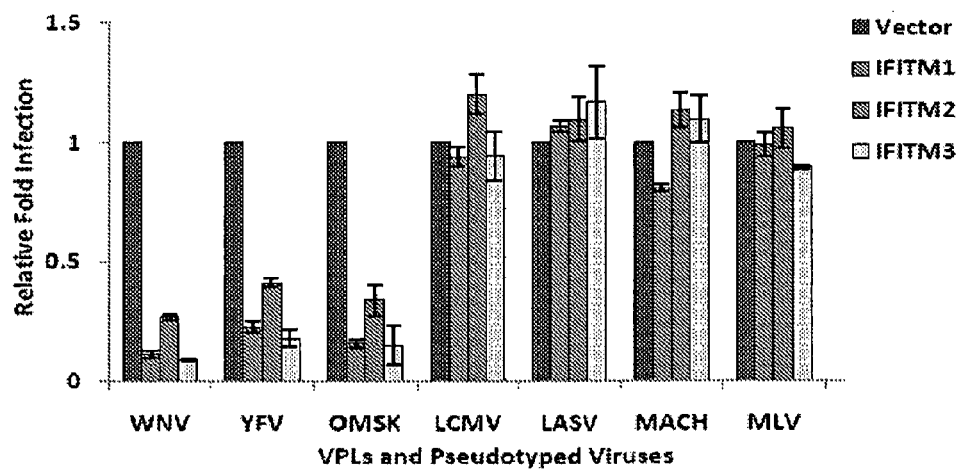
FIG. 5A is a bar graph showing changes in relative fold infection in A549 cells transduced with retroviruses expressing the indicated IFITM proteins, or the empty viral vector. Two days later, the cells were incubated with flaviviral viral like particles (VLPs), expressing EGFP, and coated in envelope proteins from WNV, YFV or Omsk virus (OMSK), or with EGFP—expressing MLV viruses pseudotyped with the indicated viral envelope proteins. Viral infection is expressed as mean EGFP fluorescence relative to vector control cells, as measured by flow cytometry 48 hours post-infection. Values represent the mean±SD, N=3.

The VLPs expressed the envelope proteins of one of three flaviviruses, WNV, yellow fever virus (YFV) or the Siberian hemorrhagic tick-borne Omsk virus (OMSK). These VLPs can undergo a single round of infection, and are produced by transiently expressing the respective envelope proteins together with the WNV structural genes, in cells stably expressing sub-genomic WNV replicons containing EGFP (Yoshii and Holbrook, 2009). As observed with influenza A pseudoparticles, all three VLPs were blocked by over-expression of any of the three IFITM proteins, demonstrating that these restriction factors impede first round infection (FIG. 5A). In contrast, pseudoparticles expressing the envelope proteins of three arenaviruses, lymphocytic choriomeningitis virus (LCMV), Lassa virus (LASV) and MACH, or MLV retrovirus, were not affected by IFITM protein levels.

The effects of IFITM protein levels were tested on two pathogenic flaviviruses, WNV and DNV. West Nile (strain 2741) and dengue serotype 2 (New Guinea C strain) viruses were used to infect the IFITM3 silenced HeLa cells at an MOI of 0.1 for 24 or 30 hours respectively, as reported previously (Krishnan et al, Nature. 2008 Sep. 11; 455(7210):242-5). Infected cells were fixed in 4% PFA and immuno-stained with antibodies detecting viral E-proteins (Chemicon), and imaged by fluorescence microscopy (Zeiss). IFITM3 over-expressing or vector control-A549 or -U2OS cells were infected with WNV at an MOI of one. Viral propagation and titration of WNV and DNV were performed as follows: WNV (strain 2741) and DNV serotype 2 (New Guinea C strain) viruses were grown on Vero cells (ATCC#CRL-1586) or C6/30 (ATCC#CRL-1660) cells, respectively.

Figure 5B:
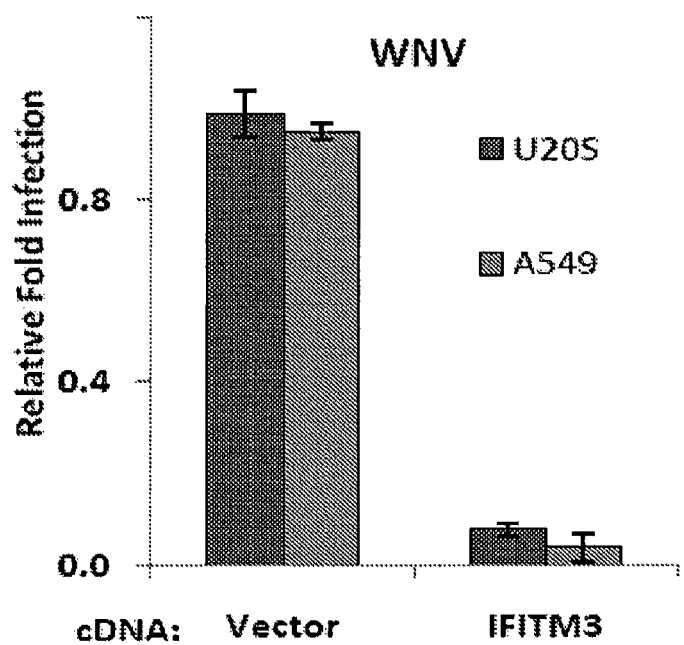
FIG. 5B a bar graph showing changes in relative fold infection in A549 or U2OS cells stably expressing either IFITM3 protein or the vector alone (also shown in 4C, D), and infected with infectious WNV (strain 2741). 24 hours. later, the cells were fixed and stained for viral E protein expression by IF. Values represent the mean±SD, N=3
Figure 5C:
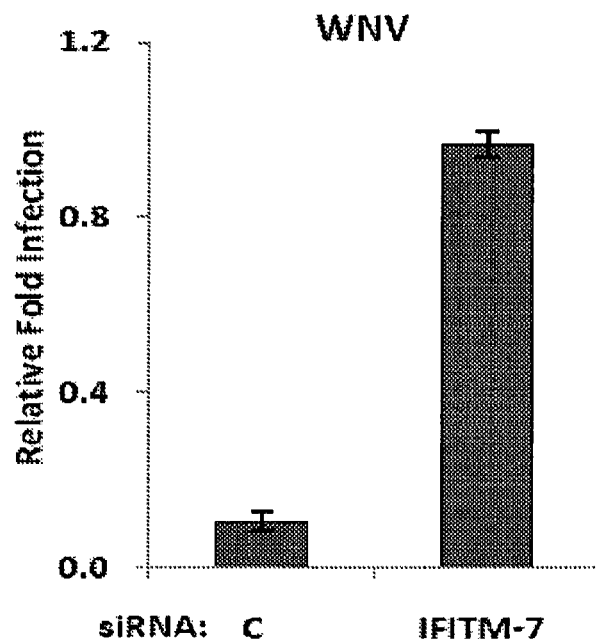
FIG. 5C is a bar graph showing changes in relative fold infection in HeLa cells transfected with the indicated siRNAs for 72 hours, then infected with WNV. 24 hours later, the cells were fixed and stained for viral E protein. Values represent the mean±SD, N=3. C, Non-targeting siRNA negative control. Magnification, 4×.
Figure 5D:
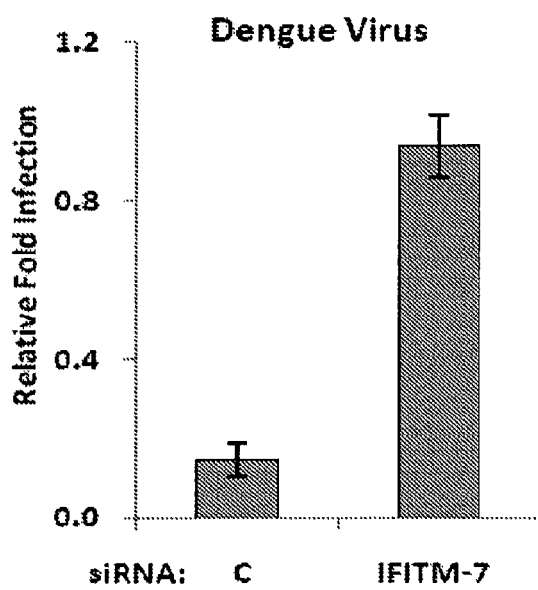
FIG. 5D is a bar graph showing changes in relative fold infection in HeLa cells transfected with the indicated siRNAs for 72 hours, then infected with dengue virus (New Guinea C strain). 30 hours. post-infection, the cells were fixed and stained for viral E protein expression by IF. Values represent the mean±SD, N=3. C, Non-targeting siRNA negative control. Magnification, 4×.

As observed with influenza A virus infection, the replication of the 2741 strain of WNV was dramatically decreased in either A549 or U2OS cells stably over-expressing IFITM3 (FIG. 5B). Furthermore, siRNA-depletion of IFITM3 protein also led to an increase in replication of both WNV (FIG. 5C) and DNV serotype 2 (New Guinea C strain, FIG. 5D).

This indicates that IFITM proteins restrict the replication of two additional human pathogens, DNV and WNV, and may likely help to limit YFV and OMSK infection, based on the VLP data.

Example 6

Figure 6A:
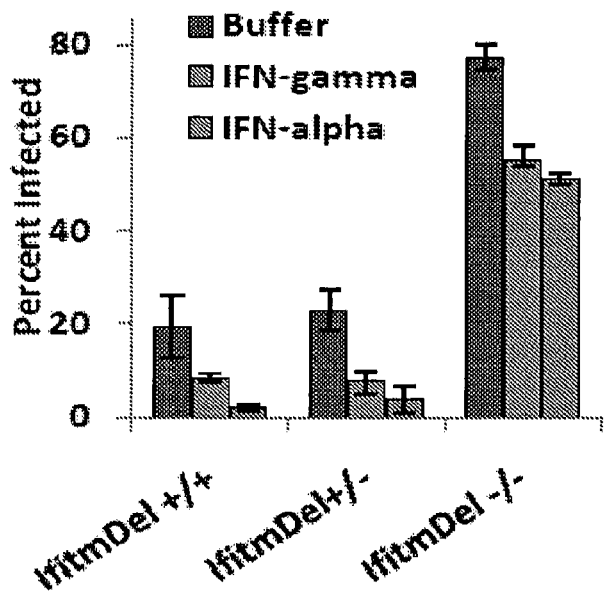
FIG. 6A is a bar graph showing changes in percent of cells infected in MEFs derived from the indicated IfitmDel mice, were left untreated (buffer), or treated with interferon-α or γ. After 24 hours, the cells were incubated with influenza A virus H1N1 (PR8). Twelve hours after infection, the cells were checked for HA surface expression by IF. Values represent the mean±SD, N=3.
Figure 6B:
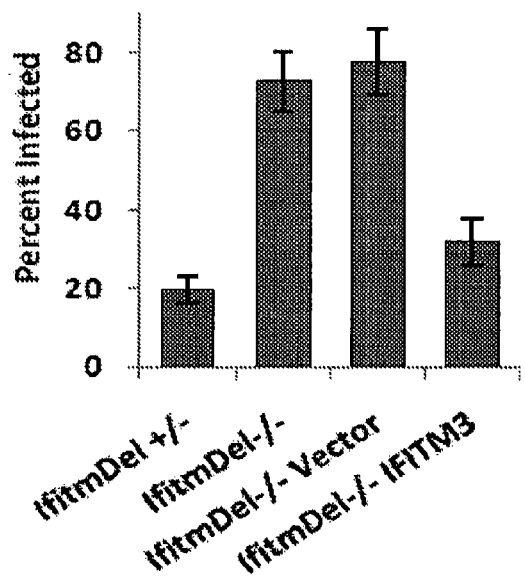
FIG. 6B is a bar graph showing changes in percent of cells infected in IfitmDel+/+MEFs, or IfitmDel−/−MEFs stably expressing IFITM3 or the empty vector, that were challenged with PR8 virus. 12 hours later, the cells were fixed and imaged for HA expression. Values represent the mean±SD, N=3.
Figure 6C:
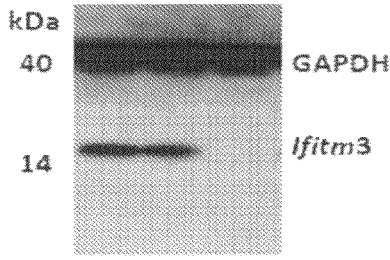
FIG. 6C is an image of a Western blot showing the results of an experiment wherein MEFs from 6A) were assessed by Western blot for the presence of Ifitm3 protein. GAPDH levels are provided to show protein loading.
Figure 6D:
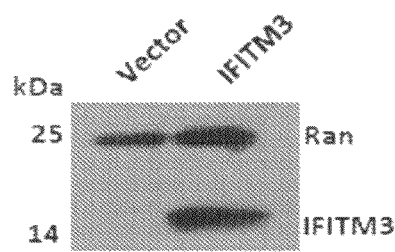
FIG. 6D is an image of a Western blot showing the results of an experiment wherein the indicated MEFS were assessed for IFITM3' expression by Western blot. Ran demonstrates protein loading.
Figure 6E:
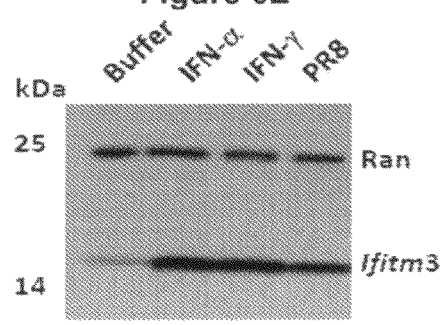
FIG. 6E is an image of a Western blot showing the results of an experiment wherein MEFs were left untreated (buffer), or incubated with either IFN-γ, IFN-, or PR8 virus. After 24 hours the levels of Ifitm3 were checked by Western blot. Ran levels show relative protein loading.
Figure 6F:
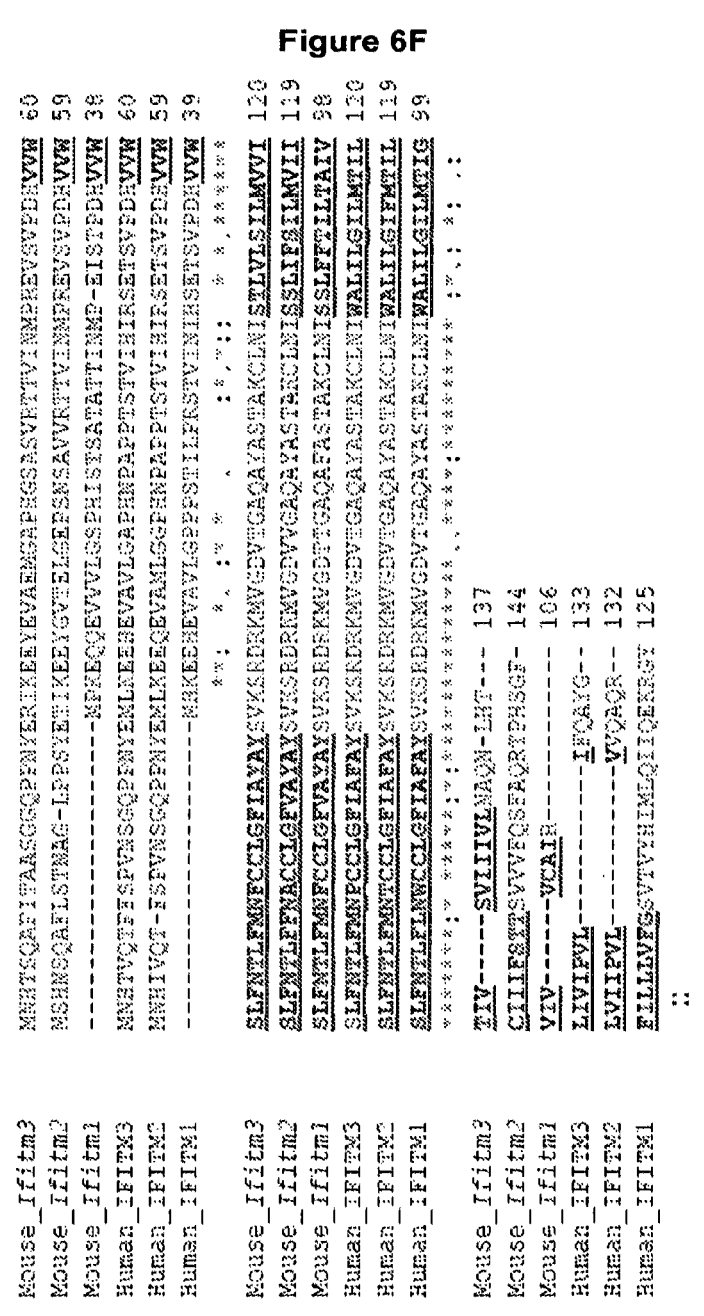
Figure 7:
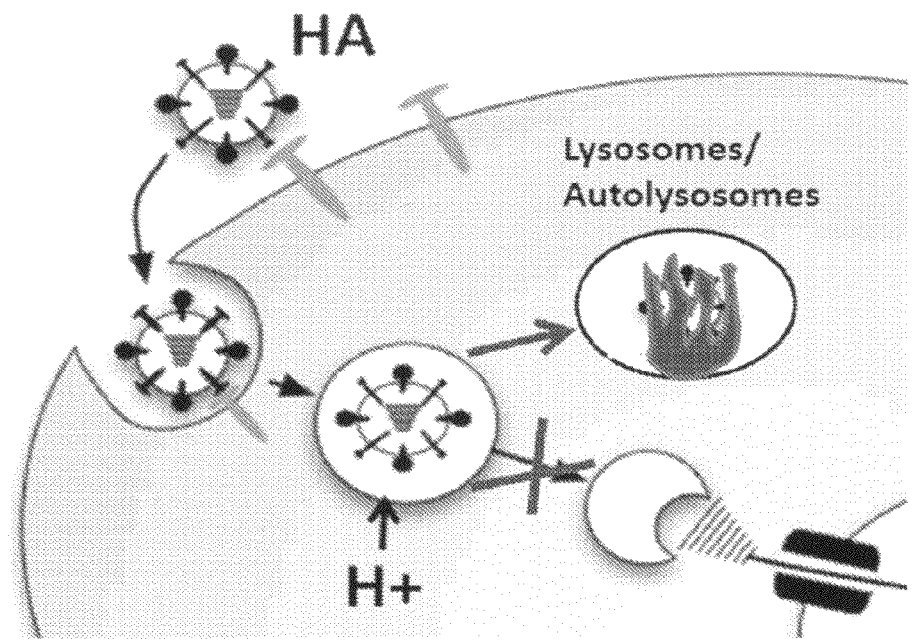
FIG. 7 is a schematic model of IFITM-mediated inhibition of viral infection. IFITM1, 2 and 3 are represented by a dual-transmembrane protein. IFITM proteins interfere with influenza A virus infection by preventing viral fusion, thereby stopping vRNPs from gaining access to the host cell's nucleus. Instead invading pathogens are directed to the cell's lysosomes where they are held and destroyed. IFN also inhibited viral fusion and vRNP nuclear translocation, and IFITM3 was required for this activity. These data thus extend our previous work demonstrating the requirement of IFITM3 for 50-80% of IFN's virustatic effects in vitro, and also reveal that an early IFN-mediated block to infection is occurring at viral fusion [11]. IFITM3 thus represents a previously unappreciated type of anti-viral effector that permits viral entry into the endosomal compartment, but denies egress into the cytosol, thereby neutralizing the cumulative infectious threat to the organism.

Deletion of the Murine Ifitm Locus Leads to Increased Influenza A Virus Infection In Vitro Human and murine IFITM proteins display a high degree of inter-species homology (FIG. 6F, IFITM or Ifitm, denote the respective human and mouse genes throughout). Therefore, the role of the IFITM proteins in influenza A infection was evaluated in murine embryonic fibroblasts (MEFs) from a previously reported mouse strain, IfitmDel, which has had all five of its Ifitm genes (Ifitm1, 2, 3, 5 and 6) removed by gene targeting (Lange et al., 2008). The IfitmDel mice have been shown to develop normally and to have normal phenotypic characteristics within the parameters previously tested (Lange et al., 2008). Comparison of +/+, +/− and −/− MEFs revealed a marked increase in PR8 infection in the −/− cells (FIG. 6A). Susceptibility of the −/− cells to infection was more pronounced when the MEFs were incubated with either murine IFN α or γ, prior to infection (FIG. 6A). Western analysis performed as described above confirmed the loss of Ifitm3 expression in the −/− MEFs, when compared to +/− or +/+ cells (FIG. 6C). To determine the function of IFITM3 in this genetic background, the human protein was stably expressed in the IfitmDel-/-cells; the transgene rescued the majority of resistance to influenza A H1N1 virus infection (FIG. 6B, D). Ifitm3 levels increased after either IFN treatment, or viral infection (FIG. 6E). A vesicular staining pattern was observed in the +/+ cells, but not in the −/− cells, using anti-sera raised against Ifitm3; this pattern was identical to that seen for IFITM3 in the human cell lines tested (FIG. 3H, 3I)

These data indicate that the IFITM protein family, and particularly IFITM3, accounts for a significant proportion, but not all, of the anti-influenza actions of Type I and II IFNs in mice, because the majority of this function can be restored by the stable expression of IFITM3.

Example 7

IFITM3 Blocks Replication of Infectious Avian H5N1 Influenza A Virus

As described above, IFITM3 protected cells from infection by viral pseudoparticles expressing the HA envelope protein of an H5N1 avian influenza A virus from Thailand. Because highly pathogenic avian influenza viruses are a continuing public health concern, we determined whether IFITM3 could inhibit replication of wild type H5N1 influenza A virus A/Vietnam/1203/04 (VN/04), isolated from a fatal human infection. IFITM3 lowered the in vitro replication of VN/04 virus at 12 h post-infection (p.i.) in a stably transduced A549 lung carcinoma cell line, as determined by reduced expression of viral nucleoprotein, NP.

A549 cells obtained from ATCC were grown in complete media (DMEM (Invitrogen Cat#11965) with 10% FBS (Invitrogen)). A viral infectivity assay employing increasing multiplicities of infection (moi) revealed that expression of IFITM3 decreased avian influenza virus infectivity by >130-fold, based on the moi needed to infect 50% of the cells in IFITM3-transduced versus vector control cell monolayers (FIG. 11A).

Example 8

IFITM3 Inhibits Influenza a Viral Infection after Viral-Host Binding but Before Viral Transcription Inhibition of viral pseudoparticles by the IFITM proteins demonstrated that the restriction occurred during the envelope-dependent phase of the infection cycle. We therefore undertook experiments to more fully determine where IFITM3 prevents infection. First, we tested the most proximal phase of infection, viral binding, by incubating influenza A virus A/WSN/33 H1N1 (WSN/33) with A549 cells either stably overexpressing IFITM3 (A549-IFITM3) or an empty vector control cell line (A549-Vector, FIG. 11B), as follows.

A549 cells transduced with IFITM3 or empty vector were cultured in 6-well plate (1.0×10$^6$ cells/well) and lifted using cell dissociation buffer (Gibco), washed in cold PBS twice. Cells and virus were pre-chilled on ice for 30 minutes and mixed at an MOI of 5.0 and incubated at 4° C. for 1 hour in a shaker. The viral supernatant and cells were incubated on ice to permit viral binding but prevent endocytosis, which is a temperature-dependent step. After incubation, Cells were washed five times with ice cold PBS and fixed using 4% formaldehyde. The cells were then probed with anti-HA (monoclonal hybridoma, HA-29) antibody for 1 hour at room temperature, followed by anti-mouse alexaflour-488 conjugated antibody for 1 hour with PBS washes in between. The cells were analyzed by flow cytometry on a BD FACS Caliber machine.

Figure 11C:
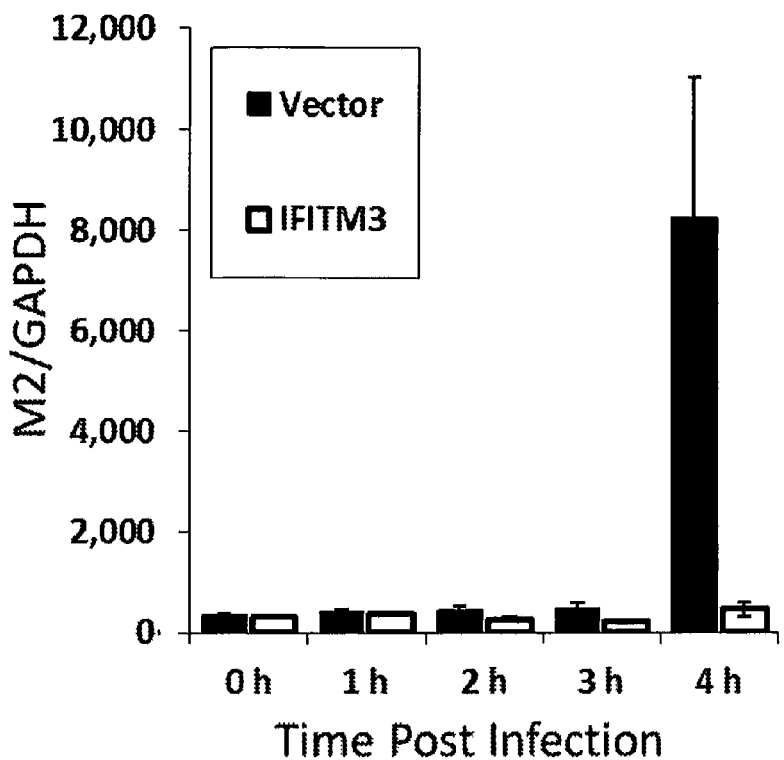
FIG. 11C is a bar graph showing the results of experiments wherein A549 cell lines were infected with H1N1 WSN/33. At the indicated time points cDNA was prepared and viral M2 mRNA expression levels were measured by qPCR. Values were normalized to host cell GAPDH mRNA levels. Values represent the mean+/−SD of three independent experiments.

No appreciable difference in surface bound HA was observed between the vector and IFITM3 cells. There was also no difference in surface-bound virus over a series of ten-fold dilutions of viral supernatant. To confirm IFITM3's impact on a post-entry phase of the viral lifecycle, viral mRNA production, we infected the A549-IFITM3 and vector cells with WSN/33 virus (moi=5) and then harvested total RNA at the indicated times. Quantitative PCR (qPCR) was performed using host cell (GAPDH) and viral gene (M2)-specific probe sets (FIG. 11C).

A549 cells transduced with vector or IFITM3 was incubated with WSN33 virus in triplicate at 37° C. for 1 h (hour) and washed extensively with DMEM media. Cells were collected at 0 h, 1 h, 2 h, 3 h and 4 h post infection, trypsinized, and total RNA was isolated using an RNeasy Kit (Qiagen). cDNA was synthesized from 50 nM RNA with sensiscript (Qiagen) kit using random and oligo dT primers. Forward primer, InfA forward (GACCRATCCTGTCACCTCTGAC; SEQ ID NO:594), reverse primer, InfA reverse (AGGGCATTYTGGACAAAKCGTCTA; SEQ ID NO:595), GAPDH forward primer (GGAGCCAAACGGGTCATCATCTC; SEQ ID NO:596) and GAPDH reverse primer (GAGGGGCCATCCACAGTCTTCT; SEQ ID NO:597) were purchased from IDT DNA. The qPCR was carried out using a Light cycler 480 Real Time PCR System (Roche) and Sybergreen PCR reaction mix (Roche).

An increase of viral M2 mRNA synthesis occurred at 3 to 4 hr p.i. in the control cells, but was absent in the IFITM3 expressing cells. Therefore, IFITM3 inhibits influenza A viral infection after viral-host binding but before viral mRNA transcription.

Example 9

IFN Interferes with vRNP Nuclear Entry, and IFITM3 is Required for this Antiviral Response We next used confocal imaging to track the nuclear translocation of vRNPs over time (Khor, R., L. J. McElroy, and G. R. Whittaker, Traffic, 2003. 4(12): p. 857-68; Konig, R., et al., Nature, 2010. 463(7282): p. 813-7). At the start of infection, the majority of the viral NP within infected cells is complexed to viral genomic RNA as vRNPs. Therefore immunostaining for NP permitted us to follow vRNP distribution intracellularly (Konig, R., et al., Nature, 2010. 463(7282): p. 813-7; Khor, R., L. J. McElroy, and G. R. Whittaker, Traffic, 2003. 4(12): p. 857-68; Lamb, R. A. and R. M. Krug, *Orthomyxoviridae: The viruses and their replication.* 4th ed. Fields Virology, ed. D. Knipe and P. Howley. 2001, Philadelphia: Lippincott Williams and Wilkins). Normal diploid human fibroblasts (WI-38) were stably transduced with an empty vector (Vector), a vector expressing an IFITM3 cDNA (IFITM3), or vectors expressing short hairpin RNAs (shRNA) targeting IFITM3 (shIFITM3-3) or a scrambled non-targeting control (shScramble). Cells were first incubated on ice with the influenza A virus A/Puerto Rico/8/34 H1N1 (PR8, moi~1000). Next, the viral supernatant was removed and warm media was added (0 min). At the indicated times, cells were washed twice with D-PBS (Sigma) and incubated for 30 seconds with room temperature 0.25% trypsin (Invitrogen). The cells were then washed with complete media twice and fixed with 4% formalin (PFA, Sigma) in D-PBS, then stained for NP and DNA and imaged on a confocal microscope. Image analysis software was used to create an outline of each cell's nucleus (pale lines).

Based on NP staining, vRNPs arrive in the nuclei by 60 to 90 min p.i. in the vector control, shIFITM3-3 (shIFITM3), and in the shScramble cells, with the NP signal increasing through to 240 min. In contrast, decreased nuclear and increased cytosolic NP staining was observed in IFITM3 expressing cells, consistent with a block after endocytosis but prior to vRNP nuclear translocation. Since as described above IFITM3 is required for the anti-viral actions of IFN, a companion experiment was performed with IFN-α. IFN-α pre-treatment also decreased NP nuclear staining in the WI-38-Vector cells however this block was not as complete nor was it associated with similar levels of cytosolic NP staining as those seen with high levels of IFITM3. Consistent with the gain-of-function data, the depletion of IFITM3 resulted in a decrease in IFN's ability to block vRNP trafficking to the nucleus. Similar results were observed with MDCK and A549 cell lines expressing high levels of IFITM3.

While NP immunostaining provides a useful read-out for subcellular vRNP distribution, to directly track the movement of the vRNA contained in the incoming vRNPs, MDCK cells stably expressing an empty vector (MDCK-vector) or IFITM3 (MDCK-IFITM3, FIG. 12) were used in time-course infection experiments as above. At the indicated times, cells were processed and stained for the negative stranded NP vRNA of PR8 using a specific RNA probe set (green).

Lysotracker red (LTRed), a lysotropic acidophilic dye (pH<5.5), was also added along with the warm media at time zero.

Figure 12:
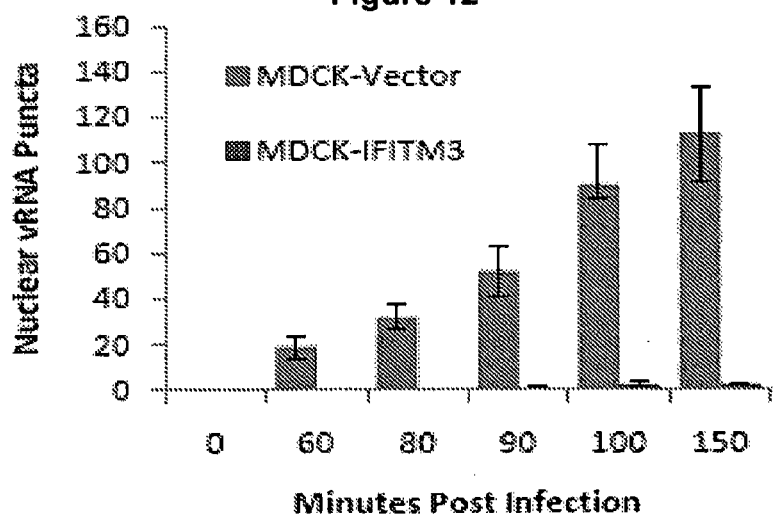
FIG. 12 is a bar graph showing the results of experiments wherein IFITM3 prevented the nuclear translocation of viral genomes to cell nuclei in vitro. MDCK cells stably overexpressing the empty vector control (MDCK-Vector) or IFITM3 (MDCK-IFITM3) were incubated with H1N1 PR8 on ice. Warm media was added at time zero. Cells were then fixed at the indicated time points post infection and hybridized with RNA probes against the viral NP genome (NP vRNA PR8) and stained for DNA, then imaged by confocal microscopy. Quantitation of nuclear viral RNA puncta was done using Imaris image analysis software by determining the number of viral RNA puncta per nucleus of the MDCK-Vector and IFITM3 cells at the indicated time points. Values represent the mean+/−the SD of three independent experiments.

Similar to the α-NP time-courses, the nuclear translocation of vRNA was observed by 90 min p.i. in the control cells, and this nuclear signal was strongly decreased with IFITM3 overexpression based on the average number of vRNA puncta present per nucleus, as determined by image analysis software (FIG. 12). Consistent with the IF results, the vRNAs accumulated in the cytosol of the IFITM3 cells, and co-localized with acidic structures based on their staining with LTRed. Similar levels of retained cytosolic vRNPs were observed in experiments without LTRed (data not shown). In contrast to the persistence of the NP antigen signal, the loss of the vRNA signal in the LTRed+ inclusions of the MDCK-IFITM3 cells was consistently observed between 150 and 240 min pi. In contrast, the vRNAs in the control cells increased in number and moved to the cytosol, consistent with the nuclear export of newly synthesized viral genomes occurring in the course of a normal replication cycle (Lamb, R. A. and R. M. Krug, *Orthomyxoviridae: The viruses and their replication*. 4th ed. Fields Virology, ed. D. Knipe and P. Howley. 2001, Philadelphia: Lippincott Williams and Wilkins). Similar results were obtained using mouse embryonic fibroblasts (MEFs) that are null for all five mouse Ifitm proteins (MEF-IfitmDel–/–) as compared to matched litter mate controls (MEF-WT) when both were exposed to IFN-γ prior to incubation with viral supernatant. In addition, the majority of the vRNP signal in the IFN-γ-treated WT cells localized to LTRed+ cytosolic inclusions. This increase in acidic inclusions occurred after IFN-γ treatment in the WT-MEFs, but not in the MEF-IfitmDel–/– cells. In addition, the acidic compartment was increased in all IFITM3 overexpressing cell lines based on LTRed staining (WI-38, MDCK and A549).

Example 10

Influenza A Virus Infection is Inhibited Prior to Membrane Fusion by Either IFN Stimulation or IFITM3 Overexpression To further characterize IFITM3's point of action, an established viral fusion assay was used (Tobiume, M., et al., J Virol, 2003. 77(19): p. 10645-50; Tscherne, D. M., B. Manicassamy, and A. Garcia-Sastre, J Virol Methods, 2010. 163(2): p. 336-43). Lentiviral pseudoparticles (pps) containing the β-lactamase protein fused to the HIV-1 accessory protein Vpr (BLAM-Vpr) and expressing either HA (H1N1, WSN/33), or VSV-g envelope proteins, were produced by plasmid transfection of HEK 293T cells with an HIV-1 genome plasmid derived from pBR43IeG-nef+ (NIH AIDS Research and Reference Reagent Program (Division of AIDS, NIAID, NIH, Cat#11349, from Dr. Frank Kirchhoff) modified with a deletion which abolishes expression of Env without disrupting the Rev-responsive element, pCAGGS-HA WSN/33, pCAGGS-NA WSN/33 and pMM310, which encodes a hybrid protein consisting of β-lactamase fused to the HIV accessory protein, Vpr (NIH AIDS Research and Reference Reagent Program, Division of AIDS, NIAID, NIH (Cat#11444) from Dr. Michael Miller). pCG-VSV-g together with pBR43IeG-nef+ and MM310 were transfected to produce VSV-g pseudotyped lentiviral particles. Cultures for pseudoparticle fusion assays, including stably transduced MDCK cells and WI-38 fibroblasts, were plated in 24-well dishes at 90,000 cells per well. At the time of assay, 0.5 mL of virus stock was added to cells and incubated for 2 h at 37° C. IN experiments using bafilomycin A1 (Sigma), the inhibitor was added at 37° C. for 1 h prior to incubation with virus. After infection, viral media was then aspirated and replaced with complete media containing the β-lactamase fluorogenic substrate, CCF2-AM (Invitrogen) along with 1.7 µg/mL probenecid. Cells were incubated in the dark for 1 h, followed by dissociation from the dish using Enzyme Free PBS-based Dissociation Buffer (Gibco), and fixation in 2% formalin (Sigma). Flow cytometry was conducted on a Becton Dickinson LSRII using 405 nm excitation from the violet laser, and measuring 450 nm emission in the Pacific Blue channel and 520 nm emission in the Pacific Orange channel. Data was analyzed using FACSDiva.

Figure 13A:
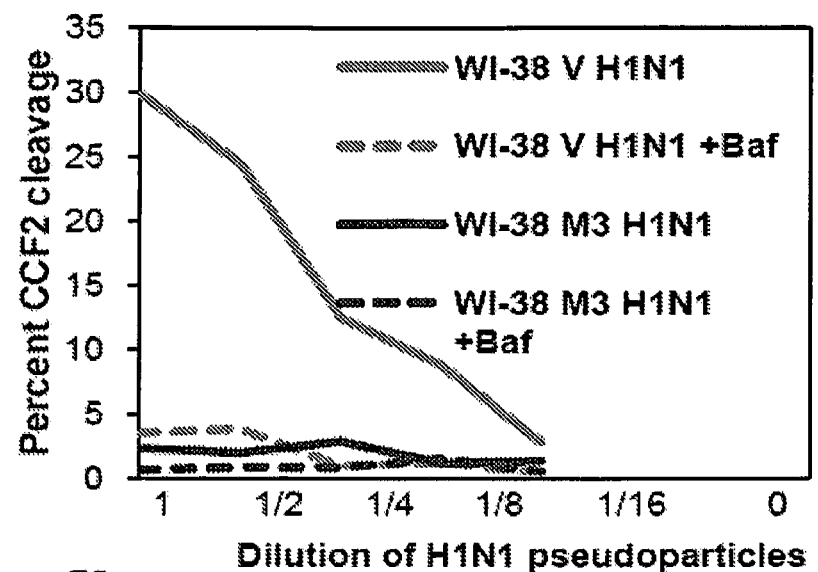
FIG. 13A is a line graph showing that IFITM3 inhibits fusion of HA pseudoparticles in primary fibroblasts. WI-38 fibroblasts stably transduced with IFITM3 (WI-38 M3) or the empty vector (WI-38 V) were exposed for 2 h to serial dilutions of HA pseudoparticles (H1N1) containing BLAM-Vpr, with or without bafilomycin A1 (Baf). These results are representative of four independent experiments.
Figure 13B:
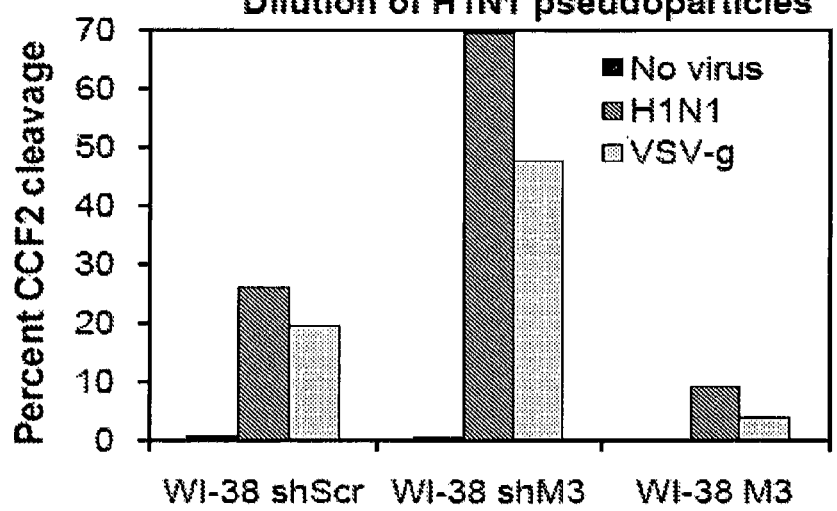
FIG. 13B is a bar graph showing that fusion of HA pseudoparticles increases after IFITM3 knockdown. WI-38 primary fibroblasts stably transduced with a short hairpin RNA against IFITM3 (WI-38 shM3), a shRNA control with a scrambled sequence (WI-38 shScr), or the IFITM3 cDNA (WI-38 M3) were exposed to HA pseudoparticles (H1N1) containing BLAM-Vpr. These results are representative of two independent experiments.

Upon viral fusion, BLAM-Vpr enters the cytosol and can cleave CCF2, producing a wave length shift from green to blue in emitted light when analyzed by flow cytometry (see, e.g., Tobiume, M., et al., J Virol, 2003. 77(19): p. 10645-50). In MDCK-IFITM3 cells a decrease in both HA- and VSV-g-directed fusion was observed, which was comparable to the block produced by poisoning of the host vacuolar ATPase (vATPase) with the macrolide bafilomycin A 1 (Baf), thereby preventing the low-pH activation of HA required for membrane fusion. A strong block to fusion in WI-38-IFITM3 overexpressing cells, similar to that of the bafilomycin control and uninfected controls, was seen at a range of serial dilutions of virus, as well as an increase in fusion with IFITM3 depletion by shRNA (shIFITM3, FIG. 13A, 13B). IFN treatment also inhibited fusion of the H1N1-pps, albeit to a lesser extent than IFITM3 overexpression, and this effect was decreased when IFITM3 was stably depleted in HeLa cells. Thus, either IFN treatment or IFITM3 overexpression decreased infectivity by interfering with the viral lifecycle after endocytosis but prior to membrane fusion.

Example 11

IFITM3 is Present in Endosomes and Lysosomes and these Compartments are Expanded with IFITM3 Overexpression or IFN Treatment After endocytosis, influenza A virus traffics into late endosomes where viral-host membrane fusion takes place. To investigate the intracellular location of IFITM3, we undertook IF studies using the A549-Vector and IFITM3 cells, together with antibodies that recognize either IFITM3 (IFITM3 primary antibody rabbit polyclonal (Abgent AP1153), the endosomal/lysosomal small GTPase protein Rab7 (Rab7 primary antibody—mouse monoclonal (Abcam 50533)), or the lysosomal protein LAMP 1 (Lawe, D. C., et al., J Biol Chem, 2002. 277(10): p. 8611-7).

Cells were fixed in 4% PFA in D-PBS, and then incubated sequentially in 0.25% Tween 20 (Sigma), then 1% BSA with 0.3M glycine (Sigma), both in D-PBS. Primary and secondary antibodies are listed below. Slides were mounted in Vectashield with DAPI counterstain (Vector Labs). Slides were imaged using a Zeiss LSM 510, laser scanning inverted confocal microscope equipped with the following objectives: 40× Zeiss C-APOCHROMAT UV-Vis-IR water, 1.2NA, 63× Zeiss Plan-APOCHROMAT DIC oil, 1.4NA, and 100× Zeiss Plan-APOCHROMAT DIC oil, 1.46NA. Image analysis was performed using ZEN software (Zeiss). Laser intensity and detector sensitivity settings remained constant for all image acquisitions. Nuclear outlines were generated using Metamorph software suite (Molecular Devices) using the Kirsch/Prewitt filter to define boundaries and then subtracting out the original binary images leaving only the new outline.

Figure 14:
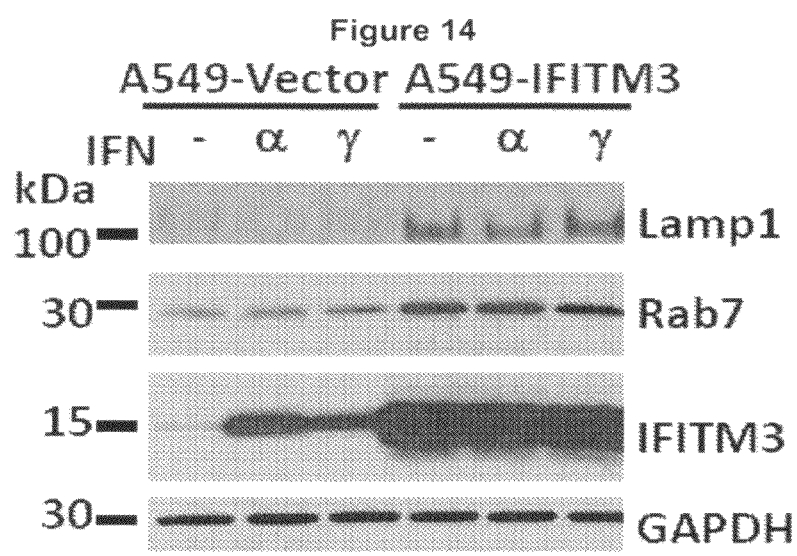
FIG. 14 shows the results of Western blotting of lysates from A549-IFITM3 or A549-Vector cells treated or untreated with IFN-α or γ for 24 h and probed with the indicated antibodies. GAPDH levels are provided to demonstrate relative protein loading. These images are representative of three independent experiments.

Although the baseline levels of IFITM3 in the A549-Vector cells were low, there was partial co-localization with either Rab7 or LAMP1. Interestingly, either IFITM3 overexpression or IFN exposure increased the staining intensity of Rab7 and LAMP1. Similar results were also seen with IFITM3 overexpression in MDCK cells. However, in all cases colocalization was not nearly complete because cells contained areas that uniquely labeled for each of the proteins. Western blots were performed as follows. Whole-cell extracts were prepared by cell lysis, equivalent protein content boiled in SDS sample buffer, resolved by SDS/PAGE, transferred to Immobilon-P membrane (Millipore), and probed with the indicated antibodies. Purified Rabbit polyclonal to IFITM3 was from Abgent (Cat #AP1153a) Human IFITM1 mouse monoclonal antibody was from Proteintech Group, Inc (Cat#60074-1); Anti-fragilis (Ifitm3) rabbit polyclonal antibody was from Abcam (Cat #ab15592), mouse monoclonal anti-GAPDH was from BD Biosciences (Cat#610340). Rab7 primary antibody—mouse monoclonal (Abcam 50533), The LAMP 1 [H4A3] and CD63 [$H_5C6$] antibodies were developed by August, J. T./Hildreth, J. E. K was obtained from the Developmental Studies Hybridoma Bank developed under the auspices of the NICHD and maintained by The University of Iowa, Department of Biology, Iowa City, Iowa. The results indicated that IFITM3 over-expression led to modest increases in both LAMP1 and Rab7 proteins in the A549-IFITM3 cells (FIG. 14). However, these blots also showed that while IFN treatment of the A549-Vector cells increased IFITM3 protein levels as expected, the amount of Rab7 and LAMP1 remained unchanged. Although our anti-human LAMP1 antibody did not recognize endogenous canine LAMP1 by western blotting, we demonstrated that Rab7 levels were only minimally increased in the MDCK-IFITM3 cells when compared with the MDCK-Vector cells. These results indicate that IFITM3 partially resides in a portion of the late endosomal and lysosomal compartments. Furthermore, IFITM3 overexpression or IFN treatment expand these compartments through a mechanism that cannot be fully explained by increased Rab7 or LAMP1 protein levels.

Example 12

IFITM3 Overexpression Leads to the Expansion of the Autophagic Compartment, Amphisomes and Autolysosomes Our infection assays showed that incoming influenza A viruses were halted in the expanded acidic compartments of the IFITM3 cell lines and the IFN-γ-treated WT MEFs.

Therefore these inclusions were characterized further.

For these live cell imaging experiments, the cells were incubated at 37° C. and 5% CO2 for 60 min with either Lysotracker Red DND-99 or acridine orange (ImmunoChemistry Technologies). Hoechst 33342 (DNA stain, Invitrogen) was incubated (1:10,000) with the cells for the final 15 min. The Cathepsin L fluorogenic substrate assay was performed as per the manufacturer's instructions (Cathepsin L-Magic Red, ImmunoChemistry Technologies). Cells were visualized live by confocal microscopy.

An increase in acidic structures were seen in MDCK and A549 cells expressing IFITM3 as compared to control cell lines, using either the vital acidophilic stain, acridine orange (AO), LTRed, or a Cathepsin-L substrate that fluoresces only after its proteolysis, when compared to the corresponding vector control cells. Cathepsins are a family of lysosomal zymogens active in acidic environments (pH 5.5) which are required for the entry of several pathogenic viruses (Schomberg, K., et al., J Virol, 2006. 80(8): p. 4174-8; Huang, I. C., et al., J Biol Chem, 2006. 281(6): p. 3198-203). The MDCK-IFITM3 cells were observed to have the majority of the acidic structures present at their periphery, with a relatively open perinuclear space. Flow cytometric analysis also demonstrated an increase in the LTRed signal in both the MDCK and A549 IFITM3 cell lines when compared to controls.

Ultrastructural examination using electron microscopy (EM) was also performed. Cells were fixed overnight in 2% Glutaraldehyde (EM grade, Electron Microscopy Sciences (EMS)) in 0.1 M Cacodylate buffer pH 7.4 (EMS), then scraped from the plate bottom and washed several times with 0.1 M Cacodylate buffer. Cell pellets were osmicated in 1% osmium tetroxide/1.5% potassium ferrocyanide (final solution) for 3 hours, followed by several washes of dH2O. 1% uranyl acetate in maleate buffer was then added for one hour then washed several times with maleate buffer (pH 5.2). This was followed by a graded cold ethanol series up to 100% which is changed 3× over one hour. Propylene oxide then followed, again 3 changes over one hour. Samples were then placed in ½ and ½ propylene oxide with 812 Resin (Marivac) mixture including catalyst overnight and embedded in pure plastic the next day, then places into a 60 C oven for two days. Blocks/samples: 95 nm sections were cut with a Leica ultracut microtome, picked up on 100 m formvar coated copper grids, stained with 0.2% lead citrate, and viewed and imaged under the JEOL 1200 Electron Microscope.

The results revealed that the MDCK-IFITM3 cells contained multiple large membranous cytoplasmic inclusions that were morphologically variable and ranged in size from 250 to 800 nm in diameter. No similar electron dense structures were seen in the control cells. One population of IFITM3-associated structures were packed tightly with intraluminal vesicles (ILVs, individual vesicles at 20-60 nM in diameter), but contained varying amounts of partially degraded organelles, and therefore are likely amphisomes, which are formed when autophagosomes fuse with multivesicular bodies (MVBs) or late endosomes containing ILVs. A second type of inclusion morphologically resembled autolysosomes, which form upon lysosome and autophagosome fusion, based on the combined presence of partially degraded organelles and multi-lamellar membranous debris (as described in Eskelinen, E. L., Autophagy, 2005. 1(1): p. 1-10). Similar structures were found in EM images of A549-IFITM3 and WI-38-IFITM3 cells, but not in the corresponding vector control cells. The MDCK-IFITM3 cells also had larger structures (2000-4000 nM at their longest axis) containing what are most likely glycogen granules (as described in Rikihisa, Y., Anat Rec, 1984. 208(3): p. 319-27). The IFITM3 expressing cells also displayed MVB-like organelles containing translucent ILVs, which distended the cytoplasmic membrane or were attached to the cell by stalks of cytosol. These last structures were rare, but none-the-less unique to the IFITM3 expressing cells. In one instance all three types of structures were seen across three adjacent cells.

Consistent with these inclusions representing a heterogenous population of autolysosomes and amphisomes, confocal imaging of IFITM3 expressing cells partially colocalized the autophagosome marker, LC3, together with the MVB protein CD63 or with the acidophilic stain LTRed+. Furthermore, MDCK-IFITM3 cells stably transduced with an LC3 protein fused to both a red fluorescent protein (mCherry) and an enhanced green fluorescence protein (EGFP) showed a predominately red signal, which occurs when the mCherry-EGFP-LC3B protein resides inside the acidic interior of an autolysosome (Pankiv, S., et al., J Biol Chem, 2007. 282(33): p. 24131-45). These results indicate that while high levels of constitutively expressed IFITM3 inhibit viral infection, they also alter cellular homeostasis leading to the expansion of the autophagic compartment (amphisomes and autolysosomes).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated modified human cell wherein the modification is i) an insertion of an exogenous nucleotide sequence into the endogenous IFITM3 gene, wherein the insertion disrupts expression of the endogenous IFITM3 gene, or ii) an introduced siRNA sequence that effectively reduces expression of IFITM3, wherein the disruption or reduction of expression of IFITM3 leads to increased infectivity of the modified cell compared to a wild-type human cell of the same type that is not modified and wherein the modified cell is infected with an orthomyxovirus or a flavivirus.

2. The cell of claim 1, wherein the virus is an orthomyxovirus.

3. The cell of claim 1, wherein the IFITM3 protein encoded by said IFITM3 gene comprises the amino acid sequence as set forth in SEQ ID NO:598.

4. A method of producing an orthomyxovirus or a flavivirus, the method comprising: obtaining an isolated modified human cell of claim 1, culturing the cell under conditions sufficient for the orthomyxovirus or flavivirus to be produced, and isolating the orthomyxovirus or flavivirus produced by the cell.

5. The method of claim 4, wherein the cell is cultured in media, and the virus is isolated from the cell or from the media.

6. The cell of claim 1, wherein the virus is a flavivirus.

* * * * *

```
                         SEQUENCE LISTING

<160> NUMBER OF SEQ ID NOS: 633

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gaucagaacc uucacagaa                                                      19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaacagagag uguaagaua                                                      19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ugaaauaucu gagcacugu                                                      19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gacggaggau uacagaaua                                                      19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
acucagaucu gguguaaua                                                      19

<210> SEQ ID NO 6
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 6
gaguugaucc ucagcaauu                                                      19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaauaugcu acacuaugu                                                      19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gaucagacca uccgagugu                                                      19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cgacacagcu auguuagaa                                                      19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uauaaggucu gucaugcua                                                      19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcuguuaccg gccauauaa                                                      19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic

```
          oligonucleotide

<400> SEQUENCE: 12
ccucaugacu ucgcaaaua                                               19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gaagggagca ucauuguua                                               19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uaugggcagu ugugaaaua                                               19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggacacaccc auuauguua                                               19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
caacagcauu guaaagaua                                               19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccaaagaaca gaucaagug                                               19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 18
ggcuguggau gaaauugua                                                    19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaaccuuccc uguauacug                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
caacaagacc caucggacu                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ggaacaggcu ucacaccaa                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaaggaucu aacgggauu                                                    19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
caaagaaggu ccuaguuau                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 24
ggauaucaau uuagacuca                                                  19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcaaagaucc aguuguuaa                                                  19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcacugagcu ggacaauca                                                  19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ggaauaaagu gaagucuag                                                  19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gggaugaugc ccaaugaua                                                  19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cagcagaucc aauccauuc                                                  19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
```
gacugaggcu gaugugaau                                                19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gaaugugccc uacguguuu                                                19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ugaagaaggu gaacaguuu                                                19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ggaagcaggc caaccguau                                                19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gaagcagagc gucguauau                                                19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gcucuuagcu gaucucgaa                                                19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cgggauaagu acucaaaga                                                    19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaagaagcu aacuaaugc                                                    19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcagauggau ugcaguaua                                                    19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugaagcaucu caucuauua                                                    19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gauaagggcu ggcguguca                                                    19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gcuacaaacc cgacguuaa                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gaaccgaucg ugaauaggg                                                    19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gcaagagcau gaacgcgaa                                                19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgaauaccu cacgccuga                                                19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guggaguacu caagacaug                                                19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ggagccaaau uuacaggua                                                19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cgaaagagca guucagaua                                                19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ggaaggagau uguuaacuc                                                19

```
<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaccuccuc ccaaagaua                                                19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cauauugauu acaggauga                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaugagaccu ccuaugggu                                                19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccaaagaacu ccaaacaag                                                19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cgauuaaagu acugcauga                                                19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
auacauccgu ggcagcaaa                                                19
```

```
<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gaacaccggu gagguauau                                                19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gaagaacgca cccauguua                                                19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cagccgaggu gcacaacau                                                19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ucaugcaccu caccgagaa                                                19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ccgcagagac agaggaagu                                                19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ggaaaugacg ggacaaguu                                                19

<210> SEQ ID NO 61
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
acgaggaacu gcccacuua                                                     19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ggaaagggcu ucaaaguag                                                     19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gaauuucgga agccuauga                                                     19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gcaagcauau guugagaaa                                                     19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caagaagggu agucuccuc                                                     19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gaagaugucc cauacacag                                                     19

<210> SEQ ID NO 67
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcagcucucu accuacuua                                                   19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gaacgacucu uugguacca                                                   19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caucauggca auugucauu                                                   19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gcaugguucc ugacggaga                                                   19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaacuacca ugcaggcua                                                   19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gugaggcugu ggccaucua                                                   19

<210> SEQ ID NO 73
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 73
uggacaaccu cuuggcuuu                                                    19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74 gcaugggau cccguggca                                                     19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugaccauccu ccagacaua                                                    19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
caugaaaacu accgcauaa                                                    19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77 gagggguggcu uugaguaua                                                   19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gaagaggcug uggguaaua                                                    19

<210> SEQ ID NO 79
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 79
gcaaacacgc cguccuuau                                                    19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggaggcccgu guauuuaau                                                    19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ccaaguacgc caagaugga                                                    19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gaagcaggcu cuaggaggg                                                    19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
agggcauccg agacaagua                                                    19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
agaagaagga ggagcgcga                                                    19

<210> SEQ ID NO 85
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 85
caauuaugau gcaugguuu                                                    19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gaaaggguac gagugauuu                                                    19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gaucaaguau gcccgcuuu                                                    19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
cgagcgugcu uuagaugua                                                    19

<210> SEQ ID NO 89
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
augaugaguu ugggaauua                                                    19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gaccaagauc ugugcuaua                                                    19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
        oligonucleotide

<400> SEQUENCE: 91
uggaugaggu caauggauu                                                19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uggcggaucu gauggauaa                                                19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gcaccagcau uagauguca                                                19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcccacccu caaccaaua                                                19

<210> SEQ ID NO 95
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ccaaugauau caaggagga                                                19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gccuggagcu gcagugguu                                                19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 97
cgggacagcc caugauuaa                                                    19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ccuacggaca gcagaguua                                                    19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gauuauaccc aacaagcaa                                                    19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gaucaauccu ccaugagua                                                    19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ggaccuacgu cuucaacau                                                    19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gcaggacaau cccucgucg                                                    19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 103
cggaggacuu ggccaucua                                            19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
cgucuuacau gcucgugaa                                            19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
cguauuggcu ggucacuaa                                            19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gaacagaaag gcggagaua                                            19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
ggaaagaccu accagaaca                                            19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
guagaacucu cguaugcua                                            19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
```
gaaacaaaca aguugcgaa                                                    19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cuuauuagcu gggcgauuu                                                    19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
ggaauguggc cucaaauua                                                    19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
aaauuaaccu ggucucauu                                                    19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aagugaaggu aaagcguua                                                    19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gcucaggucg caccaaaua                                                    19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uaugaggcau ggaaaguuc                                                    19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ggagaaagca gaaauugaa                                                    19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
gcugguaccu cuucaacag                                                    19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ggggaaagcu ggccaccuu                                                    19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gcucugggca gcuuucaaa                                                    19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gcccacagcu caccaccua                                                    19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
guaugcagcu cuucgguuu                                                    19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
ccgccaagaa guauaauau                                              19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ugagagagau ccaugguau                                              19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gaccaaagca guauccuua                                              19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
caacgaugcu uggguuugc                                              19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ggggaaagcu gccauugug                                              19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cagauuggau ccagcuuca                                              19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
cgucaugccu uacguggga                                                19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gaucaucucu uacgcucaa                                                19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gaaaucacag ccaauauuc                                                19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uaauaggacu gucuccaaa                                                19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gaaauuggua ccauuguug                                                19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ccacacgacu acaugccca                                                19

```
<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
gcaugccacc cgacccuua                                                19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
cugcuuacgu gccggucua                                                19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gaacuacugg gaucccuaa                                                19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
ccagcgagca ccacaagga                                                19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
guaacugccu guacaacau                                                19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cgacauugca cuccuccaa                                                19

<210> SEQ ID NO 140
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
guggcucucu cgugucuga                                                    19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
cuacgacgau cccuacaaa                                                    19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gagcugcgcc gucaugaaa                                                    19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uagccgagcu cucugauua                                                    19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ccaggcagcu ucauauaau                                                    19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ggauacguga caucaauug                                                    19

<210> SEQ ID NO 146
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
cgaguuugcu uggucagaa                                                  19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggagugggcc ucgauucua                                                  19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
cgaguuugcu uggucagaa                                                  19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ugacaucgac uaccagaaa                                                  19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ggacaaagcc gcuccaccu                                                  19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gagagaaagu ucggccuaa                                                  19

<210> SEQ ID NO 152
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 152
uaugacaugu ccacgguua                                                  19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gauauccgcu guccaauuc                                                  19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gccaaggacc ugauacuaa                                                  19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ggacauaggg uaauuguau                                                  19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uagcugaucu ggccaauga                                                  19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ggacuauauu gugggcuaa                                                  19

<210> SEQ ID NO 158
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 158
gagcagaaag ucucuauaa                                              19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gcauguggcu cagcaauuu                                              19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gaaaagcuau caacaacua                                              19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gauaggcacu gcaacaugg                                              19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ucaagaacaa uacccaagu                                              19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aucaacugcc gcaacaaua                                              19

<210> SEQ ID NO 164
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 164
ucaacaagcc caagaguga                                               19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aagaaguggu acacgauuu                                               19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gaaccuggag cuuuauuau                                               19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ggacuaugaa auccacgau                                               19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ggaagaaggu ccgcguuaa                                               19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
caagacaacu gguuucuaa                                               19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 170
cagagaaccu uauaagaau                                              19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
gaaugaacau aaaccagua                                              19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ggaauuucau aacauggga                                              19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aaacuaugcu ggugauguu                                              19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
auacugagcu ggaagccau                                              19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
acaaggaguu ucuucacaa                                              19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 176
gcugaaaguc cacucauau                                                19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gccgaaagcu ccagucuca                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gcgaagaggu guaaguugc                                                19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ccaaagauau acucaguca                                                19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cuacauuccg uguucauaa                                                19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
caaguacgcc cuccuggau                                                19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 182
cggaggagau cgccuucua                                                19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 183
guucagcgcu gucacuuca                                                19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 184
gaacgccugu gguauguua                                                19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 185
ggacccaucc agacaagua                                                19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 186
ucaaguggcu caacgagaa                                                19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 187
gcgaaacgga cgaggagua                                                19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 188

```
gagcagaccc uguacuuca                                                  19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gaacucaacu caaaacuug                                                  19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gagaagauau acuccauag                                                  19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gaacuacucc cuuucuuca                                                  19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uaacagaggu gaacauaca                                                  19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
cgccuggacu aucauauau                                                  19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
```
agaaugcaau ugauacgga                                          19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gggaacgacu guauagagu                                          19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gaacugggcu uaucuugua                                          19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gugcccagcu cucggaaug                                          19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gggauguccu gcuccaaua                                          19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
ccaccgccgu cugcuguua                                          19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gguggggucu uucccuuua                                          19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ucagagguuu accaagauu                                            19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
caaccacucu ucaccaaua                                            19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cgacaagcau aacgaaccu                                            19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gaaggaggau gccgccuau                                            19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
cgaauuggcu uugcuguca                                            19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ggagaucaau ggacaggau                                            19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
agacgacugu uacaaguuu                                                19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcaccgaccu gguaagcau                                                19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
gaggaacccu gccauguau                                                19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gaggagggcu aacugauug                                                19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gcacggaucu uuacuuuug                                                19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gaacugggca gguuguaga                                                19

```
<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gcaaggaucu cuggaaggu                                                        19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
aguaugggcu uaugauguu                                                        19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
caacgugucu guguuccug                                                        19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gagcacgugu ugucgcugc                                                        19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ggacaucgcu uucaagauc                                                        19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cgggagcgca ggucagauu                                                        19

<210> SEQ ID NO 219
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gcgcaggcuu cggcuauug                                                  19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ccaagaucgu gcagggaua                                                  19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gcaggugagu gucagggua                                                  19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
gggcacaccu ucucccuaa                                                  19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gagcaaagcc ccacuucaa                                                  19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
gaaccuggau gaccauuac                                                  19

<210> SEQ ID NO 225
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ggauucucau caccaguua                                                   19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gaaauacacu auacaccau                                                   19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ggcauaaagg aacguauuu                                                   19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uggcaugaau ugaguauua                                                   19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ccaaggauga ugaguauua                                                   19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gaagacaacc cgugaguau                                                   19

<210> SEQ ID NO 231
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 231
gacaagaucu ucccagcua					19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gaaugaaacu acugcaaug					19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucaaguccau cucuaauuc					19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gaagaaagau ggccccuca					19

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
gaacaacuuu gccgagagg					19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aaacaaggau cuccauuac					19

<210> SEQ ID NO 237
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 237
gaacaacuuu gccgagagg                                                    19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
aaacaaggau cuccguuac                                                    19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
gaagaaagau ggccccuca                                                    19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ucaaguccau cucuaauuc                                                    19

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gaagauggcu ggagcaaug                                                    19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gccaggauau ugugaauca                                                    19

<210> SEQ ID NO 243
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 243
uaaggaagcu ugcaaaguu                                               19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcucgaagcu uaccaucug                                               19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
acacagagcu auucuauug                                               19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gaagagauau gucagaaua                                               19

<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gcaaugcucu gaccacaaa                                               19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gaauggaugu ggagaaaua                                               19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 249
uauaagaggu ggauugaaa                                               19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gagaauacuc gacauguga                                               19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ggagauggau gcaggaguc                                               19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
cugcacaauu gccugauua                                               19

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
guuauucccu cacuucaca                                               19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gcucagaucc caagcccga                                               19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
aggcccaggu cccaucuua                                                    19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gggaugacuc uaugggcaa                                                    19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
ggacuacuau ggaccuuca                                                    19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gagcggagcc cauccuuug                                                    19

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gaaccagacc cguaccuga                                                    19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
gcaagaacac cuuugaguu                                                    19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 261
uaacaaguug gcugaauuu                                                19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
agacaugguu ugauuccua                                                19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
gaaaucccuu uaccuauca                                                19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gacauuaguu caaguagca                                                19

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gaaagugucc cuccucuua                                                19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
gccaguaucu gaagaguuu                                                19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
```
ucacauggau gaagguuaa                                              19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gcaauccagu ucccaguua                                              19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
acggauaucu accgcugua                                              19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ggccagagac aaacaagua                                              19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
acaaugcucc ugcuggaua                                              19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272 uagaucccu acaggaguu                                               19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
acucugacca uuccucuua                                                    19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
gaaaacaccc acaacauaa                                                    19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
cggacucugu acagcaaua                                                    19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ggaagauggu uggcgacgu                                                    19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
ggaucuugcu cauguauuu                                                    19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
gcucuaggca uaccacaua                                                    19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gcagcuagcu ucgauuguu                                                    19

```
<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ggacgaguuu accuacagu                                                        19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
caagacaguu gggugaagu                                                        19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
gaauguuuau gauacggga                                                        19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gucagauucu cagcuuaua                                                        19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gcaaguggca aguucaaca                                                        19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
agacauggau ggccaguuu                                                        19
```

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
uaaagccacu gaauuauga                                                      19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
gaaaguagua gaccuggua                                                      19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
gaacuauacu gucuucuac                                                      19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gacaaucgca gucaucgaa                                                      19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
caagggaagu aguguccua                                                      19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ggaaauucgu gcuaacaga                                                      19

-continued

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
cgggagacgu caauaacuu                                                      19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
guaaaucucu guaugauga                                                      19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
ggaaacugau caugagauu                                                      19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gaagagggau gacaguuga                                                      19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
gaagaaagcu ccaguucau                                                      19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
gaacaguguc gugcuagaa                                                      19

<210> SEQ ID NO 298

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uaacacaccg ccuguaugg                                                19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ggaguacgau cggaagaug                                                19

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
agacgagagu ugcuacaaa                                                19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ucgcgguggu cgucaagua                                                19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gcaaguucgu gcgcggauu                                                19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aaagacagau ggagcguau                                                19

<210> SEQ ID NO 304
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gcaagaccgu gcugggcaa                                                   19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ccaccuggac gucaaauga                                                   19

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
caacaaugac uaugaaaca                                                   19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gggcagcucu ucaccaaug                                                   19

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ugugaaggcu gcccaauuu                                                   19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
auacaucgcu ggccuccug                                                   19

<210> SEQ ID NO 310
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 310
gaugugcucu ccguauguu                                                     19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gcuacaaccc ugagcagau                                                     19

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ggacgaguac ugucucaug                                                     19

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
cuggauaacu ugaccuuga                                                     19

<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ccuguuaaau caugcuuca                                                     19

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ggacacucgu auagccaaa                                                     19

<210> SEQ ID NO 316
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 316
cccuguggcu ggcgauuaa                                                19

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
gaacggaacu gccucauca                                                19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
ggaccugcgu gugcgguuu                                                19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
acaccaagau gauaauuga                                                19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ugccagagga ggcuaauua                                                19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gaacccagcu gccuaacaa                                                19

<210> SEQ ID NO 322
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 322
gcucuagccu gcuggagua                                                19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
ggacaaaggu guucaaauc                                                19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
gcgcacagcu ucuuugaug                                                19

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
gcucaaggcg cuaggcgac                                                19

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uaggcgacga gcugcacca                                                19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ucaaggcgcu aggcgacga                                                19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 328
cugcucggca ggcggaacu                                                 19

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
gcuguagccu ugaugccua                                                 19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
gggacuacuu ggcuacuua                                                 19

<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
caagugcgau guccaccug                                                 19

<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
gcucaggucc uaccaucua                                                 19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
ggaagaaauu caccgauga                                                 19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 334
cgagaaaucu uccuguuca                                               19

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
gacaguccuu cuccuugua                                               19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ggacgauggu gaggacauu                                               19

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uuaaccagcu aucaacuuu                                               19

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
ggacaccucu gcccuuacu                                               19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
gacaacuacu caaagcaaa                                               19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 340
aagcgcuccu uuauccuua                                              19

<210> SEQ ID NO 341
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ccucauggga cgcaaggac                                              19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
gcacagaauc cucgaccca                                              19

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
acgacuaugu gaccucuuu                                              19

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
cgauuugucc ugccaccua                                              19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
gaauauaccu gugaagaua                                              19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
```
gagagaaacu gccauauaa                                                 19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
agacaacucu gaugaauua                                                 19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ggacugauau ucacucauu                                                 19

<210> SEQ ID NO 349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ggacaacugc aacagcgca                                                 19

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gacaacacau gcauaccuu                                                 19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
ggucucagcu gacauucgc                                                 19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uaagcugggu cugacauau                                                    19

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uauauucugc ggccuguuu                                                    19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
gcaaguagug auuggagaa                                                    19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
caacuauacu caugauguu                                                    19

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
gacaguuuau ucugcguug                                                    19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gagaugaaau acugcaaga                                                    19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
gagcaacgca ugccuguuu                                                    19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
ggaaggagcu cucgcuguu                                                19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
aauagaagcu ucacugaga                                                19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ggaugaaccg gcccacuca                                                19

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
gaagcagcga ccagcuaga                                                19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
acaucauuua cggcaugua                                                19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
ggcccauacc gcagcaucu                                                19

```
<210> SEQ ID NO 365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
caagaaagau gcaucaauc                                                    19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
agucauauau gcacaguua                                                    19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ggaauuaucc accauuuaa                                                    19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
ucauauaugc acaguuaga                                                    19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
gaagauuugc gcucucgaa                                                    19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gguacuaauu ugucucuga                                                    19
```

```
<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gcuuaucggu aucgaagug                                                19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
gaguucaguu ucagauuaa                                                19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
gauaauggau ggauucucu                                                19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
gcaaugggcu gcaguuaag                                                19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
gguuuacacu cuucugaua                                                19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
gugccgacuu gguuaauau                                                19

<210> SEQ ID NO 377
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
cggaacagca caagaguua                                                19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aggagauggu caacuauuu                                                19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
cgaggagacu uccgaaucu                                                19

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ugaagcaccu ggagaauga                                                19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ccuacaaacu gucaucaau                                                19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
gcaauaacuu aaaccagua                                                19

<210> SEQ ID NO 383
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ccgcuuaugu ggaggaguu                                               19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
gaaagacaca gcagcguua                                               19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
gaaucuuggu ucagcaauu                                               19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
cagaacacac ccagaguua                                               19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
ugaaauagcu uuaagaacc                                               19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
caacuauaac uacaggauu                                               19

<210> SEQ ID NO 389
<211> LENGTH: 19
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 389
gaaauaacga cuccaggua                                                19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
guaacguacu ccuuucaca                                                19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
caacgugucu cucagccua                                                19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
gcccaaauau uucguuuag                                                19

<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
gaggaggagc gccugauua                                                19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
gaaguuuguu cgaguuuca                                                19

<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
ggaaauccga cgugcaaua                                                   19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
gauauaaucu guggugauc                                                   19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
cggcuaagcu ggccccuaa                                                   19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
gcauaauauu cggcccaaa                                                   19

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
guacucagau gacaauauu                                                   19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ggacaggauu aaagcagca                                                   19

<210> SEQ ID NO 401
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 401
ggacaacacu cggaagauc                                               19

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
aagaaugcau ggugguuaa                                               19

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
guauacugcc ugccuaugu                                               19

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
gaacgaguag guaugucuu                                               19

<210> SEQ ID NO 405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
caaucgaaag cguguagaa                                               19

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ucccauaccu gacgaacug                                               19

<210> SEQ ID NO 407
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 407
caucgggcgu gacuucauu                                                   19

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
agucacgggu ggacaugua                                                   19

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gaacacuccu cuaggguug                                                   19

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
cgacacaugu ugugaugga                                                   19

<210> SEQ ID NO 411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
ggacauaagc ugguuaaca                                                   19

<210> SEQ ID NO 412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
ccaugaagcu cuucaccca                                                   19

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 413
gcaaagugau guuccacag                                                19

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
aguacucgcu ggugcguga                                                19

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
ggaguugggu gaggacgau                                                19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
guaagaagaa cucgcugaa                                                19

<210> SEQ ID NO 417
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
cgaaggagac uaccuaggu                                                19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
gaacaagcaa cucauauuu                                                19

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 419
uaacugaauu gaggagauu                                                        19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
caaauggguu agacguuac                                                        19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
gagcugaacu gggaagaua                                                        19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
gaacauuggu ggaaaguuu                                                        19

<210> SEQ ID NO 423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uuaaagagcu auacacuga                                                        19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
caacagaccu ugcacucaa                                                        19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425

```
gaaacucaau ucagucuau                                              19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426 ugacugggu uggauugua                                               19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gauuauuggu ugugcauua                                              19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
agagcuacau ccuagagua                                              19

<210> SEQ ID NO 429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gcgcaugucu uuccagcuu                                              19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
gcggcuaacu gugucaaua                                              19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
```

```
guaguuauuu cucggauca                                               19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
auggagaacu ugagccuua                                               19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gaacugaacu ucggacaaa                                               19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gaagaaacca uaucaacug                                               19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
gcuguagucu auuauauga                                               19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
gguauucucu uccugauug                                               19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
cgcuauagcu auugcugua                                               19
```

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
gacauuagcu ggcgucuac                                            19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
caacauggcu uuccuagcu                                            19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
uaccauagcu uuaagauac                                            19

<210> SEQ ID NO 441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
caaccuaccu gcacaugug                                            19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
ccaagccacu ggagacuga                                            19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
acacaaagau agucgguau                                            19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
gcaugcuucu ggacuauuu                                              19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
gcaagaggau cggguguau                                              19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
gaaaugaaca ggagucaau                                              19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
gaagagguau ugaaugcua                                              19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
gaagaccugu uuaauaugu                                              19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
cuaagcuggu caacgauaa                                              19

```
<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
ucgcaaugau ccuguguuu                                                 19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
gcggcuacgu caaggucua                                                 19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
aaaccaacau ccaugaaca                                                 19

<210> SEQ ID NO 453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
ccgagaagau gcuccagua                                                 19

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
gcgguuaccu cccacagaa                                                 19

<210> SEQ ID NO 455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
gaagcaauuc caugaguaa                                                 19

<210> SEQ ID NO 456
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
gaggagaagg cauuguaua                                                       19

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
gaacauggga agaguauuu                                                       19

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
acaacauggu guccuauua                                                       19

<210> SEQ ID NO 459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
ggagauagug gaauuaaua                                                       19

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
gaacaaagcg cuuaagugu                                                       19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gaacagaacu uccuuaaca                                                       19

<210> SEQ ID NO 462
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
uaagugaagu uaguagcaa                                                    19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
gcgggaggau uguaagaua                                                    19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
gcacgacgcu uccacaagu                                                    19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
agaauuauuu caugcguga                                                    19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
gaccaaaccu gugcuuaug                                                    19

<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
gaugaucccu acucaagug                                                    19

<210> SEQ ID NO 468
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 468
gcgaucuggu uaugugcaa                                                  19

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
gcguguuucu gcaauagua                                                  19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
gaugaaccca aucccaaua                                                  19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
cuaugcagau gguaguaua                                                  19

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
gaugugucuu ccauucuaa                                                  19

<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
gggcacagga accagguga                                                  19

<210> SEQ ID NO 474
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 474
ggaccugcac ugcggcuuu                                                      19

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
gcagaaagca uccaccugu                                                      19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
gcagugaggg cuccaucuu                                                      19

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
gacagggacg cacuuauga                                                      19

<210> SEQ ID NO 478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ugaggaagca ccagaaauu                                                      19

<210> SEQ ID NO 479
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
gaaaguucac acacaggua                                                      19

<210> SEQ ID NO 480
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 480
aguaauagcu ccacccuca                                                19

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
aggcaaagcu cuagucuca                                                19

<210> SEQ ID NO 482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
gcaguacgac cucaugaau                                                19

<210> SEQ ID NO 483
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
ggucugcacu ccuucaaca                                                19

<210> SEQ ID NO 484
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ggcagagccu uguuuguga                                                19

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
gggaagagau uuacucaaa                                                19

<210> SEQ ID NO 486
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 486
gguaagagcu ucuguggua                                                19

<210> SEQ ID NO 487
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
ggaaagggcu acaauagua                                                19

<210> SEQ ID NO 488
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
ggaaagggcu acaauagua                                                19

<210> SEQ ID NO 489
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
gaagagccgu augaucgaa                                                19

<210> SEQ ID NO 490
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
gaauagcgga cugauguua                                                19

<210> SEQ ID NO 491
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
gggaagagca ugcuuauua                                                19

<210> SEQ ID NO 492
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 492
caagcguaau cucauugua                                              19

<210> SEQ ID NO 493
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
acccggaucu uccaccuua                                              19

<210> SEQ ID NO 494
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
gaggacaccu gguuagaua                                              19

<210> SEQ ID NO 495
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
gcaaauaccu aacucagca                                              19

<210> SEQ ID NO 496
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
guacucggcu cauucacca                                              19

<210> SEQ ID NO 497
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
ggagacaucc ucaaugaua                                              19

<210> SEQ ID NO 498
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 498
gagcagccuu uggauguua                                            19

<210> SEQ ID NO 499
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
cuucggaguu caagaauua                                            19

<210> SEQ ID NO 500
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
gaaggaguuu ccaaaggua                                            19

<210> SEQ ID NO 501
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
ucaaagguuu augugguaa                                            19

<210> SEQ ID NO 502
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
ggaauuucgu uacuucauu                                            19

<210> SEQ ID NO 503
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
auaaauacuu gcuagcaga                                            19

<210> SEQ ID NO 504
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
```
cguauuugau gugucuuua                                          19

<210> SEQ ID NO 505
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
gaaaauagca caaguuaug                                          19

<210> SEQ ID NO 506
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
ggucauaacu gagcaacua                                          19

<210> SEQ ID NO 507
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
caccauaaau cuugacuua                                          19

<210> SEQ ID NO 508
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
uauaugaacu cgaugcuaa                                          19

<210> SEQ ID NO 509
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
gauagcaagu gguacaugc                                          19

<210> SEQ ID NO 510
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
gaacuggguu gcaacauac                                              19

<210> SEQ ID NO 511
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
aaauacagcc accuaauua                                              19

<210> SEQ ID NO 512
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
guauuaagcu aaauggcua                                              19

<210> SEQ ID NO 513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
gaaccaugcc uccaucauc                                              19

<210> SEQ ID NO 514
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
ggccauaccu cuucuccaa                                              19

<210> SEQ ID NO 515
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
gcugcuggcu ucacuaucu                                              19

<210> SEQ ID NO 516
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uaacuucugu gccaacaac                                              19

<210> SEQ ID NO 517
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
gaucaaaccu ugccaccuu                                                   19

<210> SEQ ID NO 518
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
gcaaugaacc uaacaguuu                                                   19

<210> SEQ ID NO 519
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
ggacuggacu ugaucuuug                                                   19

<210> SEQ ID NO 520
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
gaacagcacc uacucaaga                                                   19

<210> SEQ ID NO 521
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
gcaacguggu caucacaaa                                                   19

<210> SEQ ID NO 522
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
gaauacggcu gagcggauc                                                   19

<210> SEQ ID NO 523
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
caagauggcc guggaguau                                                  19

<210> SEQ ID NO 524
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
gagcuacggu auguuugaa                                                  19

<210> SEQ ID NO 525
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
cccacucgcu accugguua                                                  19

<210> SEQ ID NO 526
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
gaugagauuc ugcgcuaua                                                  19

<210> SEQ ID NO 527
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
ggagguacuc gccuuacaa                                                  19

<210> SEQ ID NO 528
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
gaagauccuc caguccuua                                                  19

```
<210> SEQ ID NO 529
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
ccgggucugu gauauauga                                                   19

<210> SEQ ID NO 530
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
gggacauggg cuacacaua                                                   19

<210> SEQ ID NO 531
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
gcaggaccga uaugccuua                                                   19

<210> SEQ ID NO 532
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
gaacuuuggu cucagcuua                                                   19

<210> SEQ ID NO 533
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
ggacacaguu cgaggccag                                                   19

<210> SEQ ID NO 534
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
gagcacaucu uguucaccu                                                   19

<210> SEQ ID NO 535
```

<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
gaauuauccu gacaaggga                                                19

<210> SEQ ID NO 536
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
caacuggagg gagaucuua                                                19

<210> SEQ ID NO 537
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ggacaaagag ggauuauga                                                19

<210> SEQ ID NO 538
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
gugcagagcu guaguauca                                                19

<210> SEQ ID NO 539
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
gaggagaccu ggccaucua                                                19

<210> SEQ ID NO 540
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
ggaacuaggu cucagcuuu                                                19

<210> SEQ ID NO 541
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
aaagaaauac caccaguuu                                              19

<210> SEQ ID NO 542
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
gccagaaagu gaagcuauu                                              19

<210> SEQ ID NO 543
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
ccucaagggu ucuacgguu                                              19

<210> SEQ ID NO 544
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
ucaaugagcu gagcaaugu                                              19

<210> SEQ ID NO 545
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
gaucauaaga aucuggaua                                              19

<210> SEQ ID NO 546
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
gacaguacau ggagagauu                                              19

<210> SEQ ID NO 547
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 547
gccaugggca caauuauaa                                                19

<210> SEQ ID NO 548
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
cuacgggaau gguuaugaa                                                19

<210> SEQ ID NO 549
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
gcauaauucg gcaaagguu                                                19

<210> SEQ ID NO 550
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
caucuuugag gguuuauua                                                19

<210> SEQ ID NO 551
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
gugaagaggu ggccaucua                                                19

<210> SEQ ID NO 552
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
gaaaugcgcg gugguggga                                                19

<210> SEQ ID NO 553
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 553
cgggagacga cguccgcau                                                    19

<210> SEQ ID NO 554
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uggaggagcc ggugaacgu                                                    19

<210> SEQ ID NO 555
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
uggacuggau ccaccacua                                                    19

<210> SEQ ID NO 556
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
ccacauuugu gacgcaaaa                                                    19

<210> SEQ ID NO 557
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
gaagucaccu uugauacaa                                                    19

<210> SEQ ID NO 558
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
caagacgacc uacccgaua                                                    19

<210> SEQ ID NO 559
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 559
cggaugggca guuuaagaa                                                      19

<210> SEQ ID NO 560
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
ccgcggaggc aguucauau                                                      19

<210> SEQ ID NO 561
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
gagaguaaag ucagcauga                                                      19

<210> SEQ ID NO 562
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
gcgauaacau cuaugaaug                                                      19

<210> SEQ ID NO 563
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
guaugagggu gguguauuc                                                      19

<210> SEQ ID NO 564
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
gguguauucu uucucgaua                                                      19

<210> SEQ ID NO 565
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 565
gcauucgccu acuccguga                                               19

<210> SEQ ID NO 566
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
ucaacacccu cuucaugaa                                               19

<210> SEQ ID NO 567
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
caaaccuucu ucucuccug                                               19

<210> SEQ ID NO 568
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
uugaaaggcu cuuagucua                                               19

<210> SEQ ID NO 569
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
acguguuucu ggugcuaaa                                               19

<210> SEQ ID NO 570
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
auggauagau caggaggca                                               19

<210> SEQ ID NO 571
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 571
ugcugaucuu ccaggccua                                               19

<210> SEQ ID NO 572
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
ucgucauccc agugcugau                                               19

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
gccuauggau agaucaggat t                                            21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 574
cccacguacu ccaacuucct t                                            21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
uguccaaacc uucuucucut t                                            21

<210> SEQ ID NO 576
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
guacgugggc accgacuuu                                               19
```

```
<210> SEQ ID NO 577
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
gagccagucu uuccuguau                                                   19

<210> SEQ ID NO 578
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
ugaagacgau ucuggagag                                                   19

<210> SEQ ID NO 579
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
gaacgcaacc uaugcugga                                                   19

<210> SEQ ID NO 580
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
ggagagaucu acagaccaa                                                   19

<210> SEQ ID NO 581
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
ggaaugccau caccggaua                                                   19

<210> SEQ ID NO 582
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
gauuugaucu gaacagcua                                                   19
```

```
<210> SEQ ID NO 583
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
ggacgcacau ccugacauu                                                       19

<210> SEQ ID NO 584
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
uaaaguaaag uguccugua                                                       19

<210> SEQ ID NO 585
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
gcccggagau gaacguuuc                                                       19

<210> SEQ ID NO 586
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
ggccagguca ugaacauuu                                                       19

<210> SEQ ID NO 587
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
gcacauaagg aggcgauua                                                       19

<210> SEQ ID NO 588
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
ggaucuuauu uccuucggag uu                                                   22

<210> SEQ ID NO 589
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
ccgaauaccu cacgccuga                                                19

<210> SEQ ID NO 590
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
gcaagagcau gaacgcgaa                                                19

<210> SEQ ID NO 591
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
gcuacaaacc cgacguuaa                                                19

<210> SEQ ID NO 592
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
gaaccgaucg ugaauaggg                                                19

<210> SEQ ID NO 593
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
agacugagug agaacgaaa                                                19

<210> SEQ ID NO 594
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 594
gaccratcct gtcacctctg ac                                            22

<210> SEQ ID NO 595
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 595
agggcattyt ggacaaakcg tcta                                           24

<210> SEQ ID NO 596
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 596
ggagccaaac gggtcatcat ctc                                            23

<210> SEQ ID NO 597
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 597
gaggggccat ccacagtctt ct                                             22

<210> SEQ ID NO 598
<211> LENGTH: 133
<212> TYPE: PRT
<213> ORGANISM: Homo sapiens

<400> SEQUENCE: 598

Met Asn His Thr Val Gln Thr Phe Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Ala Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130

<210> SEQ ID NO 599
<211> LENGTH: 132
<212> TYPE: PRT
<213> ORGANISM: Homo sapiens

<400> SEQUENCE: 599
```

```
Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Val Pro His Asn Pro Ala Pro Pro Met Ser Thr Val Ile His Ile Arg
            35                  40                  45

Ser Glu Thr Ser Val Pro Asp His Val Val Trp Ser Leu Phe Asn Thr
50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
                100                 105                 110

Gly Ile Phe Met Thr Ile Leu Leu Ile Ile Ile Pro Val Leu Val Val
            115                 120                 125

Gln Ala Gln Arg
    130
```

```
<210> SEQ ID NO 600
<211> LENGTH: 125
<212> TYPE: PRT
<213> ORGANISM: Homo sapiens

<400> SEQUENCE: 600
```

```
Met His Lys Glu Glu His Glu Val Ala Val Leu Gly Ala Pro Pro Ser
1               5                   10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
            35                  40                  45

Trp Cys Cys Leu Gly Phe Ile Ala Phe Ala Tyr Ser Val Lys Ser Arg
50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
            115                 120                 125
```

```
<210> SEQ ID NO 601
<211> LENGTH: 132
<212> TYPE: PRT
<213> ORGANISM: Homo sapiens

<400> SEQUENCE: 601
```

```
Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Gly Pro His Asn Pro Ala Pro Pro Thr Ser Thr Val Ile His Ile Arg
            35                  40                  45

Ser Glu Thr Ser Val Pro Asp His Val Val Trp Ser Leu Phe Asn Thr
50                  55                  60
```

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Val Ile Ile Pro Val Leu Val Val
        115                 120                 125

Gln Ala Gln Arg
    130

<210> SEQ ID NO 602
<211> LENGTH: 125
<212> TYPE: PRT
<213> ORGANISM: Homo sapiens

<400> SEQUENCE: 602

Met His Lys Glu Glu His Glu Val Ala Val Leu Gly Pro Pro Pro Ser
1               5                   10                  15

Thr Ile Leu Pro Arg Ser Thr Val Ile Asn Ile His Ser Glu Thr Ser
                20                  25                  30

Val Pro Asp His Val Val Trp Ser Leu Phe Asn Thr Leu Phe Leu Asn
            35                  40                  45

Trp Cys Cys Leu Gly Phe Ile Ala Phe Ala Tyr Ser Val Lys Ser Arg
50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
        115                 120                 125

<210> SEQ ID NO 603
<211> LENGTH: 137
<212> TYPE: PRT
<213> ORGANISM: Mus musculus

<400> SEQUENCE: 603

Met Asn His Thr Ser Gln Ala Phe Ile Thr Ala Ala Ser Gly Gly Gln
1               5                   10                  15

Pro Pro Asn Tyr Glu Arg Ile Lys Glu Glu Tyr Glu Val Ala Glu Met
                20                  25                  30

Gly Ala Pro His Gly Ser Ala Ser Val Arg Thr Thr Val Ile Asn Met
            35                  40                  45

Pro Arg Glu Val Ser Val Pro Asp His Val Val Trp Ser Leu Phe Asn
50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Ser Thr Leu Val
            100                 105                 110

Leu Ser Ile Leu Met Val Val Ile Thr Ile Val Ser Val Ile Ile Ile
        115                 120                 125

```
Val Leu Asn Ala Gln Asn Leu His Thr
    130                 135
```

<210> SEQ ID NO 604
<211> LENGTH: 144
<212> TYPE: PRT
<213> ORGANISM: Mus musculus

<400> SEQUENCE: 604

```
Met Ser His Asn Ser Gln Ala Phe Leu Ser Thr Asn Ala Gly Leu Pro
1               5                   10                  15

Pro Ser Tyr Glu Thr Ile Lys Glu Glu Tyr Gly Val Thr Glu Leu Gly
            20                  25                  30

Glu Pro Ser Asn Ser Ala Val Val Arg Thr Thr Val Ile Asn Met Pro
        35                  40                  45

Arg Glu Val Ser Val Pro Asp His Val Val Trp Ser Leu Phe Asn Thr
    50                  55                  60

Leu Phe Phe Asn Ala Cys Cys Leu Gly Phe Val Ala Tyr Ala Tyr Ser
65                  70                  75                  80

Val Lys Ser Arg Asp Arg Lys Met Val Gly Asp Val Val Gly Ala Gln
                85                  90                  95

Ala Tyr Ala Ser Thr Ala Lys Cys Leu Asn Ile Ser Ser Leu Ile Phe
            100                 105                 110

Ser Ile Leu Met Val Ile Ile Cys Ile Ile Phe Ser Thr Thr Ser
            115                 120                 125

Val Val Val Phe Gln Ser Phe Ala Gln Arg Thr Pro His Ser Gly Phe
    130                 135                 140
```

<210> SEQ ID NO 605
<211> LENGTH: 106
<212> TYPE: PRT
<213> ORGANISM: Mus musculus

<400> SEQUENCE: 605

```
Met Pro Lys Glu Gln Gln Glu Val Val Val Leu Gly Ser Pro His Ile
1               5                   10                  15

Ser Thr Ser Ala Thr Ala Thr Thr Ile Asn Met Pro Glu Ile Ser Thr
            20                  25                  30

Pro Asp His Val Val Trp Ser Leu Phe Asn Thr Leu Phe Met Asn Phe
        35                  40                  45

Cys Cys Leu Gly Phe Val Ala Tyr Ala Tyr Ser Val Lys Ser Arg Asp
    50                  55                  60

Arg Lys Met Val Gly Asp Thr Thr Gly Ala Gln Ala Phe Ala Ser Thr
65                  70                  75                  80

Ala Lys Cys Leu Asn Ile Ser Ser Leu Phe Phe Thr Ile Leu Thr Ala
                85                  90                  95

Ile Val Val Ile Val Val Cys Ala Ile Arg
            100                 105
```

<210> SEQ ID NO 606
<211> LENGTH: 113
<212> TYPE: PRT
<213> ORGANISM: Gallus gallus

<400> SEQUENCE: 606

```
Met Gln Ser Tyr Pro Gln His Thr Ser Ile Asn Met Pro Ser Tyr Gly
1               5                   10                  15

Gln Asp Val Thr Thr Thr Ile Pro Ile Ser Pro Gln Pro Pro Lys
```

```
            20              25                  30

Asp Phe Val Leu Trp Ser Leu Phe Asn Phe Val Leu Cys Asn Ala Phe
            35                  40                  45

Cys Leu Gly Leu Cys Ala Leu Ser Tyr Ser Ile Lys Ser Arg Asp Arg
        50                  55                  60

Ile Ile Ala Lys Asp Phe Val Gly Ala Ser Tyr Gly Arg Thr Ala
65                  70                  75                  80

Lys Ile Phe Asn Ile Phe Ala Phe Cys Val Gly Leu Leu Val Thr Ile
                85                  90                  95

Leu Ser Ile Val Leu Val Phe Leu Tyr Leu Pro Leu Tyr Thr Val Arg
            100                 105                 110

Pro
```

```
<210> SEQ ID NO 607
<211> LENGTH: 238
<212> TYPE: PRT
<213> ORGANISM: Gallus gallus

<400> SEQUENCE: 607

Met Phe Ser Ile Val Ser Leu Asp Gly Ser Gly Glu Leu Leu Pro Ala
1               5                   10                  15

Pro Gly Gln Gly Trp Gly Ala Pro Arg Pro Ser Ser Leu Leu Ile Ser
            20                  25                  30

Trp Pro Pro Gly Ala Ser Pro Pro Arg Arg Ala Gly Ser Gly His
        35                  40                  45

Gly Arg Ala Ala Asn Glu Trp Ser Gly Gly Gly Ser Gly Gly Arg
50                  55                  60

Gly Arg Gly Ala Ala Arg Ala Glu Arg Gly Arg Arg Pro Ile Ala
65                  70                  75                  80

Ala Arg Arg Gly Gly Val Ser Ala Asn Arg Ser Ala Ala Gly Ala Glu
                85                  90                  95

Pro Glu Gly Ala Pro Arg Val Ala Thr Pro Thr Gly Arg Gln Pro Arg
            100                 105                 110

Ala Gly Pro Arg Gly Leu Arg Gly Glu Arg Pro Arg Phe Arg Pro Arg
        115                 120                 125

Gly Val Gly Glu Arg Gly Gly Asn Ala Ala Gly Gly Asp Gly Ala Val
130                 135                 140

Arg Val Arg Glu Gly Arg Arg Asp Gly Gly Arg Gly Thr Arg Ala Ala
145                 150                 155                 160

Arg Leu Cys Ala Pro Ser Pro Pro Gly Thr Gly Leu Ser Arg Asp Arg
                165                 170                 175

Lys Val Leu Gly Asp Tyr Ser Gly Ala Leu Ser Tyr Gly Ser Thr Ala
            180                 185                 190

Lys Tyr Leu Asn Ile Thr Ala His Leu Ile Asn Val Phe Leu Ile Ile
        195                 200                 205

Leu Ile Ile Ala Leu Val Ala Ser Gly Thr Ile Met Val Ala Asn Ile
210                 215                 220

Phe Asn His Gln Gln Gln His Pro Glu Phe Ile Gly Pro Thr
225                 230                 235
```

```
<210> SEQ ID NO 608
<211> LENGTH: 266
<212> TYPE: PRT
<213> ORGANISM: Gallus gallus

<400> SEQUENCE: 608
```

```
Met Thr Thr Met Ile Thr Lys Pro Arg Arg Glu Arg Ala Gly Gly Ser
1               5                   10                  15

Gly Glu Asp Ala Ala Pro Cys Arg Thr Glu Pro Pro Ala Leu Pro
            20                  25                  30

Gly Thr Ala Arg Pro Arg Pro Pro Ser Ser Pro Ser Arg Asp Gly Thr
            35                  40                  45

Asp Gly Thr Arg Pro Gly Arg Thr Asp Asn Gln Arg Asp Ser Arg Arg
50                  55                  60

Asp Gly Arg Thr Glu Asp Cys Gly Arg Gly Gln Arg Gly Glu Arg Gly
65                  70                  75                  80

Asp Ala Ala Ala Ala Ala Thr Thr Glu Arg Thr Gln Asp Pro
                85                  90                  95

Pro Leu Gly Pro Pro Cys Pro Phe Asp Gly Ala Ala Trp Ala Pro Arg
            100                 105                 110

Pro Pro Pro Gly Pro Gln Gln Gly Cys Phe Ala Cys Ile Ala Lys Pro
            115                 120                 125

Pro Ala Leu Arg His Ala Ser Pro Val Leu Ser Pro Ser Ser Ala Ala
            130                 135                 140

Gln Leu Met Glu Ser Lys Gly Cys Lys Gly Asp Ser Leu Arg Pro Ala
145                 150                 155                 160

Gly Pro Cys Lys His Ser Val Glu Lys Thr Met Thr Asn Pro Thr
            165                 170                 175

Thr Val Ile Glu Ile Tyr Pro Asp Thr Ser Glu Val Asn Asp Tyr Tyr
            180                 185                 190

Leu Trp Ser Ile Phe Asn Phe Val Tyr Leu Asn Phe Cys Cys Leu Gly
            195                 200                 205

Phe Ile Ala Leu Ala Tyr Ser Leu Lys Val Arg Asp Lys Lys Leu Leu
            210                 215                 220

Asn Asp Leu Asn Gly Ala Val Glu Asp Ala Lys Thr Ala Arg Leu Phe
225                 230                 235                 240

Asn Ile Thr Ser Ser Ala Leu Ala Thr Phe Cys Ile Ile Leu Ile Phe
            245                 250                 255

Ile Phe Leu Arg Tyr Pro Leu Thr Asp Tyr
            260                 265

<210> SEQ ID NO 609
<211> LENGTH: 131
<212> TYPE: PRT
<213> ORGANISM: Gallus gallus

<400> SEQUENCE: 609

Met Asp Thr Ser Tyr Pro Arg Glu Asp Tyr Leu Pro Met Thr Ser His
1               5                   10                  15

Lys Arg Asp Ser Ser Pro Thr Thr Ala Thr Ser Ala Pro Pro Arg Asp
            20                  25                  30

His Leu Ile Trp Ser Ile Phe Asn Thr Ile Tyr Met Asn Phe Cys Cys
            35                  40                  45

Leu Gly Phe Val Ala Leu Ala Phe Ser Val Lys Ala Arg Asp Arg Lys
50                  55                  60

Val Ala Gly Asp Val Glu Ala Ala Arg Arg Phe Ser Ser Lys Ala Arg
65                  70                  75                  80

Cys Tyr Asn Ala Leu Ala Thr Ala Gly Ser Val Leu Leu Pro Ile Leu
            85                  90                  95

Leu Ala Ala Leu Val Val Thr Gly Val Leu His Leu Ser Lys Leu Ala
```

```
            100                 105                 110
Gln Asp Ser Val Gly Phe Phe Ser Ser Gln Phe Ser Ala Ser Asp Asp
        115                 120                 125

Glu Asp Lys
        130

<210> SEQ ID NO 610
<211> LENGTH: 145
<212> TYPE: PRT
<213> ORGANISM: Pan troglodytes

<400> SEQUENCE: 610

Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Ala Pro His Asn Pro Ala Pro Pro Met Ser Thr Val Ile His Ile Arg
        35                  40                  45

Ser Glu Thr Ser Val Pro Asp His Val Val Trp Ser Leu Phe Asn Thr
    50                  55                  60

Leu Phe Met Asn Pro Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Leu Met Thr Ile Gly Phe Ile Leu Leu Val Phe Gly Ser
        115                 120                 125

Val Thr Val Tyr His Ile Met Leu Gln Ile Ile Gln Glu Lys Arg Gly
    130                 135                 140

Tyr
145

<210> SEQ ID NO 611
<211> LENGTH: 133
<212> TYPE: PRT
<213> ORGANISM: Pan troglodytes

<400> SEQUENCE: 611

Met Asn His Thr Val Gln Thr Phe Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Ala Pro His Asn Pro Ala Pro Pro Met Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
```

<210> SEQ ID NO 612
<211> LENGTH: 125
<212> TYPE: PRT
<213> ORGANISM: Pan troglodytes

<400> SEQUENCE: 612

Met His Lys Glu Glu His Glu Val Ala Val Leu Gly Ala Pro Pro Ser
1               5                   10                  15

Thr Ile Leu Pro Arg Ser Thr Val Ile Asn Ile His Ser Glu Thr Ser
            20                  25                  30

Val Pro Asp His Val Val Trp Ser Leu Phe Asn Thr Leu Phe Leu Asn
        35                  40                  45

Trp Cys Cys Leu Gly Phe Ile Ala Phe Ala Tyr Ser Val Lys Ser Arg
    50                  55                  60

Asp Arg Lys Met Val Gly Asp Val Thr Gly Ala Gln Ala Tyr Ala Ser
65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Leu Val Phe Gly Ser Val Thr Val Tyr
            100                 105                 110

His Ile Met Leu Gln Ile Ile Gln Glu Lys Arg Gly Tyr
        115                 120                 125

<210> SEQ ID NO 613
<211> LENGTH: 127
<212> TYPE: PRT
<213> ORGANISM: Oncorhynchus mykiss

<400> SEQUENCE: 613

Met Asp Gln Pro Pro Tyr Gln Pro Glu Phe Val Pro Met Lys Gly
1               5                   10                  15

Asn Lys Tyr Met Arg Leu Glu Asp Thr His Gly Ala Pro Lys Phe Gln
            20                  25                  30

His Thr Val Val Leu Gly Gln Pro Gln Pro Val Val Pro His Pro Arg
        35                  40                  45

Asp His Ile Ile Trp Ser Leu Cys Ser Leu Val Tyr Cys Asn Pro Phe
    50                  55                  60

Cys Leu Gly Met Leu Ala Val Tyr Phe Ser Ile Lys Ser Arg Asp Arg
65                  70                  75                  80

Lys Met Val Gly Asp Leu Glu Gly Ala Arg Lys His Gly Lys Thr Ala
                85                  90                  95

Cys Cys Phe Asn Thr Val Thr Leu Thr Leu Ala Ile Leu Gly Leu Leu
            100                 105                 110

Phe Phe Phe Ile Thr Tyr Gly Ile Ile Ile Tyr Gln Val Ala His
        115                 120                 125

<210> SEQ ID NO 614
<211> LENGTH: 128
<212> TYPE: PRT
<213> ORGANISM: Oncorhynchus mykiss

<400> SEQUENCE: 614

Met Asp Gln Ser Pro Ser Tyr Gln Pro Glu Phe Val Pro Met Asn Gly
1               5                   10                  15

Asn Lys Tyr Met Arg Leu Glu Asp Pro His Gly Ala Pro Lys Phe Gln
            20                  25                  30

```
His Thr Val Val Leu Gly Leu Pro Gln Pro Val Pro Gln Pro Arg
            35                  40                  45

Asp His Ile Ile Trp Ser Leu Cys Ser Leu Val Tyr Gly Asn Pro Leu
 50                  55                  60

Cys Leu Gly Met Leu Ala Val Tyr Phe Ser Ile Lys Ser Arg Asp Arg
 65                  70                  75                  80

Lys Met Val Gly Asp Leu Glu Gly Ala Arg Lys His Gly Lys Thr Ala
                 85                  90                  95

Arg Cys Phe Asn Val Val Thr Leu Thr Leu Val Ile Leu Gly Leu Leu
                100                 105                 110

Phe Leu Phe Ile Ile Tyr Gly Phe Phe Ile Tyr Asn Ile Ser His Leu
                115                 120                 125

<210> SEQ ID NO 615
<211> LENGTH: 134
<212> TYPE: PRT
<213> ORGANISM: Mus musculus

<400> SEQUENCE: 615

Met Asp Thr Ser Tyr Pro Arg Glu Asp Pro Arg Ala Pro Ser Ser Arg
 1               5                  10                  15

Lys Ala Asp Ala Ala His Thr Ala Leu Ser Met Gly Thr Pro Gly
             20                  25                  30

Pro Thr Pro Arg Asp His Met Leu Trp Ser Val Phe Ser Thr Met Tyr
             35                  40                  45

Leu Asn Leu Cys Cys Leu Gly Phe Leu Ala Leu Val His Ser Val Lys
 50                  55                  60

Ala Arg Asp Gln Lys Met Ala Gly Asn Leu Glu Ala Ala Arg Gln Tyr
 65                  70                  75                  80

Gly Ser Lys Ala Lys Cys Tyr Asn Ile Leu Ala Ala Met Trp Thr Leu
                 85                  90                  95

Val Pro Pro Leu Leu Leu Leu Gly Leu Val Val Thr Gly Ala Leu His
                100                 105                 110

Leu Ser Lys Leu Ala Lys Asp Ser Ala Ala Phe Phe Ser Thr Lys Phe
                115                 120                 125

Asp Glu Glu Asp Tyr Asn
                130

<210> SEQ ID NO 616
<211> LENGTH: 104
<212> TYPE: PRT
<213> ORGANISM: Mus musculus

<400> SEQUENCE: 616

Met Val Lys Arg Asp Pro Asp Ser Ala Pro Val Pro Ser Thr Val Val
 1               5                  10                  15

Cys Ile Asn Ser Asp Val Ile Gln Pro Asp His Ile Thr Trp Ser Thr
             20                  25                  30

Phe Asn Thr Val Phe Met Asn Gly Cys Cys Leu Gly Phe Ile Ala Tyr
             35                  40                  45

Ile Tyr Ser Val Lys Ser Arg Asp Arg Lys Met Val Gly Asp Met Thr
 50                  55                  60

Gly Ala Gln Ser His Ala Ser Thr Ala Lys Ile Leu Asn Ile Leu Ala
 65                  70                  75                  80

Leu Val Ile Ser Leu Ile Phe Tyr Ile Met Leu Ile Val Leu Tyr Ser
                 85                  90                  95
```

```
Phe Asn Leu Leu Gly Asn Gln Arg
            100

<210> SEQ ID NO 617
<211> LENGTH: 107
<212> TYPE: PRT
<213> ORGANISM: Mus musculus

<400> SEQUENCE: 617

Met Pro Lys Asp Gln His Glu Val Val Met Gly Thr Pro His Thr
1               5                   10                  15

Ser Thr Ser Ser Thr Thr Thr Ile Ile Thr Met Pro Glu Ile Ser Lys
            20                  25                  30

Pro Asp Tyr Val Val Trp Ser Leu Phe Asn Thr Leu Phe Met Asn Phe
            35                  40                  45

Cys Cys Leu Gly Phe Ile Ala Tyr Ala Tyr Ser Val Lys Ser Arg Asp
        50                  55                  60

Arg Lys Met Val Gly Asp Met Thr Gly Ala Gln Ala Phe Ala Ser Thr
65                  70                  75                  80

Ala Arg Cys Leu Asn Ile Ser Cys Leu Ile Leu Ser Val Val Met Val
                85                  90                  95

Ile Leu Phe Ile Thr Phe Phe Ala Thr Arg Arg
            100                 105

<210> SEQ ID NO 618
<211> LENGTH: 125
<212> TYPE: PRT
<213> ORGANISM: Macaca mulatta

<400> SEQUENCE: 618

Met His Lys Glu Glu His Glu Val Ser Val Leu Gly Ala Pro His Ser
1               5                   10                  15

Thr Ile Leu Pro Arg Ser Thr Met Ile Asn Ile Gln Ser Glu Thr Ser
            20                  25                  30

Val Pro Asp His Ile Val Trp Ser Leu Phe Asn Thr Ile Phe Leu Asn
            35                  40                  45

Trp Cys Cys Leu Gly Phe Ile Ala Phe Ala Tyr Ser Val Lys Ser Arg
        50                  55                  60

Asp Arg Lys Met Val Gly Asp Val Thr Gly Ala Gln Ala Tyr Ala Ser
65                  70                  75                  80

Thr Ala Lys Cys Leu Asn Ile Ser Ala Leu Ile Val Gly Ile Leu Met
                85                  90                  95

Thr Ile Gly Phe Ile Leu Leu Leu Val Tyr Gly Ser Val Ala Ile Tyr
            100                 105                 110

His Val Met Leu Gln Ile Val Gln Glu Lys Gln Arg Tyr
        115                 120                 125

<210> SEQ ID NO 619
<211> LENGTH: 133
<212> TYPE: PRT
<213> ORGANISM: Macaca mulatta

<400> SEQUENCE: 619

Met Asn His Thr Val Gln Thr Phe Phe Ser Pro Val Asn Ser Gly Gln
1               5                   10                  15

Pro Pro Asn Tyr Glu Met Leu Lys Glu Glu His Asp Val Ala Met Met
            20                  25                  30
```

Gly Ala Pro His Asn Pro Ala Pro Thr Ser Thr Val Ile His Ile
             35                  40                  45

Arg Ser Glu Thr Ser Val Pro Asp His Val Val Trp Ser Leu Phe Asn
 50                  55                  60

Thr Leu Phe Met Asn Pro Cys Cys Leu Gly Phe Ile Ala Phe Ala Tyr
 65                  70                  75                  80

Ser Val Lys Ser Arg Asp Arg Lys Met Val Gly Asp Leu Thr Gly Ala
                 85                  90                  95

Gln Ala Tyr Ala Ser Thr Ala Lys Cys Leu Asn Ile Trp Ala Leu Ile
             100                 105                 110

Leu Gly Ile Leu Met Thr Ile Leu Leu Ile Val Val Pro Val Leu Ile
         115                 120                 125

Phe Gln Ala His Gln
         130

<210> SEQ ID NO 620
<211> LENGTH: 126
<212> TYPE: PRT
<213> ORGANISM: Equus caballus

<400> SEQUENCE: 620

Met Ile Lys Glu Glu His Glu Val Ser Val Leu Gly Ala Pro Gln Ser
 1               5                  10                  15

Ser Ala Pro Met Thr Thr Thr Val Ile Asn Ile His Ser Asp Thr Ser
                 20                  25                  30

Val Pro Asp His Ile Val Trp Ser Leu Phe Asn Thr Leu Phe Met Asn
             35                  40                  45

Trp Cys Cys Leu Gly Phe Val Ala Phe Ala Tyr Ser Val Lys Ser Arg
 50                  55                  60

Asp Arg Lys Met Val Gly Asp Val Thr Gly Ala Gln Ser Tyr Ala Ser
 65                  70                  75                  80

Thr Ala Lys Cys Leu Asn Ile Trp Ala Leu Val Leu Gly Leu Phe Leu
                 85                  90                  95

Ser Thr Gly Phe Ile Val Leu Met Gly Phe Thr Cys Leu Thr Leu Tyr
             100                 105                 110

Gln Ile Ile Val Lys Ala Met Gln Asp Gly Arg Gly Tyr Phe
         115                 120                 125

<210> SEQ ID NO 621
<211> LENGTH: 147
<212> TYPE: PRT
<213> ORGANISM: Equus caballus

<400> SEQUENCE: 621

Met Asn Arg Ser Phe Gln Thr Phe Val Ser Gly Ala His Thr Gly Val
 1               5                  10                  15

Pro Pro Thr Tyr Glu Met Leu Lys Glu Glu His Glu Val Ser Val Leu
                 20                  25                  30

Gly Ala Leu Arg Ser Ser Ala Pro Val Thr Thr Thr Val Ile Asn Ile
             35                  40                  45

His Ser Asp Thr Ser Val Pro Asp His Ile Val Trp Ser Leu Phe Asn
 50                  55                  60

Thr Leu Phe Thr Tyr Trp Cys Cys Cys Leu Gly Phe Val Ala Phe Ala
 65                  70                  75                  80

Tyr Ser Val Lys Ser Arg Asp Arg Lys Met Glu Gly Asp Val Thr Gly
                 85                  90                  95

```
Ala Gln Ser Tyr Ala Ser Thr Ala Lys Cys Leu Asn Ile Ala Ala Leu
            100                 105                 110

Val Met Gly Leu Leu Val Ile Ile Thr Phe Phe Ile Ile Ser Cys Leu
        115                 120                 125

Trp Leu Thr Asp Leu Phe Pro His Ile Leu Ala Ile Ile Met Ser Ser
        130                 135                 140

Arg Asp Tyr
145

<210> SEQ ID NO 622
<211> LENGTH: 137
<212> TYPE: PRT
<213> ORGANISM: Rattus norvegicus

<400> SEQUENCE: 622

Met Asn His Thr Ser Gln Ala Phe Val Asn Ala Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Met Thr Gly Ala
                85                  90                  95

Gln Ala Tyr Ala Ser Thr Ala Lys Cys Leu Asn Ile Ser Ser Leu Val
            100                 105                 110

Leu Ser Ile Leu Met Val Ile Ile Thr Ile Val Thr Val Ile Ile
        115                 120                 125

Ala Leu Asn Ala Pro Arg Leu Gln Thr
        130                 135

<210> SEQ ID NO 623
<211> LENGTH: 144
<212> TYPE: PRT
<213> ORGANISM: Rattus norvegicus

<400> SEQUENCE: 623

Met Ser His Asn Ser Gln Ala Phe Leu Pro Ala Asn Ala Gly Leu Pro
1               5                   10                  15

Pro Ser Tyr Glu Thr Ile Lys Glu Glu Tyr Gly Val Thr Glu Leu Gly
            20                  25                  30

Glu Pro Asn Asn Ser Ala Val Val Arg Thr Thr Val Ile Asn Met Pro
        35                  40                  45

Arg Glu Val Ser Val Pro Asp His Val Val Trp Ser Leu Phe Asn Thr
50                  55                  60

Leu Phe Phe Asn Ala Cys Cys Leu Gly Phe Ile Ala Tyr Ala Tyr Ser
65                  70                  75                  80

Val Lys Ser Arg Asp Arg Lys Met Val Gly Asp Val Ile Gly Ala Gln
            85                  90                  95

Ala Tyr Ala Ser Thr Ala Lys Cys Leu Asn Ile Ser Ser Leu Ile Phe
            100                 105                 110

Ser Val Leu Met Val Ile Cys Ile Ile Phe Ser Thr Thr Ser
        115                 120                 125
```

```
Ala Val Val Phe Gln Ser Leu Ser Gln Arg Thr Pro His Ser Gly Phe
    130                 135                 140

<210> SEQ ID NO 624
<211> LENGTH: 109
<212> TYPE: PRT
<213> ORGANISM: Rattus norvegicus

<400> SEQUENCE: 624

Met Pro Lys Glu Gln Gln Glu Val Val Ile Leu Gly Gly Pro His Thr
1               5                   10                  15

Ser Asn Ser Ala Thr Thr Thr Ile Asn Met Pro Ala Glu Ile Ser
            20                  25                  30

Thr Pro Asp His Val Val Trp Ser Leu Phe Asn Thr Leu Phe Met Asn
            35                  40                  45

Phe Cys Cys Leu Gly Phe Ile Ala Tyr Ser Tyr Ser Val Lys Ser Arg
50                  55                  60

Asp Arg Lys Met Val Gly Asp Val Thr Gly Ala Lys Thr Tyr Ala Ser
65                  70                  75                  80

Thr Ala Lys Cys Leu Asn Ile Ser Ser Val Ile Phe Thr Ile Leu Met
                85                  90                  95

Ala Ile Leu Thr Ile Ile Leu Tyr Ala Thr Lys Arg Thr
                100                 105

<210> SEQ ID NO 625
<211> LENGTH: 146
<212> TYPE: PRT
<213> ORGANISM: Bos taurus

<400> SEQUENCE: 625

Met Asn Arg Thr Ser Gln Leu Leu Leu Thr Gly Ala His Gly Ala Val
1               5                   10                  15

Pro Pro Ala Tyr Glu Val Leu Lys Glu Glu His Glu Val Ala Val Leu
            20                  25                  30

Gly Ala Pro Gln Ser Gln Ala Pro Leu Thr Thr Thr Val Ile Asn Ile
            35                  40                  45

Arg Ser Asp Thr Ala Val Pro Asp His Ile Val Trp Ser Leu Phe Asn
50                  55                  60

Thr Ile Phe Met Asn Trp Cys Cys Leu Gly Phe Val Ala Phe Ala Tyr
65                  70                  75                  80

Ser Val Lys Ser Arg Asp Arg Lys Met Val Gly Asp Ile Thr Gly Ala
                85                  90                  95

Gln Ser Tyr Ala Ser Thr Ala Lys Cys Leu Asn Ile Cys Ser Leu Val
                100                 105                 110

Leu Gly Ile Leu Leu Thr Val Val Leu Ile Val Leu Val Ser Thr Gly
                115                 120                 125

Ser Leu Met Ile Val Gln Ala Val Ser Glu Leu Met Gln Asn Tyr Gly
                130                 135                 140

Gly His
145

<210> SEQ ID NO 626
<211> LENGTH: 124
<212> TYPE: PRT
<213> ORGANISM: Bos taurus

<400> SEQUENCE: 626

Met Ile Lys Glu Glu His Glu Val Ala Val Leu Gly Ala Pro Gln Ser
```

```
              1               5                  10                 15
            Gln Ala Pro Leu Thr Thr Thr Val Ile Asn Ile Arg Ser Asp Thr Ala
                            20                 25                 30

Val Pro Asp His Ile Val Trp Ser Leu Phe Asn Thr Ile Phe Leu Asn
                            35                 40                 45

Trp Cys Cys Leu Gly Phe Val Ala Phe Ala Tyr Ser Val Lys Ser Arg
                            50                 55                 60

Asp Arg Lys Met Val Gly Asp Ile Thr Gly Ala Gln Ser Tyr Ala Ser
            65                             70                 75                 80

Thr Ala Lys Cys Leu Asn Ile Trp Ala Leu Val Leu Gly Ile Phe Leu
                            85                 90                 95

Thr Ile Gly Ser Ile Val Leu Leu Ile Phe Val Tyr Met Ala Ala Tyr
                            100                105                110

Glu Thr Ala Leu Arg Ile Ser Arg His Gly Gly His
                            115                120
```

<210> SEQ ID NO 627
<211> LENGTH: 124
<212> TYPE: PRT
<213> ORGANISM: Bos taurus

<400> SEQUENCE: 627

```
            Met Leu Lys Glu Glu Asn Glu Val Ala Val Leu Gly Ala Pro Gln Ser
            1               5                  10                 15

Gln Ala Pro Val Thr Thr Thr Val Ile Asn Ile Pro Arg Glu Asn Ser
                            20                 25                 30

Val Pro Asp His Ile Val Trp Ser Leu Phe Asn Thr Val Phe Leu Asn
                            35                 40                 45

Trp Cys Cys Leu Gly Phe Val Ala Phe Ala Tyr Ser Val Lys Ser Arg
                            50                 55                 60

Asp Arg Lys Met Val Gly Asp Ile Thr Gly Ala Gln Ser Tyr Ala Ser
            65                             70                 75                 80

Thr Ala Lys Cys Leu Asn Ile Trp Ala Leu Val Leu Gly Ile Phe Leu
                            85                 90                 95

Thr Ile Gly Ser Ile Val Leu Leu Ile Phe Val Tyr Met Ala Ala Tyr
                            100                105                110

Glu Thr Ala Leu Arg Ile Ser Arg His Gly Gly His
                            115                120
```

<210> SEQ ID NO 628
<211> LENGTH: 132
<212> TYPE: PRT
<213> ORGANISM: Homo sapiens

<400> SEQUENCE: 628

```
            Met Asp Thr Ala Tyr Pro Arg Glu Asp Thr Arg Ala Pro Thr Pro Ser
            1               5                  10                 15

Lys Ala Gly Ala His Thr Ala Leu Thr Leu Gly Ala Pro His Pro Pro
                            20                 25                 30

Pro Arg Asp His Leu Ile Trp Ser Val Phe Ser Thr Leu Tyr Leu Asn
                            35                 40                 45

Leu Cys Cys Leu Gly Phe Leu Ala Leu Ala Tyr Ser Ile Lys Ala Arg
                            50                 55                 60

Asp Gln Lys Val Val Gly Asp Leu Glu Ala Ala Arg Arg Phe Gly Ser
            65                             70                 75                 80

Lys Ala Lys Cys Tyr Asn Ile Leu Ala Ala Met Trp Thr Leu Val Pro
```

```
                    85                  90                  95

Pro Leu Leu Leu Gly Leu Val Val Thr Gly Ala Leu His Leu Ala
            100                 105                 110

Arg Leu Ala Lys Asp Ser Ala Ala Phe Phe Ser Thr Lys Phe Asp Asp
            115                 120                 125

Ala Asp Tyr Asp
        130

<210> SEQ ID NO 629
<211> LENGTH: 230
<212> TYPE: PRT
<213> ORGANISM: Influenza A virus

<400> SEQUENCE: 629

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg His Trp Phe Met Leu Met Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Thr Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Asn Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Lys Met Ala Gly
    210                 215                 220

Thr Ile Arg Ser Glu Val
225                 230

<210> SEQ ID NO 630
<211> LENGTH: 230
<212> TYPE: PRT
<213> ORGANISM: Influenza A virus

<400> SEQUENCE: 630

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
```

```
                35                  40                  45
Thr Leu Gly Leu Asp Ile Glu Thr Ala Thr Arg Ala Gly Lys Gln Ile
 50                  55                  60

Val Glu Arg Ile Leu Lys Glu Ser Asp Glu Ala Leu Lys Met Thr
 65                  70                  75                  80

Met Ala Ser Val Pro Ala Ser Arg Tyr Leu Thr Asp Met Thr Leu Glu
                 85                  90                  95

Glu Met Ser Arg His Trp Phe Met Leu Met Pro Lys Gln Lys Val Ala
            100                 105                 110

Gly Pro Leu Cys Ile Arg Met Asp Gln Ala Ile Met Asp Lys Asn Ile
            115                 120                 125

Ile Leu Lys Ala Asn Phe Ser Val Ile Leu Asp Arg Leu Glu Thr Leu
130                 135                 140

Ile Leu Leu Arg Ala Phe Thr Glu Glu Gly Thr Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Asn Asn Thr Val
            180                 185                 190

Arg Val Ser Glu Thr Leu Gln Arg Phe Ala Trp Arg Ser Ser Asn Glu
            195                 200                 205

Asn Gly Arg Pro Pro Leu Thr Pro Lys Gln Lys Arg Lys Met Ala Gly
210                 215                 220

Thr Ile Arg Ser Glu Val
225                 230

<210> SEQ ID NO 631
<211> LENGTH: 230
<212> TYPE: PRT
<213> ORGANISM: Influenza A virus

<400> SEQUENCE: 631

Met Asp Pro Asn Thr Val Ser Ser Phe Gln Val Asp Cys Phe Leu Trp
 1               5                  10                  15

His Val Arg Lys Arg Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asp Ile Lys Thr Ala Thr Arg Ala Gly Lys Gln Ile
 50                  55                  60

Val Glu Arg Ile Leu Lys Glu Ser Asp Glu Ala Leu Lys Met Thr
 65                  70                  75                  80

Met Ala Ser Val Pro Ala Ser Arg Tyr Leu Thr Asp Met Thr Leu Glu
                 85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
            115                 120                 125

Ile Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175
```

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 632
<211> LENGTH: 230
<212> TYPE: PRT
<213> ORGANISM: Influenza A virus

<400> SEQUENCE: 632

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Ile Ala Ser Val Pro Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Pro Pro Lys Gln Lys Arg Lys Met Ala Arg
    210                 215                 220

Thr Ile Lys Ser Glu Val
225                 230

<210> SEQ ID NO 633
<211> LENGTH: 237
<212> TYPE: PRT
<213> ORGANISM: Influenza A virus

<400> SEQUENCE: 633

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
20 25 30

-continued

```
Leu Asp Arg Leu Arg Asp Gln Lys Ser Leu Arg Gly Arg Gly Ser
        35                  40                  45

Thr Leu Gly Leu Asn Ile Glu Ala Ala Thr His Val Gly Lys Gln Ile
    50                  55                  60

Val Glu Lys Ile Leu Lys Glu Glu Ser Asp Glu Ala Leu Lys Met Thr
65                      70                  75                  80

Met Ala Ser Thr Pro Ala Ser Arg Tyr Ile Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Pro Pro Leu Thr Pro Lys Gln Lys Arg Lys Met Ala Arg
    210                 215                 220

Thr Ala Arg Ser Lys Val Arg Arg Asp Lys Met Ala Asp
225                 230                 235
```